US011123047B2

(12) United States Patent
Jaffer et al.

(10) Patent No.: US 11,123,047 B2
(45) Date of Patent: Sep. 21, 2021

(54) HYBRID SYSTEMS AND METHODS FOR MULTI-MODAL ACQUISITION OF INTRAVASCULAR IMAGING DATA AND COUNTERACTING THE EFFECTS OF SIGNAL ABSORPTION IN BLOOD

(71) Applicant: The General Hospital Corporation, Boston, MA (US)

(72) Inventors: Farouc A. Jaffer, Jamaica Plain, MA (US); Vasilis Ntziachristos, Munich (DE)

(73) Assignee: The General Hospital Corporation, Boston, MA (US)

(*) Notice: Subject to any disclaimer, the term of this patent is extended or adjusted under 35 U.S.C. 154(b) by 1325 days.

(21) Appl. No.: 15/130,820

(22) Filed: Apr. 15, 2016

(65) Prior Publication Data

US 2016/0228097 A1   Aug. 11, 2016

Related U.S. Application Data

(63) Continuation-in-part of application No. 12/020,765, filed on Jan. 28, 2008, now Pat. No. 9,332,942, and a
(Continued)

(51) Int. Cl.
*A61B 8/00* (2006.01)
*A61B 8/08* (2006.01)
(Continued)

(52) U.S. Cl.
CPC .......... *A61B 8/5269* (2013.01); *A61B 5/0066* (2013.01); *A61B 5/0073* (2013.01);
(Continued)

(58) Field of Classification Search
CPC .... A61B 5/0048; A61B 5/0066; A61B 5/0071
See application file for complete search history.

(56) References Cited

U.S. PATENT DOCUMENTS

| 2,339,754 A | 1/1944 | Brace et al. |
| 3,601,480 A | 8/1971 | Randall et al. |
(Continued)

FOREIGN PATENT DOCUMENTS

| DE | 4105221 A1 | 9/1991 |
| DE | 4309056 A1 | 9/1994 |
(Continued)

OTHER PUBLICATIONS

Dixon et al, Intravascular near-infrared fluorescence catheter with ultrasound guidance and blood attenuation correction, May 2013, Journal of Biomedical Optics 18(5), 056009-1 to 9 (Year: 2013).*
(Continued)

*Primary Examiner* — Rochelle D Turchen
(74) *Attorney, Agent, or Firm* — Yakov Sidorin; Quarles & Brady LLP

(57) ABSTRACT

A multi-modal catheter combining at least NIRF and IVUs imaging channels used to reveal integrated biological and structural features of a lumen intravascularly imaged through flowing blood in vivo and corrected for distance-related attenuation and/or scattering parameters of in vivo blood to compensate for discovered overestimation of the degree of in-vivo-blood attenuation of NIRF signal Enhancing the sensitivity of detection of vascular injury and/or plaque deposition beyond the capability of a standalone IVUS imaging as a result of the use of such corrected catheter.

17 Claims, 14 Drawing Sheets

Related U.S. Application Data continuation-in-part of application No. 14/437,765, filed as application No. PCT/US2013/065589 on Oct. 18, 2013, now Pat. No. 10,076,248.

(60) Provisional application No. 61/716,881, filed on Oct. 22, 2012, provisional application No. 61/755,057, filed on Jan. 22, 2013.

(51) Int. Cl.

| | | |
|---|---|---|
| *A61B 8/12* | (2006.01) | |
| *A61B 8/06* | (2006.01) | |
| *A61B 5/00* | (2006.01) | |
| *G01N 21/64* | (2006.01) | |
| *G01N 21/47* | (2006.01) | |

(52) U.S. Cl.
CPC .............. *A61B 5/6852* (2013.01); *A61B 8/06* (2013.01); *A61B 8/12* (2013.01); *A61B 8/445* (2013.01); *A61B 8/4416* (2013.01); *A61B 8/5261* (2013.01); *G01N 21/4795* (2013.01); *G01N 21/6456* (2013.01)

(56) References Cited

U.S. PATENT DOCUMENTS

| | | |
|---|---|---|
| 3,856,600 A | 12/1974 | Fields |
| 3,941,121 A | 3/1976 | Olinger et al. |
| 3,973,219 A | 8/1976 | Tang et al. |
| 3,983,507 A | 9/1976 | Tang et al. |
| 4,030,827 A | 6/1977 | Delhaye et al. |
| 4,141,362 A | 2/1979 | Wurster |
| 4,295,738 A | 10/1981 | Meltz et al. |
| 4,300,816 A | 11/1981 | Snitzer et al. |
| 4,303,300 A | 12/1981 | Pressiat et al. |
| 4,428,643 A | 1/1984 | Kay |
| 4,479,499 A | 10/1984 | Alfano |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,770,492 A | 9/1988 | Levin et al. |
| 4,868,834 A | 9/1989 | Fox et al. |
| 4,892,406 A | 1/1990 | Waters |
| 4,925,302 A | 5/1990 | Cutler |
| 4,928,005 A | 5/1990 | Lefevre et al. |
| 4,965,441 A | 10/1990 | Picard |
| 4,965,599 A | 10/1990 | Roddy et al. |
| 4,993,834 A | 2/1991 | Carlhoff et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,120,953 A | 6/1992 | Harris |
| 5,127,730 A | 7/1992 | Brelje et al. |
| 5,197,470 A | 3/1993 | Helfer et al. |
| 5,202,745 A | 4/1993 | Sorin et al. |
| 5,228,001 A | 7/1993 | Birge et al. |
| 5,248,876 A | 9/1993 | Kerstens et al. |
| 5,262,644 A | 11/1993 | Maguire |
| 5,291,885 A | 3/1994 | Taniji et al. |
| 5,293,872 A | 3/1994 | Alfano et al. |
| 5,293,873 A | 3/1994 | Fang |
| 5,304,810 A | 4/1994 | Amos |
| 5,305,759 A | 4/1994 | Kaneko et al. |
| 5,317,389 A | 5/1994 | Hochberg et al. |
| 5,321,501 A | 6/1994 | Swanson et al. |
| 5,353,790 A | 10/1994 | Jacques et al. |
| 5,383,467 A | 1/1995 | Auer et al. |
| 5,411,016 A | 5/1995 | Kume et al. |
| 5,419,323 A | 5/1995 | Kittrell et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,486,701 A | 1/1996 | Norton et al. |
| 5,491,524 A | 2/1996 | Hellmuth et al. |
| 5,491,552 A | 2/1996 | Knuttel |
| 5,526,338 A | 6/1996 | Hasman et al. |
| 5,562,100 A | 10/1996 | Kittrell et al. |
| 5,565,986 A | 10/1996 | Knuttel |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Gunderson et al. |
| 5,621,830 A | 4/1997 | Lucey et al. |
| 5,623,336 A | 4/1997 | Raab |
| 5,697,373 A | 12/1997 | Richards-Kortum et al. |
| 5,698,397 A | 12/1997 | Zarling et al. |
| 5,710,630 A | 1/1998 | Essenpreis et al. |
| 5,716,324 A | 2/1998 | Toida |
| 5,719,399 A | 2/1998 | Alfano et al. |
| 5,735,276 A | 4/1998 | Lemelson |
| 5,740,808 A | 4/1998 | Panescu et al. |
| 5,748,598 A | 5/1998 | Swanson et al. |
| 5,784,352 A | 7/1998 | Swanson et al. |
| 5,785,651 A | 7/1998 | Kuhn et al. |
| 5,795,295 A | 8/1998 | Hellmuth et al. |
| 5,801,826 A | 9/1998 | Williams |
| 5,803,082 A | 9/1998 | Stapleton et al. |
| 5,807,261 A | 9/1998 | Benaron et al. |
| 5,817,144 A | 10/1998 | Gregory |
| 5,840,023 A | 11/1998 | Oraevsky et al. |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,920,373 A | 7/1999 | Bille |
| 5,920,390 A | 7/1999 | Farahi et al. |
| 5,921,926 A | 7/1999 | Rolland et al. |
| 5,949,929 A | 9/1999 | Hamm |
| 5,951,482 A | 9/1999 | Winston et al. |
| 5,956,355 A | 9/1999 | Swanson et al. |
| 5,968,064 A | 10/1999 | Selmon et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 6,002,480 A | 12/1999 | Izatt et al. |
| 6,004,314 A | 12/1999 | Wei et al. |
| 6,006,128 A | 12/1999 | Izatt et al. |
| 6,010,449 A | 1/2000 | Selmon et al. |
| 6,014,214 A | 1/2000 | Li |
| 6,033,721 A | 3/2000 | Nassuphis |
| 6,044,288 A | 3/2000 | Wake et al. |
| 6,048,742 A | 4/2000 | Weyburne et al. |
| 6,053,613 A | 4/2000 | Wei et al. |
| 6,069,698 A | 5/2000 | Ozawa et al. |
| 6,091,496 A | 7/2000 | Hill |
| 6,091,984 A | 7/2000 | Perelman et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |

(56) References Cited

U.S. PATENT DOCUMENTS

| | | | |
|---|---|---|---|
| 6,160,826 A | 12/2000 | Swanson et al. | |
| 6,161,031 A | 12/2000 | Hochman et al. | |
| 6,166,373 A | 12/2000 | Mao | |
| 6,174,291 B1 | 1/2001 | McMahon et al. | |
| 6,175,669 B1 | 1/2001 | Colston et al. | |
| 6,185,271 B1 | 2/2001 | Kinsinger | |
| 6,191,862 B1 | 2/2001 | Swanson et al. | |
| 6,193,676 B1 | 2/2001 | Winston et al. | |
| 6,198,956 B1 | 3/2001 | Dunne | |
| 6,201,989 B1 | 3/2001 | Whitehead et al. | |
| 6,208,415 B1 | 3/2001 | De Boer et al. | |
| 6,208,887 B1 | 3/2001 | Clarke | |
| 6,249,349 B1 | 6/2001 | Lauer | |
| 6,263,234 B1 | 7/2001 | Engelhardt et al. | |
| 6,264,610 B1 | 7/2001 | Zhu | |
| 6,272,376 B1 | 8/2001 | Marcu et al. | |
| 6,274,871 B1 | 8/2001 | Dukor et al. | |
| 6,282,011 B1 | 8/2001 | Tearney et al. | |
| 6,308,092 B1 | 10/2001 | Hoyns | |
| 6,324,419 B1 | 11/2001 | Guzelsu et al. | |
| 6,341,036 B1 | 1/2002 | Tearney et al. | |
| 6,353,693 B1 | 3/2002 | Kano et al. | |
| 6,359,692 B1 | 3/2002 | Groot | |
| 6,377,349 B1 | 4/2002 | Fercher | |
| 6,384,915 B1 | 5/2002 | Everett et al. | |
| 6,393,312 B1 | 5/2002 | Hoyns | |
| 6,394,964 B1 | 5/2002 | Sievert, Jr. et al. | |
| 6,421,164 B2 | 7/2002 | Tearney et al. | |
| 6,445,944 B1 | 9/2002 | Ostrovsky | |
| 6,459,487 B1 | 10/2002 | Chen et al. | |
| 6,463,313 B1 | 10/2002 | Winston et al. | |
| 6,469,846 B2 | 10/2002 | Ebizuka et al. | |
| 6,485,413 B1 | 11/2002 | Boppart et al. | |
| 6,485,482 B1 | 11/2002 | Belef | |
| 6,501,551 B1 | 12/2002 | Tearney et al. | |
| 6,501,878 B2 | 12/2002 | Hughes et al. | |
| 6,549,801 B1 | 4/2003 | Chen et al. | |
| 6,552,796 B2 | 4/2003 | Magnin et al. | |
| 6,556,305 B1 | 4/2003 | Aziz et al. | |
| 6,556,853 B1 | 4/2003 | Cabib et al. | |
| 6,558,324 B1 | 5/2003 | Von Behren et al. | |
| 6,564,087 B1 | 5/2003 | Pitris et al. | |
| 6,564,089 B2 | 5/2003 | Izatt et al. | |
| 6,575,965 B1 | 6/2003 | Fitch et al. | |
| 6,615,071 B1 | 9/2003 | Casscells, III et al. | |
| 6,622,732 B2 | 9/2003 | Constantz | |
| 6,680,780 B1 | 1/2004 | Fee | |
| 6,685,885 B2 | 2/2004 | Nolte et al. | |
| 6,687,007 B1 | 2/2004 | Meigs | |
| 6,687,010 B1 | 2/2004 | Horii et al. | |
| 6,687,036 B2 | 2/2004 | Riza | |
| 6,741,355 B2 | 5/2004 | Drabarek | |
| 6,790,175 B1 | 9/2004 | Furusawa et al. | |
| 6,806,963 B1 | 10/2004 | Walti et al. | |
| 6,816,743 B2 | 11/2004 | Moreno et al. | |
| 6,839,496 B1 | 1/2005 | Mills et al. | |
| 6,903,820 B2 | 6/2005 | Wang | |
| 6,980,299 B1 | 12/2005 | de Boer | |
| 7,006,231 B2 | 2/2006 | Ostrovsky et al. | |
| 7,231,243 B2 | 6/2007 | Tearney et al. | |
| 7,310,150 B2 | 12/2007 | Guillermo et al. | |
| 7,333,647 B2 | 2/2008 | Boas et al. | |
| 7,365,859 B2 | 4/2008 | Yun et al. | |
| 7,366,376 B2 | 4/2008 | Shishkov et al. | |
| 7,418,169 B2 | 8/2008 | Tearney et al. | |
| 7,447,408 B2 | 11/2008 | Bouma et al. | |
| 7,551,293 B2 | 6/2009 | Yelin et al. | |
| 7,567,349 B2 | 7/2009 | Tearney et al. | |
| 7,865,231 B2 | 1/2011 | Tearney et al. | |
| 8,032,200 B2 | 10/2011 | Tearney et al. | |
| 8,922,781 B2 | 12/2014 | Tearney et al. | |
| 9,060,689 B2 | 6/2015 | Tearney et al. | |
| 9,295,391 B1 | 3/2016 | Tearney et al. | |
| 9,332,942 B2 | 5/2016 | Jaffer et al. | |
| 2001/0047137 A1 | 11/2001 | Moreno et al. | |
| 2002/0013529 A1 | 1/2002 | Smith et al. | |
| 2002/0016533 A1 | 2/2002 | Marchitto et al. | |
| 2002/0064341 A1 | 5/2002 | Fauver et al. | |
| 2002/0076152 A1 | 6/2002 | Hughes et al. | |
| 2002/0085209 A1 | 7/2002 | Mittleman et al. | |
| 2002/0093662 A1 | 7/2002 | Chen et al. | |
| 2002/0122246 A1 | 9/2002 | Tearney et al. | |
| 2002/0161357 A1 | 10/2002 | Anderson et al. | |
| 2002/0163622 A1 | 11/2002 | Magnin et al. | |
| 2002/0172485 A1 | 11/2002 | Keaton et al. | |
| 2002/0188204 A1 | 12/2002 | McNamara et al. | |
| 2002/0196446 A1 | 12/2002 | Roth et al. | |
| 2002/0198457 A1 | 12/2002 | Tearney et al. | |
| 2003/0023153 A1 | 1/2003 | Izatt et al. | |
| 2003/0026735 A1 | 2/2003 | Nolte et al. | |
| 2003/0028100 A1* | 2/2003 | Tearney | G01B 9/02072 600/431 |
| 2003/0135101 A1 | 7/2003 | Webler | |
| 2003/0164952 A1 | 9/2003 | Deichmann et al. | |
| 2003/0171691 A1 | 9/2003 | Casscells, III et al. | |
| 2003/0199769 A1 | 10/2003 | Podoleanu et al. | |
| 2003/0216719 A1 | 11/2003 | Debenedictis et al. | |
| 2003/0236443 A1 | 12/2003 | Cespedes et al. | |
| 2004/0086245 A1 | 5/2004 | Farroni et al. | |
| 2004/0100631 A1 | 5/2004 | Bashkansky et al. | |
| 2004/0100681 A1 | 5/2004 | Bjarklev et al. | |
| 2004/0133191 A1 | 7/2004 | Momiuchi et al. | |
| 2004/0150829 A1 | 8/2004 | Koch et al. | |
| 2004/0166593 A1 | 8/2004 | Nolte et al. | |
| 2004/0212808 A1 | 10/2004 | Okawa et al. | |
| 2005/0018201 A1 | 1/2005 | de Boer et al. | |
| 2005/0075547 A1 | 4/2005 | Wang | |
| 2005/0083534 A1 | 4/2005 | Riza et al. | |
| 2005/0101859 A1 | 5/2005 | Maschke | |
| 2005/0203420 A1 | 9/2005 | Kleen et al. | |
| 2006/0103850 A1 | 5/2006 | Alphonse et al. | |
| 2006/0155193 A1 | 7/2006 | Leonardi et al. | |
| 2006/0244973 A1 | 11/2006 | Yun et al. | |
| 2007/0009935 A1 | 1/2007 | Joo et al. | |
| 2007/0038040 A1 | 2/2007 | Cense et al. | |
| 2007/0073162 A1 | 3/2007 | Tearney et al. | |
| 2008/0007734 A1 | 1/2008 | Park et al. | |
| 2008/0177183 A1* | 7/2008 | Courtney | A61B 8/12 600/463 |
| 2009/0043191 A1 | 2/2009 | Castella et al. | |
| 2009/0137908 A1 | 5/2009 | Patwardhan | |
| 2011/0144504 A1 | 6/2011 | Tearney et al. | |
| 2012/0022338 A1* | 1/2012 | Subramaniam | A61B 5/0086 600/301 |

FOREIGN PATENT DOCUMENTS

| | | |
|---|---|---|
| DE | 19542955 A1 | 5/1997 |
| DE | 10351319 A1 | 6/2005 |
| EP | 0110201 A2 | 6/1984 |
| EP | 0251062 A2 | 1/1988 |
| EP | 0590268 A1 | 4/1994 |
| EP | 0933096 A2 | 8/1999 |
| EP | 1426799 A2 | 6/2004 |
| GB | 1257778 A | 12/1971 |
| GB | 2030313 A | 4/1980 |
| GB | 2209221 A | 5/1989 |
| JP | H04135550 A | 5/1992 |
| JP | H04135551 A | 5/1992 |
| WO | 9219930 A1 | 11/1992 |
| WO | 9303672 A1 | 3/1993 |
| WO | 9553971 A1 | 12/1995 |
| WO | 9628212 A1 | 9/1996 |
| WO | 9732182 A1 | 9/1997 |
| WO | 9801074 A1 | 1/1998 |
| WO | 9814132 A1 | 4/1998 |
| WO | 9835203 A2 | 8/1998 |
| WO | 9838907 A1 | 9/1998 |
| WO | 9846123 A1 | 10/1998 |
| WO | 9848838 A1 | 11/1998 |
| WO | 9905487 A1 | 2/1999 |
| WO | 9944089 A1 | 9/1999 |
| WO | 9957507 A1 | 11/1999 |
| WO | 0058766 A1 | 10/2000 |

(56) References Cited

FOREIGN PATENT DOCUMENTS

| | | |
|---|---|---|
| WO | 0108579 A1 | 2/2001 |
| WO | 0138820 A1 | 5/2001 |
| WO | 0142735 A1 | 6/2001 |
| WO | 0236015 A1 | 5/2002 |
| WO | 0238040 A2 | 5/2002 |
| WO | 02054027 A1 | 7/2002 |
| WO | 03020119 A2 | 3/2003 |
| WO | 03052478 A1 | 6/2003 |
| WO | 03062802 A2 | 7/2003 |
| WO | 2004034869 A2 | 4/2004 |
| WO | 2004066824 A2 | 8/2004 |
| WO | 2004088361 A2 | 10/2004 |
| WO | 2004105598 A1 | 12/2004 |
| WO | 2005000115 A1 | 1/2005 |
| WO | 2005082225 A1 | 9/2005 |
| WO | 2006014392 A1 | 2/2006 |
| WO | 2005054780 A1 | 6/2006 |
| WO | 2006130797 A2 | 12/2006 |
| WO | 2007038787 A1 | 4/2007 |

OTHER PUBLICATIONS

Jiao, Shuliang et al., "Contrast Mechanisms in Polarization-Sensitive Mueller-Matrix Optical Coherence Tomography and Application in Burn Imaging," Applied Optics, vol. 42, No. 25, Sep. I, 2003, pp. 5191-5197.
Jiao, Shuliang et al., "Depth-Resolved Two-Dimensional Stokes Vectors of Backscattered Light and Mueller Matrices of Biological Tissue Measured with Optical Coherence Tomography," Applied Optics, vol. 39, No. 34, Dec. I, 2000, pp. 6318-6324.
Jiao, Shuliang et al., "Jones-Matrix Imaging of Biological Tissues with Quadruple-Channel Optical Coherence Tomography," Journal of Biomedical Optics, vol. 7, No. 3, Jul. 2002, pp. 350-358.
Jiao, Shuliang et al., "Optical-Fiber-Based Mueller Optical Coherence Tomography," Optics Letters, vol. 28, No. 14, Jul. 15, 2003, pp. 1206-1208.
Jiao, Shuliang et al., "Two-Dimensional Depth-Resolved Mueller Matrix of Biological Tissue Measured with Double-Beam Polarization-Sensitive Optical Coherence Tomography," Optics Letters, vol. 27, No. 2, Jan. 15, 2002, pp. 101-103.
Johnson, C. A., J. L. Keltner, et al. (2002). "Baseline visual field characteristics in the ocular hypertension treatment study." Ophthalmology 109(3): 432-437.
Johnston, Mark H., "Technology Insight: Ablative Techniques for Barrett's Esophagus-Current and Emerging Trends," Nature Clinical Practice Gastroenterology & Hepatology, 2005, 2(7):323-330.
Jones, R. C. (1941). "A new calculus for the treatment of optical systems I. Description and discussion of the calculus." Journal of the Optical Society of America 31(7): 488-493.
Jones, R. C. (1941). "A new calculus for the treatment of optical systems III. The Sohncke theory of optical activity." Journal of the Optical Society of America 31(7): 500-503.
Jones, R. C. (1942). "A new calculus for the treatment of optical systems IV." Journal of the Optical Society of America 32(8): 486-493.
Jones, R. C. (1947). "A New Calculus for the Treatment of Optical Systems. V. A More General Formulation, and Description of Another Calculus." Journal of the Optical Society of America 37(2): 107-110.
Jones, R. C. (1947). "A New Calculus for the Treatment of Optical Systems. VI. Experimental Determination of the Matrix." Journal of the Optical Society of America 37(2): 110-112.
Jones, R. C. (1948). "A New Calculus for the Treatment of Optical Systems. VII. Properties of the N-Matrices." Journal of the Optical Society of America 38(8): 671-685.
Jones, R. C. (1956). "New Calculus for the Treatment of Optical Systems. VIII. Electromagnetic Theory." Journal of the Optical Society of America 46(2): 126-131.
Joo, Chulmin et al., "Spectral-domain optical coherence phase microscopy for quantitative phase-contrast imaging", Optics Letters, 2005, 30(16):2131-2133.
Jopson, R. M., L. E. Nelson, et al. (1999). "Measurement of second-order polarization-mode dispersion vectors in optical fibers." IEEE Photonics Technology Letters 11(9): 1153-1155.
Jost, B. M., A. V. Sergienko, et al. (1998). "Spatial correlations of spontaneously down-converted photon pairs detected with a single-photon-sensitive CCD camera." Optics Express 3(2): 81-88.
Kaplan, B., E. Compain, et al. (2000). "Phase-modulated Mueller ellipsometry characterization of scattering by latex sphere suspensions." Applied Optics 39(4): 629-636.
Kass, M. A., D. K. Heuer, et al. (2002). "The Ocular Hypertension Treatment Study: a randomized trial determines that topical ocular hypotensive medication delays or prevents the onset of primary open-angle glaucoma." Archives of Opthalmology 120(6): 701-713.
Kasuga, Y., J. Arai, et al. (2000). "Optical coherence tomograghy to confirm early closure of macular holes." American Journal of Ophthalmology 130(5): 675-676.
Kaufman, T., S. N. Lusthaus, et al. (1990). "Deep Partial Skin Thickness Burns: A Reproducible Animal Model to Study Burn Wound Healing." Burns 16(1): 13-16.
Kazovsky, L. G. et at., "Heterodyne Detection Through Rain, Snow, and Turbid Media: Effective Receiver Size at Optical Through Millimeter Wavelengths," Applied Optics, vol. 22, pp. 706-710, Mar. 1983.
Kemp, N.J., J. Park, et al. (2005). "High-sensitivity determination of birefringence in turbid media with enhanced polarization-sensitive optical coherence tomography." Journal of the Optical Society of America A 22(3): 552-560.
Kerrigan-Baumrind, L. A., H. A. Quigley, et al. (2000). "Number of ganglion cells in glaucoma eyes compared with threshold visual field tests in the same persons." Investigative Ophthalmology & Visual Science 41(3): 741-748.
Kersey, A. D. et al., "Adaptive Polarization Diversity Receiver Configuration for Coherent Optical Fibre Communications," Electronics Letters, vol. 25, pp. 275-277, Feb. 1989.
Kesen, M. R., G. L. Spaeth, et al. (2002). "The Heidelberg Retina Tomograph vs. clinical impression in the diagnosis of glaucoma." American Journal of Ophthalmology 133(5): 613-616.
Khan, Misban Huzaira, et al., "Intradermally Focused Infrared Laser Pulses: Thermal Effects at Defined Tissue Depths" Lasers in Surgery and Medicine, 2005, 36:270-280.
Kienle, A. and R. Hibst (1995). "A New Optimal Wavelength for Treatment of Port Wine Stains." Physics in Medicine and Biology 40(10): 1559-1576.
Kienle, A., L. Lilge, et al. (1996). "Spatially resolved absolute diffuse reflectance measurements for noninvasive determination of the optical scattering and absorption coefficients of biological tissue." Applied Optics 35(13): 2304-2314.
Kim, B. Y. and S. S. Choi (1981). "Analysis and Measurement of Birefringence in Single-Mode Fibers Using the Backscattering Method." Optics Letters 6(11): 578-580.
Kim, B.M. et al., "Optical Feedback Signal for Ultrashort Laser Pulse Ablation of Tissue", Applied Surface Science, 1998, 127-129:857-862.
Kimel, S., L. 0. Svaasand, et al. (1994). "Differential Vascular Response to Laser Photothermolysis." Journal of Investigative Dermatology 103(5): 693-700.
Kirkpatrick, J. Sean et al., "Optical Assessment of Tissue Mechanical Properties", Proceedings of the SPIE, 2000, vol. 4001, pp. 92-101.
Kirkpatrick, Sean J., et al., "Laser speckle microstrain measurement in vascular tissue", SPIE, 1999, 3598:121-129.
Kirkpatrick, Sean J., et al., "Micromechanical behavior of cortical bone as inferred from laser speckle data", Journal of Biomedical Materials Research, 1998, 39(3):373-379.
Kloppenberg, F. W. H., G. Beerthuizen, et al. (2001). "Perfusion of burn wounds assessed by Laser Doppler Imaging is related to burn depth and healing time." Burns 27(4): 359-363.
Kneipp, K., et al. (1997) "Single molecule detection using surface-enhanced Raman scattering (SERS)", Physical Review Letters 78(9): 1667-1670.

(56) References Cited

OTHER PUBLICATIONS

Knighton, R. W. and X. R. Huang (2002). "Analytical methods for scanning laser polarimetry." Optics Express 10(21): 1179-1189.
Knighton, R. W., X. R. Huang, et al. (2002). "Analytical model of scanning laser polarimetry for retinal nerve fiber layer assessment." Investigative Ophthalmology & Visual Science 43(2): 383-392.
Knuttel, A. and J. M• Schmitt (1993). "Stationary Depth-Profiling Reflectometer Based on Low-Coherence Interferometry." Optics Communications 102(3-4): 193-198.
Knuttel, A. and M. Boehlau-Godau (2000). "Spatially confined and temporally resolved refractive index and scattering evaluation in human skin performed with optical coherence tomography." Journal of Biomedical Optics 5(1): 83-92.
Knuttel, A. R. S., Joseph M.: Shay, M.; Knutson, Jay R. (1994). "Stationary low-coherence light imaging and spectroscopy using a CCD camera." Proc. SPIE, vol. 2135, pp. 239-250.
Knuttel, A., J. M. Schmitt, et al. (1994). "Low-Coherence Reflectometry for Stationary Lateral and Depth Profiling with Acousto-optic Deflectors and a CCD Camera." Optics Letters 19(4): 302-304.
Kobayashi, M., H. Hanafusa, et al. (1991). "Polarization-Independent Interferometric Optical-Time-Domain Reflectometer." Journal of Lightwave Technology 9(5): 623-628.
Kohlhaas, Andreas et al., "High-Resolution OCDR for Testing Integrated-Optical Waveguides: Dispersion-Corrupted Experimental Data Corrected by a Numerical Algorithm," Journal of Lightwave Technology, vol. 9, pp. 1493-1502, Nov. 1991.
Kolios, M. C., M.D. Sherar, et al. (1995). "Large Blood Vessel Cooling in Heated Tissues: A Numerical Study." Physics in Medicine and Biology 40(4): 477-494.
Koozekanani, D., K. Boyer, et al. (2001). "Retinal thickness measurements from optical coherence tomography using a Markov boundary model." IEEE Transactions on Medical Imaging 20(9): 900-916.
Kop, R. H. J. and R. Sprik (1995). "Phase-sensitive interferometry with ultrashort optical pulses." Review of Scientific Instruments 66(12): 5459-5463.
Koski, K.J., et al., "Brillouin imaging", Applied Physics Letters, 2005, 87:061903.
Takada, K. et al., "High-Resolution OFDR with Incorporated Fiber-Optic Frequency Encoder," IEEE Photonics Technology Letters, vol. 4, pp. 1069-1072, Sep. 1992.
Takada, K., A. Himeno, et al. (1991). "Phase-Noise and Shot-Noise Limited Operations of Low Coherence Optical-Time Domain Reflectometry." Applied Physics Letters 59(20): 2483-2485.
Takada, K., et al., "New Measurement System for Fault Location in Optical Wave-Guide Devices Based on an Interometric Technique," Applied Optics, vol. 26, pp. 1603-1606, May 1987.
Takada, Kazumasa et al., "Narrow-band light source with acoustooptic tunable filter for optical low-coherence reflectometry," IEEE Photonics Technology Letters, vol. 8, pp. 658-660, May 1996.
Takagi, Yasunari, "Application of a microscope to Brillouin scattering spectroscopy", Review of Scientific Instruments, 1992, 12:5552-5555.
Takenaka, H. (1973). "A Unified Formalism for Polarization Optics by Using Group-Theory I (Theory)." Japanese Journal of Applied Physics 12(2): 226-231.
Tanaka, H., et al. (1995) "New Method of Superheterodyne Light Beating Spectroscopy for Brillouin-Scattering Using Frequency-Tunable Lasers", Physical Review Letters 74(9): 1609-1612.
Tang, C. L., et al., "Transient effects in wavelength-modulated dye lasers", Applied Physics Letters, 1975, 26(9):534-537.
Tang, C. L., et al., "Wide-band electro-optical tuning of semiconductor lasers", Applied Physics Letters, 1977, 30(2):113-116.
Tan-no, N., T. Ichimura, et al. (1994). "Optical Multimode Frequency-Domain Reflectometer." Optics Letters 19(8): 587-589.
Targowski, P., M. Wojtkowski, et al. (2004). "Complex spectral OCT in human eye imaging in vivo." Optics Communications 229(1-6): 79-84.

Tateda, Mitsuhiro et al., "Interferometric Method for Chromatic Dispersion Measurement in a Single-Mode Optical Fiber," IEEE Journal of Quantum Electronics, vol. QE-17, pp. 404-407, Mar. 1981.
Tearney et al., "High-speed phase- and group-delay scanning with a grating-based phase control delay line," Optics Letters, vol. 22, pp. 1811-1813, Dec. 1997.
Tearney, G. J. et al., "Atherosclerotic plaque characterization by spatial and temporal speckle pattern analysis," CLEO 2001, vol. 56, pp. 307.
Tearney, G. J., B. E. Bouma, et al. (1996). "Rapid acquisition of in vivo biological images by use of optical coherence tomography." Optics Letters 21(17): 1408-1410.
Tearney, G. J., B. E. Bouma, et al. (1997). "In vivo endoscopic optical biopsy with optical coherence tomography." Science 276(5321): 2037-2039.
Tearney, G. J., et al., "Spectrally encoded miniature endoscopy", Optical Letters, 2002, 27(6):412-414.
Tearney, G. J., H. Yabushita, et al. (2003). "Quantification of macrophage content in atherosclerotic plaques by optical coherence tomography." Circulation 107(1): 113-119.
Tearney, G. J., I. K. Jang, et al. (2000). "Porcine coronary imaging in vivo by optical coherence tomography." Acta Cardiologica 55(4): 233-237.
Tearney, G. J., M. E. Brezinski, et al. (1995). "Determination of the refractive index of highly scattering human tissue by optical coherence tomography." Optics Letters 20(21): 2258-2260.
Tearney, G. J., M. E. Brezinski, et al. (1996). "Catheter-based optical imaging of a human coronary artery." Circulation 94(11): 3013-3013.
Tearney, G. J., M. E. Brezinski, et al. (1997). "Optical biopsy in human gastrointestinal tissue using optical coherence tomography." American Journal of Gastroenterology 92(10): 1800-1804.
Tearney, G. J., R. H. Webb, et al. (1998). "Spectrally encoded confocal microscopy." Optics Letters 23(15): 1152-1154.
Tearney, G. J., S. A. Boppart, et al. (1996). Scanning single-mode fiber optic catheter-endoscope for optical coherence tomography, Optics Letters 21(7): 543-545.
Telle, M. John, et al., "New method for electro-optical tuning of tunable lasers", Applied Physics Letters, 1974, 24(2):85-87.
Telle, M. John, et al., "Very rapid tuning of cw dye laser", Applied Physics Letters, 1975, 26(10):572-574.
Thompson et al., "Diffusive media characterization with laser speckle", Applied Optics, 1997, 36(16):3726-3734.
Thompson et al., "Imaging in scattering media by use of laser speckle", J. Opt. Soc. Am. A., 1997, 14(9):2269-2277.
Thomsen, Sharon, et al., "Microscopic Correlates of Macroscopic Optical Property Changes During Thermal Coagulation of Myocardium", SPIE, 1990, vol. 1202, pp. 2-11.
Todorovic, Milos et al., "Determination of Local Polarization Properties of Biological Samples in the Presence of Diattenuation by use of Mueller Optical Coherence Tomography," Optics Letters, vol. 29, No. 20, Oct. 15, 2004, pp. 2402-2404.
Toida, M. et al., "Two-Dimensional Coherent Detection Imaging in Multiple Scattering Media Based on the Directional Resolution Capability of the Optical Heterodyne Method," Applied Physics B, vol. 52, pp. 391-394, 1991.
Tower, T. T. and R. T. Tranquillo (2001). "Alignment maps of tissues: I. Microscopic elliptical polarimetry." Biophysical Journal 81(5): 2954-2963.
Tower, T. T. and R. T. Tranquillo (2001). "Alignment maps of tissues: II. Fast harmonic analysis for imaging." Biophysical Journal 81(5): 2964-2971.
Tripathi, Renu et al., "Spectral Shaping for Non-Gaussian Source Spectra in Optical Coherence Tomography," Optics Letters, vol. 27, No. 6, Mar. 15, 2002, pp. 406-408.
Troy, T. L. and S. N. Thennadil (2001). "Optical properties of human skin in the near infrared wavelength range of 1000 to 2200 nm." Journal of Biomedical Optics 6(2): 167-176.
Trutna, W. R. et al., "Continuously Tuned External-Cavity Semiconductor-Laser," Journal of Lightwave Technology, vol. 11, pp. 1279-1286, Aug. 1993.

(56) References Cited

OTHER PUBLICATIONS

Tuchin, Valery V., "Coherent Optical Techniques for the Analysis of Tissue Structure and Dynamics," Journal of Biomedical Optics, 1999, 4(1):106-124.
Uttam, Deepak et al., "Precision Time Domain Reflectometry in Optical Fiber Systems Using a Frequency Modulated Continuous Wave Ranging Technique," Journal of Lightwave Technology, vol. LT-3, pp. 971-977, Oct. 1985.
Vabre, L., A. Dubois, et al. (2002). "Thermal-light full-field optical coherence tomography." Optics Letters 27(7): 530-532.
Vakhtin, A. B., D. J. Kane, et al. (2003). "Common-path interferometer for frequency-domain optical coherence tomography." Applied Optics 42(34): 6953-6958.
Vakhtin, A. B., K. A. Peterson, et al. (2003). "Differential spectral interferometry: an imaging technique for biomedical applications." Optics Letters 28(15): 1332-1334.
Vakoc, B. J., S. H. Yun, et al. (2005). "Phase-resolved optical frequency domain imaging." Optics Express 13(14): 5483-5493.
Van den Boogert, J., et al., "Endoscopic Ablation Therapy for Barrett's Esophagus with High-Grade Dysplasia: A Review", The American Journal of Gastroenterology, 1999, 94(5):1153-1160.
Van Leeuwen, T. G., M.D. Kulkarni, et al. (1999). "High-flow-velocity and shear-rate imaging by use of color Doppler optical coherence tomography." Optics Letters 24(22): 1584-1586.
Vansteenkiste, N., P. Vignolo, et al. (1993). "Optical Reversibility Theorems for Polarization: Application to Remote Control of Polarization." Journal of the Optical Society of America A 10(10): 2240-2245.
Vargas, O., E. K. Chan, et al. (1999). "Use of an agent to reduce scattering in skin." Lasers in Surgery and Medicine 24(2): 133-141.
Vogel, Alfred, et al., "Mechanisms of Pulsed Laser Ablation of Biological Tissues", American Chemical Society, 2003, 103:577-644.
Von der Weid, J.P. et al., "On the Characterization of Optical Fiber Network Components with Optical Frequency Domain Reflectometry," Journal of Lightwave Technology, vol. 15, pp. 1131-1141, Jul. 1997.
Wang, R. K. (1999). "Resolution improved optical coherence-gated tomography for imaging through biological tissues." Journal of Modern Optics 46(13): 1905-1912.
Wang, X. J., T. E. Milner, et al. (1995). "Characterization of Fluid Flow Velocity by Optical Doppler Tomography." Optics Letters 20(11): 1337-1339.
Kramer, R. Z., J. Bella, et al. (1999). "Sequence dependent conformational variations of collagen triple-helical structure." Nature Structural Biology 6(5): 454-457.
Kubba, A. K., et al., "Role of p53 Assessment in Management of Barrett's Esophagus", Digestive Disease and Sciences, 1999, 44(4):659-667.
Kuipers, E. J., et al., "Diagnostic and Therapeutic Endoscopy", Journal of Surgical Oncology, 2005, 92:203-209.
Kulkarni et al., "Image enhancement in optical coherence tomography using deconvolution," Electronics Letters, vol. 33, pp. 1365-1367, Jul. 1997.
Kulkarni, M.D., T. G. van Leeuwen, et al. (1998). "Velocity-estimation accuracy and frame-rate limitations in color Doppler optical coherence tomography." Optics Letters 23(13): 1057-1059.
Kuranov, R.V. et al., "Complementary Use of Cross-Polarization and Standard OCT for Differential Diagnosis of Pathological Tissues," Optics Express, vol. 10, No. 15, Jul. 29, 2002, pp. 707-713.
Kwon, Y. H., C. S. Kim, et al. (2001). "Rate of visual field loss and long-term visual outcome in primary open-angle glaucoma." American Journal of Ophthalmology 132(1): 47-56.
Kwong K. F., D. Yankelevich, et al. (1993). "400-Hz Mechanical Scanning Optical Delay Line." Optics Letters 18(7): 558-560.
Landers, J., I. Goldberg, et al. (2002). "Analysis of risk factors that may be associated with progression from ocular hypertension to primary open angle glaucoma." Clinical and Experimental Ophthalmology 30(4): 242-247.

Larkin, Kieran G., "Efficient Nonlinear Algorithm for Envelope Detection in White Light Interferometry," Journal of the Optical Society of America A, vol. 13, pp. 832-843, Apr. 1996.
Laszlo A. and A. Venetianer (1998). "Heat resistance in mammalian cells: lessons and challenges." Annals of the New York Academy of Sciences 851: 169-178.
Lauer V., "New approach to optical diffraction tomography yielding a vector equation of diffraction tomography and a novel tomographic microscope", Journal of Microscopy, 2002, 205(Pt. 2):165-176.
Laufer, J ., R. Simpson, et al. (1998). "Effect of temperature on the optical properties of ex vivo human dermis and subdermis." Physics in Medicine and Biology 43(9): 2479-2489.
Le Roy-Brehonnet, F. and B. LeJeune (1997). "Utilization of Mueller matrix formalism to obtain optical targets depolarization and polarization properties." Progress in Quantum Electronics 21(2): 109-151.
Le Roy-Brehonnet, F., et al., "Optical Media and Target Characterization by Mueller Matrix Decomposition," J. Phys. D: Appl. Phys. 29, 1996, pp. 34-38.
Lederer, D. E., J. S. Schuman, et al. (2003). "Analysis of macular volume in normal and glaucomatous eyes using optical coherence tomography." American Journal of Ophthalmology 135(6): 838-843.
Lee, P. P., Z. W. Feldman, et al. (2003). "Longitudinal prevalence of major eye diseases." Archives of Ophthalmology 121(9): 1303-1310.
Lees, S., et al., "Studies of Compact Hard Tissues and Collagen by Means of Brillouin Light Scattering", Connective Tissue Research, 1990, 24:187-205.
Lehrer, M. S., T. T. Sun, et al. (1998). "Strategies of epithelial repair: modulation of stem cell and transit amplifying cell proliferation." Journal of Cell Science 111(Pt 19): 2867-2875.
Leibowitz, H. M., D. E. Krueger, et at. (1980). "The Framingham Eye Study monograph: An ophthalmological and epidemiological study of cataract, glaucoma, diabetic retinopathy, macular degeneration, and visual acuity in a general population of 2631 adults, 1973-1975." Survey of Ophthalmology 24(Suppl): 335-610.
Leitgeb R. A., C. K. Hitzenberger, et al. (2003). "Phase-shifting algorithm to achieve high-speed long-depth-range probing by frequency-domain optical coherence tomography." Optics Letters 28(22): 2201-2203.
Leitgeb R. A., L. Schmetterer, et al. (2003). "Real-time assessment of retinal blood flow with ultrafast acquisition by color Doppler Fourier domain optical coherence tomography." Optics Express 11(23): 3116-3121.
Leitgeb R. A., L. Schmetterer, et al. (2004). "Real-time measurement of in vitro flow by Fourier domain color Doppler optical coherence tomography." Optics Letters 29 (2): 171-173.
Leitgeb R. A., W. Drexler, et al. (2004). "Ultrahigh resolution Fourier domain optical coherence tomography." Optics Express 12(10): 2156-2165.
Leitgeb, R. et al., "Spectral measurement of Absorption by Spectroscopic Frequency-Domain Optical Coherence Tomography," Optics Letters, vol. 25, pp. 820-822, Jun. 2000.
Leitgeb R., C. K. Hitzenberger, et al. (2003). "Performance of fourier domain vs. time domain optical coherence tomography." Optics Express 11(8): 889-894.
Leitgeb, R., L. F. Schmetterer, et al. (2002). "Flow velocity measurements by frequency domain short coherence interferometry." Proc. SPIE 4619: 16-21.
Leske, M. C., A. Heijl, et al. (1999). "Early Manifest Glaucoma Trial. Design and Baseline Data." Ophthalmology 106(11): 2144-2153.
Leske, M. C., A. M. Connell, et al. (1995). "Risk factors for open-angle glaucoma. The Barbados Eye Study." Archives of Ophthalmology 113(7): 918-924.
Leske, M. C., A. M. Connell, et al. (2001). "Incidence of open-angle glaucoma: the Barbados Eye Studies. The Barbados Eye Studies Group" Archives of Ophthalmology 119(1): 89-95.
Lewis, Neil E., et al., "Applications of Fourier Transform Infrared Imaging Microscopy in Neurotoxicity", Annals of the New York Academy of Sciences, 1997, 820(1):234-247.

(56) References Cited

OTHER PUBLICATIONS

Lewis, S. E., J. R. de Boer, et al. (2005). "Sensitive, selective, and analytical improvements to a porous silicon gas sensor." Sensors and Actuators B 110(1): 54-65.
Lexer, F. et al., "Wavelength-Tuning Interferometry of Intraocular Distances," Applied Optics, vol. 36, pp. 6548-6553, Sep. 1997.
Lexer, F., C. K. Hitzenberger, et al. (1999). "Dynamic coherent focus OCT with depth-independent transversal resolution." Journal of Modern Optics 46(3): 541-553.
Li, X., C. Chudoba, et al. (2000). "Imaging needle for optical coherence tomography." Optics Letters 25(20): 1520-1522.
Li, X., T. H. Ko, et al. (2001). "Intraluminal fiber-optic Doppler imaging catheter for structural and functional optical coherence tomography." Optics Letters 26(23): 1906-1908.
Liddington, M.I. and P. G. Shakespeare (1996). "Timing of the thermographic assessment of burns." Burns 22(1): 26-8.
Lin, Victor S.-Y., et al., "A Porous Silicon-Based Optical Interferometric Biosensor," Science, vol. 278, pp. 840-843, Oct. 31, 1997.
Lindmo, T., D. J. Smithies, et al. (1998). "Accuracy and noise in optical Doppler tomography studied by Monte Carlo simulation." Physics in Medicine and Biology 43(10): 3045-3064.
Lisauskas, B. Jennifer et al., "Investigation of Plaque Biomechanics from Intravascular Ultrasound Images using Finite Element Modeling", Proceedings of the 19th International Conference—IEEE Oct. 30-Nov. 2, 1997, pp. 887-888.
Liu, J., X. Chen, et al. (1999). "New thermal wave aspects on burn evaluation of skin subjected to instantaneous heating." IEEE Transactions on Biomedical Engineering 46(4): 420-8.
Loree, H.M., et al., "Mechanical Properties of Model Atherosclerotic Lesion Lipid Pools", Arteriosclerosis and Thrombosis, 1994, 14(2):230-234.
Lu, Shih-Yau et al., "Homogeneous and Inhomogeneous Jones Matrices," J. Opt. Soc. Am. A., vol. 11, No. 2, Feb. 1994, pp. 766-773.
Luke, D. G., R. McBride, et al. (1995). "Polarization mode dispersion minimization in fiber-wound piezoelectric cylinders." Optics Letters 20(24): 2550-2552.
MacNeill, B. D., I. K. Jang, et al. (2004). "Focal and multi-focal plaque macrophage distributions in patients with acute and stable presentations of coronary artery disease." Journal of the American College of Cardiology 44(5): 972-979.
Mahgerefteh, D. and C. R. Menyuk (1999). "Effect of first-order PMD compensation on the statistics of pulse broadening in a fiber with randomly varying birefringence." IEEE Photonics Technology Letters 11(3): 340-342.
Maitland, D. J. and J. T. Walsh, Jr. (1997). "Quantitative measurements of linear birefringence during heating of native collagen." Lasers in Surgery & Medicine 20(3): 310-318.
Majaron, B., S. M. Srinivas, et al. (2000). "Deep coagulation of dermal collagen with repetitive Er:YAG laser irradiation." Lasers in Surgery and Medicine 26(2): 215-222.
Manoharan, R., et al., "Biochemical analysis and mapping of atherosclerotic human artery using FT-IR microspectroscopy", Atherosclerosis, 1993, 103:181-193.
Mansuripur, M. (1991). "Effects of High-Numerical-Aperture Focusing on the State of Polarization in Optical and Magneto-optic Data Storage Systems." Applied Optics 30(22): 3154-3162.
Marshall, G. W., S. J. Marshall, et al. (1997). "The dentin substrate: structure and properties related to bonding." Journal of Dentistry 25(6): 441-458.
Martin, P. (1997). "Wound healing—Aiming for perfect skin regeneration." Science 276(5309): 75-81.
Martinez, O. E. (1987). "3000 Times Grating Compressor with Positive Group Velocity Dispersion: Application to Fiber Compensation in 1.3-1.6 µm Region." IEEE Journal of Quantum Electronics 23(1): 59-64.
Martinez, O. E., J.P. Gordon, et al. (1984). "Negative Group Velocity Dispersion Using Refraction." Journal of the Optical System of America A 1(10): 1003-1006.
Matcher, Stephen J. et al., "The Collagen Structure of Bovine Intervertebral Disc Studied Using Polarization-Sensitive Optical Coherence Tomography," Physics in Medicine and Biology, 2004, vol. 49, pp. 1295-1306.
Maurice, Roch L. et al. "Noninvasive Vascular Elastography: Theoretical Framework", IEEE Transactions on Medical Imaging, 2004, 23(2):164-180.
McKenzie, A. L., "Physics of Thermal Processes in Laser-Tissue Interaction", Phys. Med. Biol., 1990, 35(9):1175-1209.
McKinney, J.D., M.A. Webster, et al. (2000). "Characterization and imaging in optically scattering media by use of laser speckle and a variable-coherence source." Optics Letters 25(1): 4-6.
Miglior, S., M. Casula, et al. (2001). "Clinical ability of Heidelberg retinal tomography examination to detect glaucomatous visual field changes." Ophthalmology 108 (9): 1621-1627.
Milner, T. E., D. J. Smithies, et al. (1996). "Depth determination of chromophores in human skin by pulsed photothermal radiometry." Applied Optics 35(19): 3379-3385.
Milner, T. E., D. M. Goodman, et al. (1996). "Imaging laser heated subsurface chromophores in biological materials: Determination of lateral physical dimensions." Physics in Medicine and Biology 41(1): 31-44.
Milner,T. E., D. M. Goodman, et al. (1995). "Depth Profiling of Laser-Heated Chromophores in Biological Tissues by Pulsed Photothermal Radiometry." Journal of the Optical Society of America A 12(7): 1479-1488.
Mishchenko, M.I. and J. W. Hovenier (1995). "Depolarization of Light Backscattered by Randomly Oriented Nonspherical Particles." Optics Letters 20(12): 1356-1358.
Mistlberger, A., J. M. Liebmann, et al. (1999). "Heidelberg retina tomography and optical coherence tomography in normal, ocular-hypertensive, and glaucomatous eyes." Ophthalmology 106(10): 2027-2032.
Mitsui, T. (1999). "High-speed detection of ballistic photons propagating through suspensions using spectral interferometry." Japanese Journal of Applied Physics Part 1—Regular Papers Short Notes & Review Papers 38(5A): 2978-2982.
Mitsui, Takahisa, "Dynamic Range of Optical Reflectometry with Spectral Interferometry," Japanese Journal of Applied Physics Part 1—Regular Papers Short Notes & Review Papers, vol. 38, pp. 6133-6137, 1999.
Molteno, A. C., N.J. Bosma, et al. (1999). "Otago glaucoma surgery outcome study: long-term results of trabeculectomy—1976 to 1995." Ophthalmology 106(9): 1742-50.
Moreau, Julien et al., "Full-Field Birefringence Imaging by Thermal-Light Polarization-Sensitive Optical Coherence Tomography. I. Theory," Applied Optics, vol. 42, No. 19, Jul. 1, 2003, pp. 3800-3810.
Moreau, Julien et al., "Full-Field Birefringence Imaging by Thermal-Light Polarization-Sensitive Optical Coherence Tomography. II. Instrument and Results," Applied Optics, vol. 42, No. 19, Jul. 1, 2003, pp. 3811-3818.
Morelli, J.G., et al., "Tunable Dye Laser (577 nm) Treatment of Port Wine Stains", Lasers in Surgery and Medicine, 1986, 6:94-99.
Morgan, Stephen P. et al., "Surface-Reflection Elimination in Polarization Imaging of Superficial Tissue," Optics Letters, vol. 28, No. 2, Jan. 15, 2003, pp. 114-116.
Morgner, U., F. X. Kartner, et al. (1999). "Sub-two-cycle pulses from a Kerr-lens mode-locked Ti:sapphire laser." Optics Letters 24(6): 411-413.
Morgner, U., W. Drexler, et al. (2000). "Spectroscopic optical coherence tomography." Optics Letters 25(2): 111-113.
Mourant, J. R., A. H. Hielscher, et al. (1998). "Evidence of intrinsic differences in the light scattering properties of tumorigenic and nontumorigenic cells." Cancer Cytopathology 84(6): 366-374.
Muller, M., J. Squier, et al. (1998). "Dispersion pre-compensation of 15 femtosecond optical pulses for high-numerical-aperture objectives." Journal of Microscopy 191(Pt. 2): 141-150.
Muscat, S., N. McKay, et al. (2002). "Repeatability and reproducibility of corneal thickness measurements by optical coherence tomography." Investigative Ophthalmology & Visual Science 43(6): 1791-1795.

(56) References Cited

OTHER PUBLICATIONS

Musch, D. C., P.R. Lichter, et al. (1999). "The Collaborative Initial Glaucoma Treatment Study. Study Design, Methods, and Baseline Characteristics of Enrolled Patients." Ophthalmology 106: 653-662.
Nadkarni, Seemantini K., et al., "Characterization of Atherosclerotic Plaques by Laser Speckle Imaging", Circulation, 2005, 112:885-892.
Nadkarni, Seemantini K., et al., "Measurement of fibrous cap thickness in atherosclerotic plaques by spatiotemporal analysis of laser speckle images", Journal of Biomedical Optics, 2006, 11(2):021006-1-8.
Naganuma, Kazunori et al., "Group-Delay Measurement Using the Fourier-Transform of an Interferometric Cross-Correlation Generated by White Light," Optics Letters, vol. 15, pp. 393-395, Apr. 1990.
Nahen, Kester, et al., "Investigations on Acoustic On-Line Monitoring of IR Laser Ablation of burned Skin", Lasers in Surgery and Medicine, 1999, 25:69-78.
Nassif, N.A. et al., "In Vivo High-Resolution Video-Rate Spectral-Domain Optical Coherence Tomography of the Human Retina and Optic Nerve," Optics Express, vol. 12, No. 3, Feb. 9, 2004, pp. 367-376.
Nassif, Nader et al., "In Vivo Human Retinal Imaging by Ultrahigh-Speed Spectral Domain Optical Coherence Tomography," Optics Letters, vol. 29, No. 5, Mar. 1, 2004, pp. 480-482.
Neerken, S., et al. (2004). "Characterization of age-related effects in human skin: A comparative study that applies confocal laser scanning microscopy and optical coherence tomography." Journal of Biomedical Optics 9(2): 274-281.
Nelson, J. S., K. M. Kelly, et al. (2001). "Imaging blood flow in human port-wine stain in situ and in real time using optical Doppler tomography." Archives of Dermatology 137(6): 741-744.
Neumann, R.A., et al., "Enzyme Histochemical Analysis of Cell Viability After Argon Laser-Induced Coagulation Necrosis of the Skin", Journal of the American Academy of Dermatology, 1991, 25(6):991-998.
Newson, T. P., F. Farahi, et al. (1988). "Combined Interferometric and Polarimetric Fiber Optic Temperature Sensor with a Short Coherence Length Source." Optics Communications 68(3): 161-165.
Nikles, Marc, et al. (1997). "Brillouin gain spectrum characterization in single-mode optical fibers", Journal of Lightwave Technology 15(10): 1842-1851.
November, L. J. (1993). "Recovery of the Matrix Operators in the Similarity and Congruency Transformations: Applications in Polarimetry." Journal of the Optical Society of America A 10(4): 719-739.
Oh, Jung-Taek et al., "Polarization-Sensitive Optical Coherence Tomography for Photoelasticity Testing of Glass/Epoxy Composites," Optics Express, vol. 11, No. 14, Jul. 14, 2003, pp. 1669-1676.
Oh, W. Y., et al., "115 kHz Tuning Repetition Rate Ultrahigh-Speed Wavelength-Swept Semiconductor Laser", Optics Letters, 2005, 30(23):3159-3161.
Oh, W. Y., S. H. Yun, et al. (2005). "Wide tuning range wavelength-swept laser with two semiconductor optical amplifiers." IEEE Photonics Technology Letters 17(3): 678-680.
Oka, K. and T. Kato (1999). "Spectroscopic polarimetry with a channeled spectrum." Optics Letters 24(21): 1475-1477.
Okoshi, Takanori, "Polarization-State Control Schemes for Heterodyne or Homodyne Optical Fiber Communications," Journal of Lightwave Technology, vol. LT-3, pp. 1232-1237, Dec. 1985.
Oshima, M., R. Torii, et al. (2001). "Finite element simulation of blood flow in the cerebral artery." Computer Methods in Applied Mechanics and Engineering 191 (6-7): 661-671.
Overholt, Bergein F., et al., "Photodynamic Therapy for Barrett's Esophagus: Follow-Up in 100 Patients", Gastrointestinal Endoscopy, 1999, 49(1):1-7.
Pan, Y. T., H. K. Xie, et al. (2001). "Endoscopic optical coherence tomography based on a microelectromechanical mirror." Optics Letters 26(24): 1966-1968.

Parisi, V., G. Manni, et al. (2001). "Correlation between optical coherence tomography, pattern electroretinogram, and visual evoked potentials in open-angle glaucoma patients." Ophthalmology 108(5): 905-912.
Park, B. H., M. C. Pierce, et al. (2005). "Real-time fiber-based multi-functional spectral-domain optical coherence tomography at 1.3 μm." Optics Express 13(11): 3931-3944.
Canto, M. I., et al., "Vital Staining and Barrett's Esophagus", Gastrointestinal Endoscopy, 1999, 49(3)(Pt. 2):S12-S16.
Cense, B., et al., "Spectral-domain polarization-sensitive optical coherence tomography at 850 nm", Coherence Domain Optical Methods and Optical Coherence Tomography in Biomedicine IX, Proc. of SPIE, 2005, vol. 5690, pp. 159-162.
Cense, B., N. Nassif, et at. (2004). "Ultrahigh-Resolution High-Speed Retinal Imaging Using Spectral-Domain Optical Coherence Tomography." Optics Express 12(11): 2435-2447.
Cense, B., T. C. Chen, et al. (2004). "Thickness and birefringence of healthy retinal nerve fiber layer tissue measured with polarization-sensitive optical coherence tomography," Investigative Ophthalmology & Visual Science 45(8): 2606-2612.
Cense, Barry et al., "In Vivo Birefringence and Thickness Measurements of the Human Retinal Nerve Fiber Layer Using Polarization-Sensitive Optical Coherence Tomography," Journal of Biomedical Optics, vol. 9, No. I, Jan./Feb. 2004, pp. 121-125.
Cense, Barry et at., "In Vivo Depth-Resolved Birefringence Measurements of the Human Retinal Nerve Fiber Layer by Polarization-Sensitive Optical Coherence Tomography," Optics Letters, vol. 27, No. 18, Sep. 15, 2002, pp. 1610-1612.
Chance, B., J. S. Leigh, et at. (1988). "Comparison of Time-Resolved and Time-Unresolved Measurements of Deoxyhemoglobin in Brain." Proceedings of the National Academy of Sciences of the United States of America 85(14): 4971-4975.
Chang, E. P., D. A. Keedy, et at. (1974). "Ultrastructures of Rabbit Corneal Stroma: Mapping of Optical and Morphological Anisotropies." Biochimica et Biophysica Acta 343(3): 615-626.
Chartier, T., A. Hideur, et al. (2001). "Measurement of the elliptical birefringence of single-mode optical fibers." Applied Optics 40(30): 5343-5353.
Chauhan, B. C., J. W. Blanchard, et al. (2000). "Technique for Detecting Serial Topographic Changes in the Optic Disc and Peripapillary Retina Using Scanning Laser Tomography." Invest Ophthalmol Vis Sci 41: 775-782.
Chen, Z. P., T. E. Milner, et al. (1997). "Noninvasive imaging of in vivo blood flow velocity using optical Doppler tomography." Optics Letters 22(14): 1119-1121.
Chen, Z. P., T. E. Milner, et al. (1997). "Optical Doppler tomographic imaging of fluid flow velocity in highly scattering media." Optics Letters 22(1): 64-66.
Chen, Z. P., Y. H. Zhao, et al. (1999). "Optical Doppler tomography." IEEE Journal of Selected Topics in Quantum Electronics 5(4): 1134-1142.
Cheong, W. F., S. A. Prahl, et al. (1990). "A Review of the Optical Properties of Biological Tissues." IEEE Journal of Quantum Electronics 26(12): 2166-2185.
Chernikov, S. V., Y. Zhu, et al. (1997). "Supercontinuum self-Q-switched ytterbium fiber laser." Optics Letters 22(5): 298-300.
Chinn, S.R. et al., "Optical Coherence Tomography Using a Frequency-Tunable Optical Source," Optics Letters, vol. 22, pp. 340-342, Mar. 1997.
Cho, S. H., B. E. Bouma, et al. (1999). "Low-repetition-rate high-peak-power Kerr-lens mode-locked Ti:Al2O3 laser with a multiple-pass cavity." Optics Letters 24(6): 417-419.
Choma, M.A., C. H. Yang, et at (2003). "Instantaneous quadrature low-coherence interferometry with 3×3 fiber-optic couplers." Optics Letters 28(22): 2162-2164.
Choma, M.A., M. V. Sarunic, et al. (2003). "Sensitivity advantage of swept source and Fourier domain optical coherence tomography." Optics Express 11(18): 2183-2189.
Choplin, N. T. and D. C. Lundy (2001). "The sensitivity and specificity of scanning laser polarimetry in the detection of glaucoma in a clinical setting." Opthalmology 108 (5): 899-904.

(56) References Cited

OTHER PUBLICATIONS

Christens-Barry, W. A., W. J. Green, et at. (1996). "Spatial mapping of polarized light transmission in the central rabbit cornea." Experimental Eye Research 62(6): 651-662.
Chvapil, M., D.P. Speer, et al. (1984). "Identification of the depth of burn injury by collagen stainability." Plastic & Reconstructive Surgery 73(3): 438-441.
Cioffi, G. A. (2001). "Three common assumptions about ocular blood flow and glaucoma." Survey of Opthalmology, 45: S325-S331.
Clark, N., et al., "Tracking Speckle Patterns with Optical Correlation", SPIE, 1992, 1772:77-87.
Coleman, A. L. (1999). "Glaucoma." Lancet 354(9192): 1803-1810.
Collaborative Normal-Tension Glaucoma Study Group (1998). "Comparison of Glaucomatous Progression Between Untreated Patients With Normal Tension Glaucoma and Patients with Therapeutically Reduced Intraocular Pressures." Am J Ophthalmol 126: 487-497.
Collaborative Normal-Tension Glaucoma Study Group (1998). "The effectiveness of intraocular pressure reduction in the treatment of normal-tension glaucoma." Am J Opthalmol 126: 498-505.
Collaborative Normal-Tension Glaucoma Study Group (2001). "Natural History of Normal-Tension Glaucoma." Opthalmology 108: 247-253.
Colston, B. W. Jr., M. J. Everett, et al. (1998). "Imaging of hard- and soft-tissue structure in the oral cavity by optical coherence tomography." Applied Optics 37(16): 3582-3585.
Colston, B. W. Jr., U.S. Sathyam, et al. (1998). "Dental OCT." Optics Express 3(6): 230-238.
Congdon, N. G., D. S. Friedman, et al. (2003). "Important causes of visual impairment in the world today." JAMA—Journal of the American Medical Association 290(15): 2057-2060.
Cregan, R. F., B. J. Mangan, et al. (1999). "Single-mode photonic band gap guidance of light in air." Science 285(5433): 1537-1539.
Dal Molin, M., A. Galtarossa, et al. (1997). "Experimental investigation of linear polarization in high-birefringence single-mode fibers." Applied Optics 36(12): 2526-2528.
Danielson, B. L. and C. D. Whittenberg (1987). "Guided-Wave Reflectometry with Micrometer Resolution." Applied Optics 26(14): 2836-2842.
Danielson, B.L. et al., "Absolute Optical Ranging Using Low Coherence Interferometry," Applied Optics, vol. 30, p. 2975, Jul. 1991.
Dave, D.P. and T. E. Milner (2000). "Doppler-angle measurement in highly scattering media." Optics Letters 25(20): 1523-1525.
Davé, Digant P. et al., "Polarization-maintaining fiber-based optical low-coherence reflectometer for characterization and ranging of birefringence," Optics Letters, vol. 28, No. 19, Oct. 1, 2003, pp. 1775-1777.
De Boer, J. F., C. E. Saxer, et al. (2001). "Stable carrier generation and phase-resolved digital data processing in optical coherence tomography." Applied Optics 40(31): 5787-5790.
De Boer, J. F., T. E. Milner, et al. (1998). "Two dimensional birefringence imaging in biological tissue using phase and polarization sensitive optical coherence tomograghy." OSA Trends in Optics and Photonics, Advances in Optical Imaging and Photon Migration, Orlando, Florida, USA, 1998.
De Boer, Johannes F. et al., "Determination of the Depth-Resolved Stokes Parameters of Light Backscattered from Turbid Media by use of Polarization-Sensitive Optical Coherence Tomography," Optics Letters, vol. 24, No. 5, Mar. 1, 1999, pp. 300-302.
De Boer, Johannes F. et al., "Imaging Thermally Damaged Tissue by Polarization Sensitive Optical Coherence Tomography," Optics Express, vol. 3, No. 6, Sep. 14, 1998, pp. 212-218.
De Boer, Johannes F. et al., "Improved Signal-to-Noise Ratio in Spectral-Domain Compared with Time-Domain Optical Coherence Tomography," Optics Letters, vol. 28, No. 21, Nov. 1, 2003, pp. 2067-2069.
De Boer, Johannes F. et al., "Polarization Effects in Optical Coherence Tomography of Various Biological Tissues," IEEE Journal of Selected Topics in Quantum Electronics, vol. 5, No. 4, Jul./Aug. 1999, pp. 1200-1204.
De Boer, Johannes F. et al., "Review of Polarization Sensitive Optical Coherence Tomography and Stokes Vector Determination," Journal of Biomedical Optics, vol. 7, No. 3, Jul. 2002, pp. 359-371.
De Boer, Johannes F. et al., "Two-Dimensional Birefringence Imaging in Biological Tissue by Polarization-Sensitive Optical Coherence Tomography," Optics Letters, vol. 22, No. 12, Jun. 15, 1997, pp. 934-936.
De Groot, P. and L. Deck (1993). "Three-Dimensional Imaging by Sub-Nyquist Sampling of White-Light Interferograms." Optics Letters 18(17): 1462-1464.
Deckelbaum, Lawrence J., "Coronary Laser Angioplasty", Lasers in Surgery and Medicine, 1994, 14:101-110.
Denk, W., J. H. Strickler, et al. (1990). "Two-Photon Laser Scanning Fluorescence Microscopy." Science 248(4951): 73-76.
Descour, M. R., A. H. 0. Karkkainen, et al. (2002). "Toward the development of miniaturized Imaging systems for detection of pre-cancer." IEEE Journal of Quantum Electronics 38(2): 122-130.
Desjardins A.E., et al., "Speckle reduction in OCT using massively-parallel detection and frequency-domain ranging", Optics Express, 2006, 14(11):4736-4745.
Park, B. Hyle et al., "Comment on Optical-Fiber-Based Mueller Optical Coherence Tomography," Optics Letters, vol. 29, No. 24, Dec. 15, 2004, pp. 2873-2874.
Park, B. Hyle et al., "In Vivo Burn Depth Determination by High-Speed Fiber-Based Polarization Sensitive Optical Coherence Tomography," Journal of Biomedical Optics, vol. 6 No. 4, Oct. 2001, pp. 474-479.
Park, B. Hyle et al., "Jones Matrix Analysis for a Polarization-Sensitive Optical Coherence Tomography System Using Fiber-Optic Components," Optics Letters, vol. 29, No. 21, Nov. 1, 2004, pp. 2512-2514.
Park, B. Hyle et al., "Real-Time Multi-Functional Optical Coherence Tomography," Optics Express, vol. 11, No. 7, Apr. 1, 2003, pp. 782-793.
Park, D. H., J. W .. Hwang, et al. (1998). "Use of laser Doppler flowmetry for estimation of the depth of burns." Plastic and Reconstructive Surgery 101(6): 1516-1523.
Parker, K. J. et al., "Techniques for Elastic Imaging: A Review", IEEE Engineering in Medicine and Biology, Nov./Dec. 1996, pp. 52-59.
Passy, R. et al., "Experimental and Theoretical Investigations of Coherent OFDR with Semiconductor-Laser Sources," Journal of Lightwave Technology, vol. 12, pp. 1622-1630, Sep. 1994.
Pendry, J. B., A. J. Holden, et al. (1999). "Magnetism from conductors and enhanced nonlinear phenomena." IEEE Transactions on Microwave Theory and Techniques 47(11): 2075-2084.
Penninckx, D. and V. Morenas (1999). "Jones matrix of polarization mode dispersion." Optics Letters 24(13): 875-877.
Pfefer, J., et al., (2006) "Performance of the Aer-O-Scope, a Pneumatic, Self Propelling, Self Navigating Colonoscope in Animal Experiments", Gastrointestinal Endoscopy, 2006, 63(5):AB223.
Pierce, M. C., M. Shishkov, et al. (2005). "Effects of sample arm motion in endoscopic polarization-sensitive optical coherence tomography." Optics Express 13(15): 5739-5749.
Pierce, Mark C. et al., "Advances in Optical Coherence Tomography Imaging for Dermatology," Journal of Investigative Dermatology, 2004, vol. 123, pp. 458-463.
Pierce, Mark C. et al., "Birefringence Measurements in Human Skin Using Polarization-Sensitive Optical Coherence Tomography," Journal of Biomedical Optics, vol. 9, No. 2, Mar./Apr. 2004, pp. 287-291.
Pierce, Mark C. et al., "Collagen Denaturation can be Quantified in Burned Human Skin Using Polarization-Sensitive Optical Coherence Tomography," Burns, 2004, pp. 511-517.
Pierce, Mark C. et al., "Simultaneous Intensity, Birefringence, and Flow Measurements with High-Speed Fiber-Based Optical Coherence Tomography," Optics Letters, vol. 27, No. 17, Sep. 1, 2002, pp. 1534-1536.

(56) References Cited

OTHER PUBLICATIONS

Pircher, M., E. Gotzinger, et al. (2003). "Measurement and imaging of water concentration in human cornea with differential absorption optical coherence tomography." Optics Express 11(18): 2190-2197.
Pircher, M., E. Gotzinger, et al. (2003). "Speckle reduction in optical coherence tomography by frequency compounding." Journal of Biomedical Optics 8(3): 565-569.
Pircher, Michael et al., "Imaging of Polarization Properties of Human Retina in Vivo with Phase Resolved Transversal PS-OCT," Optics Express, vol. 12, No. 24, Nov. 29, 2004, pp. 5940-5951.
Pircher, Michael et al., "Three Dimensional Polarization Sensitive OCT of Human Skin In Vivo," Optics Express, 2004, 12(14):3236-3244.
Pircher, Michael et al., "Transversal Phase Resolved Polarization Sensitive Optical Coherence Tomography," Physics in Medicine & Biology, 2004, vol. 49, pp. 1257-1263.
Podbielska, H., "Interferometric Methods and Biomedical Research", SPIE, 1999, 2732:134-141.
Podoleanu, A. G. and D. A. Jackson (1999). "Noise analysis of a combined optical coherence tomograph and a confocal scanning ophthalmoscope." Applied Optics 38(10): 2116-2127.
Podoleanu, A. G., G. M. Dobre, et al. (1998). "En-face coherence imaging using galvanometer scanner modulation." Optics Letters 23(3): 147-149.
Podoleanu, A. G., J. A. Rogers, et al. (2000). "Three dimensional OCT images from retina and skin." Optics Express 7(9): 292-298.
Podoleanu, A. G., M. Seeger, et al. (1998). "Transversal and longitudinal images from the retina of the living eye using low coherence reflectometry." Journal of Biomedical Optics 3(1): 12-20.
Podoleanu, Adrian G., "Unbalanced Versus Balanced Operation in an Optical Coherence Tomography System," Applied Optics, vol. 39, pp. 173-182, Jan. 2000.
Poneros, John M., "Diagnosis of Barrett's esophagus using optical coherence tomography", Gastrointestinal Endoscopy Clinics of North America, 2004, 14:573-588.
Poneros, John M., et al., "Diagnosis of Specialized Intestinal Metaplasia by Optical Coherence Tomography", Gastroenterology, 2001, 120:7-12.
Poole, C. D. (1988). "Statistical Treatment of Polarization Dispersion in Single-Mode Fiber." Optics Letters 13(8): 687-689.
Povazay, B., K. Bizheva, et al. (2002). "Submicrometer axial resolution optical coherence tomography." Optics Letters 27(20): 1800-1802.
Price, J. H. V. et al., "Tunable, Femtosecond Pulse Source Operating in the Range 1.06-1.33 μm Based on an Yb3+-doped Holey Fiber Amplifier," Journal of the Optical Society of America B, vol. 19, pp. 1286-1294, Jun. 2002.
Pyhtila, John W., et al., "Determining nuclear morphology using an improved angle-resolved low coherence interferometry system", Optics Express, 2003, 11(25):3473-3484.
Pyhtila, John W., et al., "Rapid, depth-resolved light scattering measurements using Fourier domain, angle-resolved low coherence interferometry", Optics Express, 2004, 12(25):6178-6183.
Qi, B., A. P. Himmer, et al. (2004). "Dynamic focus control in high-speed optical coherence tomography based on a microelectromechanical mirror." Optics Communications 232(1-6): 123-128.
Radhakrishnan, S., A.M. Rollins, et al. (2001). "Real-time optical coherence tomography of the anterior segment at 1310 nm." Archives of Ophthalmology 119(8): 1179-1185.
Reid, Brian J., "p53 and Neoplastic Progression in Barrett's Esophagus", The American Journal of Gastroenterology, 2001, 96(5):1321-1323.
Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," Optics Letters, vol. 27, No. 19, Oct. 1, 2002, pp. 1702-1704.
Richards-Kortum et al., "Spectral diagnosis of atherosclerosis using an optical fiber laser catheter", American Heart Journal, 1989, 118(2):381-391.
Ripley, P. M., et al., "A comparison of Artificial Intelligence techniques for spectral classification in the diagnosis of human pathologies based upon optical biopsy", Journal of Optical Society of America, 2000, pp. 217-219.
Rogers, A. J. (1981). "Polarization-Optical Time Domain Reflectometry: A Technique for the Measurement of Field Distributions." Applied Optics 20(6): 1060-1074.
Rollins et al., "In vivo video rate optical coherence tomography," Optics Express, vol. 3, pp. 219-229, Sep. 1998.
Rollins, A. M., R. Ung-arunyawee, et al. (1999). "Real-time in vivo imaging of human gastrointestinal ultrastructure by use of endoscopic optical coherence tomography with a novel efficient interferometer design." Optics Letters 24(19): 1358-1360.
Rollins, A.M. and J. A. Izatt (1999). "Optimal interferometer designs for optical coherence tomography." Optics Letters 24(21): 1484-1486.
Rollins, A.M., S. Yazdanfar, et al. (2000). "Imaging of human retinal hemodynamics using color Doppler optical coherence tomography." Investigative Ophthalmology & Visual Science 41(4): S548-S548.
Rollins, A.M., S. Yazdanfar, et al. (2002). "Real-time in vivo color Doppler optical coherence tomography." Journal of Biomedical Optics 7(1): 123-129.
Roth, Jonathan E. et al., "Simplified Method for Polarization-Sensitive Optical Coherence Tomography," Optics Letters, vol. 26, No. 14, Jul. 15, 2001, pp. 1069-1071.
Ruth, B., "Blood Flow Determination by the Laser Speckle Method", International Journal of Microcirculation, Clinical and Experimental, 1990, 9(1):21-45.
Sadhwani, Ajay et al., "Determination of Teflon thickness with laser speckle I. Potential for burn depth diagnosis," Optical Society of America, 1996, vol. 35, No. 28, pp. 5727-5735.
Salunke, N. V., et al., "Biomechanics of Atherosclerotic Plaque" Critical Reviews™, Biomedical Engineering, 1997, 25(3):243-285.
Hitzenberger, C. K., M. Sticker, et al. (2001). "Differential phase measurements in low-coherence interferometry without 2 pi ambiguity." Optics Letters 26(23): 1864-1866.
Hitzenberger, Christopher K. et al., "Measurement and Imaging of Birefringence and Optic Axis Orientation by Phase Resolved Polarization Sensitive Optical Coherence Tomography," Optics Express, vol. 9, No. 13, Dec. 17, 2001, pp. 780-790.
Hoeling, B. M., A. D. Fernandez, et al. (2000). "An optical coherence microscope for 3-dimensional imaging in developmental biology." Optics Express 6(7): 136-146.
Hoerauf, H., C. Scholz, et al. (2002). "Transscleral optical coherence tomography: a new imaging method for the anterior segment of the eye." Archives of Opthalmology 120(6): 816-819.
Hoffmann, K., M. Happe, et al. (1998). "Optical coherence tomography (OCT) in dermatology." Journal of Investigative Dermatology 110(4): 583-583.
Hoh, S. T., D. S. Greenfield, et al. (2000). "Optical coherence tomography and scanning laser polarimetry in normal, ocular hypertensive, and glaucomatous eyes." American Journal of Opthalmology 129(2): 129-135.
Hohenleutner, U., M. Hilbert, et al. (1995). "Epidermal Damage and Limited Coagulation Depth with the Flashlamp-Pumped Pulsed Dye Laser: a Histochemical Study." Journal of investigative Dermatology 104(5): 798-802.
Holland, A. J. A., H. C. O. Martin, et al. (2002). "Laser Doppler imaging prediction of burn wound outcome in children." Burns 28(1): 11-17.
Hotate Kazuo et at., "Optical Coherence Domain Reflectometry by Synthesis of Coherence Function," Journal of Lightwave Technology, vol. 11, pp. 1701-1710, Oct. 1993.
Hotate, K. and T. Okugawa (1994). "Optical Information Processing by Synthesis of the Coherence Function." Journal of Lightwave Technology 12(7): 1247-1255.
Hourdakis, C. J. and A. Perris (1995). "A Monte Carlo Estimation of Tissue Optical Properties for Use in Laser Dosimetry." Physics in Medicine and Biology 40(3): 351-364.

(56) References Cited

OTHER PUBLICATIONS

Hrabovsky, M., "Theory of speckle dispacement and decorrelation: application in mechanics", SPIE, 1998, 3479:345-354.

Hu, Z., F. Li, et al. (2000). "Wavelength-tunable narrow-linewidth semiconductor fiber-ring laser." IEEE Photonics Technology Letters 12(8): 977-979.

Huang, D. et al., "Optical Coherence Tomography," Science, vol. 254, pp. 1178-1181, Nov. 1991.

Huang, F., W. Yang, et al. (2001). "Quadrature spectral interferometric detection and pulse shaping." Optics Letters 26(6): 382-384.

Huang, X. R. and R. W. Knighton (2002). "Linear birefringence of the retinal nerve fiber layer measured in vitro with a multispectral imaging micropolarimeter." Journal of Biomedical Optics 7(2): 199-204.

Huang, Xiang-Run et al.,"Variation of Peripapillary Retinal Nerve Fiber Layer Birefringence in Normal Human Subjects," Investigative Ophthalmology & Visual Science, vol. 45, No. 9, Sep. 2004, pp. 3073-3080.

Huber, R., M. Wojtkowski, et al. (2005). "Amplified, frequency swept lasers for frequency domain reflectometry and OCT imaging: design and scaling principles." Optics Express 13(9): 3513-3528.

Hunter, D. G., J. C. Sandrock, et al. (1999). "Mathematical modeling of retinal birefringence scanning." Journal of the Optical Society of America A 16(9): 2103-2111.

Hurwitz, H. H. and R. C. Jones (1941). "A new calculus for the treatment of optical systems II. Proof of three general equivalence theorems." Journal of the Optical Society of America 31(7): 493-499.

Huttner, B., B. Gisin, et al. (1999). "Distributed PMD measurement with a polarization-OTDR in optical fibers." Journal of Lightwave Technology 17(10): 1843-1848.

Huttner, B., C. De Barros, et al. (1999). "Polarization-induced pulse spreading in birefringent optical fibers with zero differential group delay." Optics Letters 24(6): 370-372.

Huttner, B., J. Reecht, et al. (1998). "Local birefringence measurements in single-mode fibers with coherent optical frequency-domain reflectometry." IEEE Photonics Technology Letters 10(10): 1458-1460.

Hyde, S.C. W., N. P. Barry, et al. (1995). "Depth-Resolved Holographic Imaging through Scattering Media by Photorefraction." Optics Letters 20(11): 1331-1333.

Hyde, S.C. W., N. P. Barry, et al. (1995). "Sub-100-µm Depth-Resolved Holographic Imaging through Scattering Media in the near Infrared." Optics Letters 20(22): 2330-2332.

Iftimia, N. V., B. E. Bouma, et al. (2004). "Adaptive ranging for optical coherence tomography." Optics Express 12(17): 4025-4034.

Iftimia, Nicusor V. et al., "A portable, low coherence interferometry based instrument for tine needle aspiration biopsy guidance," Review of Scientific Instruments, vol. 76, Issue 6, (2005).

Iida, T., N. Hagimura, et al. (2000). "Evaluation of central serous chorioretinopathy with optical coherence tomography." American Journal of Ophthalmology 129(1): 16-20.

Imai, M., H. lijima, et al. (2001). "Optical coherence tomography of tractional macular elevations in eyes with proliferative diabetic retinopathy." Am J Ophthalmol. 32(3):458-461.

Indebetouw, G. and P. Klysubun (2000). "Imaging through scattering media with depth resolution by use of low-coherence gating in spatiotemporal digital holography." Optics Letters 25(4): 212-214.

Inoue, Kyo et al., "Nearly Degenerate Four-Wave-Mixing in a Traveling-Wave Semiconductor Laser Amplifier," Applied Physics Letters, vol. 51, pp. 1051-1053, 1987.

Ip, M. S., B. J. Baker, et al. (2002). "Anatomical outcomes of surgery for idiopathic macular hole as determined by optical coherence tomography." Archives of Ophthalmology 120(1): 29-35.

Ishikawa, Hiroshi, et al., "Macular Segmentation with optical coherence tomography", Investigative Ophthalmology & Visual Science, 2005, 46(6):2012-2017.

Ismail, R., V. Tanner, et al. (2002). "Optical coherence tomography imaging of severe commotio retinae and associated macular hole." British Journal of Ophthalmology 86(4): 473-474.

Ivanov, A. P. et al., "Interferometric Study of the Spatial Structure of a Light-Scattering Medium," Journal of Applied Spectroscopy, vol. 28, pp. 359-364, 1978.

Ivanov, A. P. et al., "New Method for High-Range Resolution Measurements of Light Scattering in Optically Dense Inhomogeneous Media," Optics Letters, vol. 1, pp. 226-228, Dec. 1977.

Izatt, J. A., M. R. Hee, et al. (1994). "Micrometer-scale resolution imaging of the anterior eye in vivo with optical coherence tomography." Archives of Opthalmology 112(12): 1584-9.

Izatt, J. A., M. R. Hee et al. (1994). "Optical Coherence Microscopy in Scattering Media." Optics Letters 19(8): 590-592.

Izatt, J. A., M.D. Kulkarni, et al. (1996). "Optical coherence tomography and microscopy in gastrointestinal tissues." IEEE Journal of Selected Topics in Quantum Electronics 2(4): 1017-1028.

Izatt, J. A., M.D. Kulkarni, et al. (1997). "In vivo bidirectional color Doppler flow imaging of picoliter blood volumes using optical coherence tomography." Optics Letters 22(18): 1439-1441.

Jacques, S. L., J. R. Roman, et al. (2000). "Imaging superficial tissues with polarized light." Lasers in Surgery and Medicine 26(2): 119-129.

Jacques, S. L., J. S. Nelson, et al. (1993). "Pulsed Photothermal Radiometry of Port-Wine-Stain Lesions." Applied Optics 32(13): 2439-2446.

Jacques, Steven L., "Role of Tissue Optics and Pulse Duration on Tissue Effects During High-Power Laser Irradiation", Applied Optics, 1993, 32(13):2447-2454.

Jang, I. K., B. D. MacNeill, et al. (2002). "In-vivo characterization of coronary plaques in patients with ST elevation acute myocardial infarction using optical coherence tomography (OCT)." Circulation 106(19): 698-698.

Jang, I. K., B. E. Bouma, et al. (2002). "Visualization of coronary atherosclerotic plaques in patients using optical coherence tomography: Comparison with intravascular ultrasound." Journal of the American College of Cardiology 39(4): 604-609.

Jeng, J. C., A. Bridgeman, et al. (2003). "Laser Doppler imaging determines need for excision and grafting in advance of clinical judgment: a prospective blinded trial." Burns 29(7): 665-670.

Jerath, Maya R., et al., "Calibrated Real-Time Control of Lesion Size Based on Reflectance Images", Applied Optics, 1993, 32(7):1200-1209.

Jerath, Maya R., et al., "Dynamic Optical Property Changes: Implications for Reflectance Feedback Control of Photocoagulation", Journal of Photochem. Photobiol. B: Biol., 1992, 16:113-126.

Jesser, C. A., S. A. Boppart, et al. (1999). "High resolution imaging of transitional cell carcinoma with optical coherence tomography: feasibility for the evaluation of bladder pathology." British Journal of Radiology 72: 1170-1176.

U.S. Office Action issued for U.S. Appl. No. 11/288,994 dated Dec. 18, 2007.

U.S. Office Action issued for U.S. Appl. No. 11/410,937 dated Jan. 10, 2008.

U.S. Office Action issued for U.S. Appl. No. 11/435,228 dated Jan. 10, 2008.

U.S. Office Action issued for U.S. Appl. No. 11/445,990 dated Jan. 11, 2008.

U.S. Office Action issued for U.S. Appl. No. 11/534,095 dated Oct. 11, 2007.

U.S. Office Action issued for U.S. Appl. No. 11/670,069 dated Oct. 30, 2007.

Abbas, G.L., V.W.S. Chan et al., "Local-Oscillator Excess-Noise Suppression for Homodyne and Heterodyne-Detection," Optics Letters, vol. 8, pp. 419-421, Aug. 1983 issue.

Acioli, L. H., et al. (1991) "Femtosecond Temporal Encoding in Barium-Titanate," Optics Letters 16(24): 1984-1986.

Adams, S. B., Jr. et al., "The use of polarization sensitive optical coherence tomography and elastography to assess connective tissue", In Conference on Lasers and Electro-Optics, 2003, CLEO'03, 2002, p. 3.

Adrain, A. L., et al., "High-Resolution Endoluminal Sonography is a Sensitive Modality for the Identification of Barrett's Metaplasia", Gastrointestinal Endoscopy, 1997, 46(2):147-151.

(56) References Cited

OTHER PUBLICATIONS

Agrawal, G.P., "Population Pulsations and Nondegenerate Four-Wave Mixing in Semiconductor-Lasers and Amplifiers," Journal of the Optical Society of America B, vol. 5, pp. 147-159, Jan. 1998.
Aigouy, L., et al. (1999) "Polarization effects in apertureless scanning near-field optical microscopy: an experimental study," Optics Letters 24(4): 187-189.
Akiba, M., et al. (2003) "Full-field optical coherence tomography by two-dimensional heterodyne detection with a pair of CCD cameras." Optics Letters 28(10):816-818.
Akiba, Masahiro et al., "En-face optical coherence imaging for three-dimensional microscopy", SPIE, 2002, pp. 8-15.
Akkin, T., et al. (2002) "Phase-sensitive measurement of birefringence change as an indication of neural functionality and diseases," Lasers in Surgery and Medicine, pp. 6-6.
Akkin, T., et al. (2003) "Surface analysis using phase sensitive optical low coherence reflectometry." Lasers in Surgery and Medicine, pp. 4-4.
Akkin, T., et al. (2004) "Detection of neural activity using phase-sensitive optical low-coherence reflectometry." Optics Express, 12(11):2377-2386.
Anderson, R. Rox, et al., "Selective Photothermolysis: Precise Microsurgery by Selective Absorption of Pulsed Radiation", Science, 1983, 220(4596):524-527.
Andretzky, P. et al., "Optical Coherence Tomography by Spectral Radar: Improvement of Signal-to-Noise Ratio," The International Society for Optical Engineering, USA, vol. 3915, pp. 55-59, 2000.
Andretzky, P., et al. (1999) "Optical coherence tomography by 'spectral radar': Dynamic range estimation and in vivo measurements of skin." Proceedings of SPIE—The International Society for Optical Engineering 3567, pp. 78-87.
Antcliff, R. J., et al. (2000) "Comparison between optical coherence tomography and fundus fluorescein angiography for the detection of cystoid macular edema in patients with uveitis," Ophthalmology, 107(3): 593-599.
Antcliff, R. J., et al. (2000) "Optical coherence tomography of melanocytoma," American Journal of Ophthalmology 130(6):845-847.
Anvari, B., et al. (1995) "A Theoretical Study of the Thermal Response of Skin to Cryogen Spray Cooling and Pulsed-Laser Irradiation: Implications for Treatment of Port-Wine Stain Birthmarks," Physics in Medicine and Biology 40(9): 1451-1465.
Anvari, B., T. E. Milner, et al. (1995). "Selective Cooling of Biological Tissues: Application for Thermally Mediated Therapeutic Procedures." Physics in Medicine and Biology 40(2):241-252.
Arend, O., et al. (2000) "Macular circulation in patients with diabetes mellitus with and without arterial hypertension." British Journal of Opthalmology 84(12):1392-1396.
Arimoto, H., et al. (1997) "Measurements of the complex degree of spectral coherence by use of a wave-front-folded Interferometer," Optics Letters 22(13):958-960.
Arnaud, Dubois, et al., "Ultrahigh-resolution OCT using white-light interference microscopy", Proceedings of SPIE, 2003, vol. 4956, pp. 14-21.
Azzolini C., et al. (2001) "Correlation between optical coherence tomography data and biomicroscopic interpretation of idiopathic macular hole." American Journal of Ophthalmology 132(3):348-355.
Baba, T., K. Ohno-Matsui, eta!. (2002). "Optical coherence tomography of choroidal neovascularization in high myopia," Acta Ophthalmol. Scand. 80(1):82-87.
Bail, M.A.H., et al. (1996) "Optical coherence tomography with the "spectral radar": fast optical analysis in volume scatterers by short coherence interferometry." In BIOS Europe '96, pp. 298-303, International Society for Optics and Photonics, 1996.
Ballif, J. et al., "Rapid and Scalable Scans at 21 m/s in optical Low-Coherence Reflectometry," Optics Letters, vol. 22, pp. 757-759, Jun. 1997.

Baney, D. M., et al. (1993) "Extended-Range Optical Low-Coherence Reflectometry Using a Recirculating Delay Technique," IEEE Photonics Technology Letters 5(9):1109-1112.
Baney, D. M., et al. (2002) "Coherent optical spectrum analyzer." IEEE Photonics Technology Letters, 14(3):355-357.
Barakat, R. (1981) "Bilinear Constraints between Elements of the 4×4 Mueller-Jones Transfer-Matrix of Polarization Theory," Optics Communications 38(3):159-161.
Barakat, R. (1993) "Analytic Proofs of the Arago-Fresnel Laws for the Interference of Polarized Light," Journal of the Optical Society of America A, 10(1):180-185.
Barakat, Richard, "Statistics of the Stokes Parameters," J. Opt. Soc. Am. A, vol. 4, No. 7, Jul. 1987, pp. 1256-1263.
Barbastathis, G., et al. (1999) "Multidimensional tomographic imaging using volume holography," Proceedings of the IEEE 87(12):2098-2120.
Bardal, S., et al. (1992) "Photoinduced Birefringence in Optical Fibers: A Comparative Study of Low-Birefringence and High-Birefringence Fibers," Optics Letters 17(6):411-413.
Barfuss H. et al., "Modified Optical Frequency-Domain Reflectometry with High Spatial-Resolution for Components of Integrated Optic Systems," Journal of Lightwave Technology, vol. 7, pp. 3-10, Jan. 1989.
Barr, H., et al., "Endoscopic Therapy for Barrett's Oesophagus", Gut, 2005, 54:875-884.
Barsky, S. H., et al. (1980) "The Nature and Evolution of Port Wine Stains: A Computer-Assisted Study," Journal of Investigative Dermatology 74(3):154-157.
Barton, J. K., et al. (1998) "Investigating pulsed dye laser-blood vessel interaction with color Doppler optical coherence tomography," Optics Express 3(6):251.
Barton, J. K., et al. (1999) "Three-dimensional reconstruction of blood vessels from in vivo color Doppler optical coherence tomography images," Dermatology 198(4):355-361.
Barton, J. K., et al. (2001) "Photothermal coagulation of blood vessels: a comparison of high-speed optical coherence tomography and numerical modelling," Physics in Medicine and Biology 46:1665-1678.
Bashkansky, M. et al., "Signal processing for improving field cross-correlation function in optical coherence tomography," vol. 37, Issue 34, pp. 8137-8138 (1998).
Bashkansky, M., et al. (1997) "Subsurface defect detection in ceramics by high-speed high-resolution optical coherent tomography," Optics Letters 22(1):61-63.
Bashkansky, M., et al. (2000) "Statistics and reduction of speckle in optical coherence tomography," Optics Letters 25(8):545-547.
Baumgartner, A., et al. (1998) "Signal and resolution enhancements in dual beam optical coherence tomography of the human eye," Journal of Biomedical Optics 3(1):45-54.
Baumgartner, A., et al. (2000) "Polarization-sensitive optical coherence tomography of dental structures." Caries Research 34(1):59-69.
Sampliner, Richard E., "Endoscopic Ablative Therapy for Barrett's Esophagus: Current Status", Gastrointestinal Endoscopy, 2004, 59(1):66-69.
Sampliner, Richard E., et al., "Reversal of Barrett's Esophagus with Acid Suppression and Multipolar Electrocoagulation: Preliminary Results", Gastrointestinal Endoscopy, 1996, 44(5):532-535.
Sandoz, P. (1997). "Wavelet transform as a processing tool in white-light interferometry." Optics Letters 22(14): 1065-1067.
Sankaran, V., J. T. Walsh, et al. (2000). "Polarized light propagation through tissue phantoms containing densely packed scatterers." Optics Letters 25(4): 239-241.
Sankaran, V., M. J. Everett, et al. (1999). "Comparison of polarized-light propagation in biological tissue and phantoms." Optics Letters 24(15): 1044-1046.
Sarunic, M. V., M.A. Choma, et al. (2005). "Instantaneous complex conjugate resolved spectral domain and swept-source OCT using 3×3 fiber couplers." Optics Express 13(3): 957-967.
Sathyam, U. S., B. W. Colston, et al. (1999). "Evaluation of optical coherence quantitation of analytes in turbid media by use of two wavelengths." Applied Optics 38(10): 2097-2104.

(56) References Cited

OTHER PUBLICATIONS

Saxer et al., "High-speed fiber-based polarization-sensitive optical coherence tomography of in vivo human skin," Optical Society of America, vol. 25, pp. 1355-1357, Sep. 2000.
Schmitt, J. M. (1997). "Array detection for speckle reduction in optical coherence microscopy." Physics in Medicine and Biology 42(7): 1427-1439.
Schmitt, J. M. (1999). "Optical coherence tomography (OCT): A review." IEEE Journal of Selected Topics in Quantum Electronics 5(4): 1205-1215.
Schmitt, J. M. and A. Knuttel (1997). "Model of optical coherence tomography of heterogeneous tissue." Journal of the Optical Society of America A 14(6): 1231-1242.
Schmitt, J. M. et al, "Measurement of Optical Properties of Biological Tissues by Low-Coherence Reflectometry," Applied Optics, vol. 32, pp. 6032-6042, Oct. 1993.
Schmitt, J. M., et al., "Speckle in Optical Coherence Tomography: An Overview", SPIE, 1999, vol. 3726, pp. 450-461.
Schmitt, J. M., M. J. Yadlowsky, et al. (1995). "Subsurface Imaging of Living Skin with Optical Coherence Microscopy." Dermatology 191(2): 93-98.
Schmitt, J. M., S. H. Xiang, et al. (1998). "Differential absorption imaging with optical coherence tomography." Journal of the Optical Society of America A 15(9):2288-2296.
Schmitt, J. M., S. H. Xiang, et al. (1999). "Speckle in optical coherence tomography." Journal of Biomedical Optics 4(1): 95-105.
Schmitt, J. M., S. L. Lee, et al. (1997). "An optical coherence microscope with enhanced resolving power in thick issue." Optics Communications 142(4-6): 203-207.
Schmitt, J.M. et al., "Cross-Polarized Backscatter in Optical Coherence Tomography of Biological Tissue," Optics Letters, vol. 23, No. 13, Jul. 1, 1998, pp. 1060-1062.
Schmitt, M. Joseph, et al., "OCT elastography: imaging microscopic deformation and strain of tissue", Optics Express, 1998, 3(6):199-211.
Schoenenberger, Klaus et al., "Mapping of Birefringence and Thermal Damage in Tissue by use of Polarization-Sensitive Optical Coherence Tomography," Applied Optics, vol. 37, No. 25, Sep. 1, 1998, pp. 6026-6036.
Sennaroglu, Alphan, et al., "Efficient Continuous-Wave Chromium-Doped YAG Laser", Journal of Optical Society of America B, 1995, 12(5):930-937.
Shapo, et al., "Intravascular strain imaging: Experiments on an Inhomogeneous Phantom", IEEE Ultrasonics Symposium 1996, 2:1177-1180.
Shapo, et al., "Ultrasonic displacement and strain imaging of coronary arteries with a catheter array", IEEE Ultrasonics Symposium 1995, 2:1511-1514.
Sharma, P. et al., "Magnification Chromoendoscopy for the Detection of Intestinal Metaplasia and Dysplasia in Barrett's Oesophagus", Gut, 2003, 52:24-27.
Shi, H., I. Nitta, et al. (1999). "Demonstration of phase correlation in multiwavelength mode-locked semiconductor diode lasers." Optics Letters 24(4): 238-240.
Shi, H., J. Finlay, et al. (1997). "Multiwavelength 10-GHz picosecond pulse generation from a single-stripe semiconductor diode laser." IEEE Photonics Technology Letters 9(11): 1439-1441.
Shribak, Michael et al., "Techniques for Fast and Sensitive Measurements of Two-Dimensional Birefringence Distributions," Applied Optics, vol. 42, No. 16, Jun. 1, 2003, pp. 3009-3017.
Silberberg, Y. et al., "Passive-Mode Locking of a Semiconductor Diode-Laser," Optics Letters, vol. 9, pp. 507-509, Nov. 1984.
Simon, R. (1982). "The Connection between Mueller and Jones Matrices of Polarization Optics." Optics Communications 42(5): 293-297.
Smith, L. Montgomery et al., "Absolute Displacement Measurements Using Modulation of the Spectrum of White Light in a Michelson Interferometer," Applied Optics, vol. 28, pp. 3339-3342, Aug. 1989.
Smith, P., et al. (2002). "Variable-Focus Microlenses as a Potential Technology for Endoscopy." Proc SPIE, vol. 3919, pp. 187-192.
Smithies, D. J., T. Lindmo, et al. (1998). "Signal attenuation and localization in optical coherence tomography studied by Monte Carlo simulation." Physics in Medicine and Biology 43(10): 3025-3044.
Soetikno, Roy M., et al., "Endoscopic Mucosal resection", Gastrointestinal Endoscopy, 2003, 57(4):567-579.
Somervell, A.R.D. et al., "Direct Measurement of Fringe Amplitude and Phase Using a Heterodyne Interferometer Operating in Broadband Light," Optics Communications, 2004, 229(1):59-64.
Sonehara, Tsuyoshi, et al. (1995). "Forced Brillouin Spectroscopy Using Frequency-Tunable Continuous Wave Lasers", Physical Review Letters 75(23): 4234-4237.
Sonnenschein, C. M. et al., "Signal-To-Noise Relationships for Coaxial Systems that Heterodyne Backscatter from Atmosphere," Applied Optics, vol. 10, pp. 1600-1604, Jul. 1971.
Sorin, W. V. and D. F. Gray (1992). "Simultaneous Thickness and Group Index Measurement Using Optical Low-Coherence Reflectometry." IEEE Photonics Technology Letters 4(1): 105-107.
Sorin, W. V. et al., "A Simple Intensity Noise-Reduction Technique for Optical Low-Coherence Reflectometry," IEEE Photonics Technology Letters, vol. 4, pp. 1404-1406, Dec. 1992.
Sorin, W. V. et al., "Measurement of Rayleigh Backscattering at 1.55 µm with 32 µm Spatial Resolution," IEEE Photonics Technology Letters, vol. 4, pp. 374-376, Apr. 1992.
Spechler, Stuart Jon, "Barrett's Esophagus: Should We Brush off this Ballooning Problem?" Gastroenterology, 1997, 112(6):2138-2142.
Srinivas, Shyam M. et al., "Determination of Burn Depth by Polarization-Sensitive Optical Coherence Tomography," Journal of Biomedical Optics, vol. 9, No. 1, Jan./Feb. 2004, pp. 207-212.
Stewart. C. J. et al., "A comparison of two laser-based methods for determination of burn scar perfusion: laser Doppler versus laser speckle imaging," Elsevier Ltd, 2005, vol. 31, pp. 744-752.
Sticker, M., C. K. Hitzenberger, et al. (2001). "Quantitative differential phase measurement and imaging in transparent and turbid media by optical coherence tomography." Optics Letters 26(8): 518-520.
Sticker, M., M. Pircher, et al. (2002). "En face imaging of single cell layers by differential phase contrast optical coherence microscopy." Optics Letters 27(13): 1126-1128.
Stifter, D. et al., "Polarisation-Sensitive Optical Coherence Tomography for Material Characterisation and Strain-Field Mapping," Applied Physics A, 76, Jan. 2003, pp. 947-951.
Stoller, P., et al. (2002). "Polarization-dependent optical second-harmonic imaging of a rat-tail tendon." Journal of Biomedical Optics 7(2): 205-214.
Strasswimmer, John et al., "Polarization-Sensitive Optical Coherence Tomography of Invasive Basal Cell Carcinoma," Journal of Biomedical Optics, vol. 9, No. 2, Mar./Apr. 2004, pp. 292-298.
Sun, C. S. (2003). "Multiplexing of fiber-optic acoustic sensors in a Michelson interferometer configuration." Optics Letters 28(12): 1001-1003.
Swanson, E. A. et al., "High-Speed Optical Coherence Domain Reflectometry," Optics Letters, vol. 17, pp. 151-153, Jan. 1992.
Swanson, E. A., J. A. Izatt, et al. (1993). "In-Vivo Retinal Imaging by Optical Coherence Tomography." Optics Letters 18(21): 1864-1866.
EP European Patent Office Search Report for European Application No. 01991092.6-2305 dated Jan. 12, 2006.
EP European Patent Office Search Report for European Application No. 05791226.3, dated Nov. 20, 2007.
JP Notice of Reasons for Rejection and English translation for Japanese Application No. 2002-538830, dated Jul. 14, 2006.
PCT International Search Report for International Application No. PCT/US2001/049704, dated Dec. 10, 2002.
PCT International Search Report and Written Opinion for International Application No. PCT/US2004/023585 dated Aug. 28, 2006.
PCT International Preliminary Report on Patentability for International Application No. PCT/US2004/038404 dated Jun. 2, 2006.
PCT International Search Report for International Application No. PCT/US2004/039454, dated May 11, 2005.

(56) References Cited

OTHER PUBLICATIONS

PCT International Written Opinion for international Application No. PCT/US2004/039454, dated May 11, 2005.
PCT International Search Report for International Application No. PCT/US2005/023664, dated Oct. 12, 2005.
PCT International Written Opinion for International Application No. PCT/US2005/023664, dated Oct. 12, 2005.
PCT International Search Report for International Application No. PCT/US2005/030294, dated Aug. 22, 2006.
PCT International Search Report for International Application No. PCT/US2005/039740, dated Feb. 21, 2006.
PCT International Written Opinion for International Application No. PCT/US2005/039740, dated Feb. 21, 2006.
PCT International Preliminary Report on Patentability for International Application No. PCT/US2005/043951 dated Jun. 7, 2007.
PCT International Search Report for International Application No. PCT/US2005/043951, dated Apr. 6, 2006.
PCT International Written Opinion for International Application No. PCT/US2005/043951, dated Apr. 6, 2006.
PCT Statement under Article 19 and Reply to PCT Written Opinion for International Application No. PCT/US2005/043951 dated Jun. 6, 2006.
PCT International Search Report for International Application No. PCT/US2006/016677 filed Apr. 28, 2006.
PCT International Written Opinion for International Application No. PCT/US2006/016677 filed Apr. 28, 2006.
PCT International Search Report for International Application No. PCT/US2006/018865 filed May 5, 2006.
PCT International Written Opinion for International Application No. PCT/US2006/018865 filed May 5, 2006.
PCT International Search Report and Written Opinion for International Application No. PCT/US2006/031905 dated May 3, 2007.
PCT International Search Report and Written Opinion for International Application No. PCT/US2007/060319 dated Jun. 6, 2007.
PCT International Search Report and Written Opinion for International Application No. PCT/US2007/060481 dated May 23, 2007.
PCT International Search Report and Written Opinion for International Application No. PCT/US2007/060657 dated Aug. 13, 2007.
PCT International Search Report and Written Opinion for International Application No. PCT/US2007/060670 dated Sep. 21, 2007.
PCT International Search Report and Written Opinion for International Application No. PCT/US2007/060717 dated May 24, 2007.
PCT International Search Report for International Application No. PCT/US2007/060787 dated Mar. 18, 2008.
PCT International Search Report and Written Opinion for International Application No. PCT/US2007/061463 dated Jan. 23, 2008.
PCT International Search Report and Written Opinion for International Application No. PCT/US2007/061481 dated Mar. 17, 2008.
PCT International Search Report and Written Opinion for International Application No. PCT/US2007/061815 dated Aug. 2, 2007.
PCT International Search Report and Written Opinion for International Application No. PCT/US2007/062465 dated Aug. 8, 2007.
PCT International Search Report and Written Opinion for International Application No. PCT/US2007/066017 dated Aug. 30, 2007.
PCT International Search Report for International Application No. PCT/US2007/068233 dated Feb. 21, 2008.
PCT International Search Report and Written Opinion for International Application No. PCT/US2007/078254 dated Mar. 28, 2008.
U.S. Office Action issued for U.S. Appl. No. 09/709,162 dated Nov. 20, 2006.
U.S. Office Action issued for U.S. Appl. No. 09/709,162 dated Oct. 9, 2007.
U.S. Office Action issued for U.S. Appl. No. 10/137,749 dated Aug. 24, 2006.
U.S. Office Action issued for U.S. Appl. No. 10/406,751 dated May 23, 2007.
U.S. Office Action issued for U.S. Appl. No. 10/501,268 dated Nov. 13, 2006.
U.S. Office Action issued for U.S. Appl. No. 10/501,276 dated Dec. 18, 2006.
U.S. Office Action issued for U.S. Appl. No. 10/551,735 dated May 23, 2007.
U.S. Office Action issued for U.S. Appl. No. 10/997,789 dated Aug. 10, 2007.
U.S. Office Action issued for U.S. Appl. No. 10/997,789 dated Dec. 6, 2006.
U.S. Office Action issued for U.S. Appl. No. 10/997,789 dated Jan. 3, 2008.
U.S. Office Action issued for U.S. Appl. No. 11/174,425 dated Feb. 2, 2007.
U.S. Notice of Allowance issued for U.S. Appl. No. 11/225,840 dated Oct. 3, 2007.
U.S. Office Action issued for U.S. Appl. No. 11/241,907 dated Mar. 28, 2007.
U.S. Office Action issued for U.S. Appl. No. 11/264,655 dated Dec. 21, 2007.
U.S. Office Action issued for U.S. Appl. No. 11/285,301 dated Nov. 15, 2007.
Youngquist, Robert C. et al., "Optical Coherence-Domain Reflectometry: A New Optical Evaluation Technique," Optics Letters, vol. 12, pp. 158-160, Mar. 1987.
Yu, P., et al. "Imaging of tumor necroses using full-frame optical coherence imaging", Proceedings of SPIE, 2003, vol. 4956, pp. 34-41.
Yun, S. H. et al., "Interrogation of Fiber Grating Sensor Arrays with a Wavelength-Swept Fiber Laser," Optics Letters, vol. 23, pp. 843-845, Jun. 1998.
Yun, S. H. et al., "Wavelength-Swept Fiber Laser with Frequency Shifted Feedback and Resonantly Swept Intra-Cavity Acoustooptic Tunable Filter," IEEE Journal of Selected Topics in Quantum Electronics, vol. 3, pp. 1087-1096, Aug. 1997.
Yun, S. H., C. Boudoux, et al. (2003). "High-speed wavelength-swept semiconductor laser with a polygon-scanner-based wavelength filter." Optics Letters 28(20): 1981-1983.
Yun, S. H., C. Boudoux, et al. (2004). "Extended-cavity semiconductor wavelength-swept laser for biomedical Imaging." IEEE Photonics Technology Letters 16(1): 293-295.
Yun, S. H., G. J. Tearney, et al. (2004). "Motion artifacts in optical coherence tomography with frequency-domain ranging." Optics Express 12(13): 2977-2998.
Yun, S. H., G. J. Tearney, et al. (2004). "Pulsed-source and swept-source spectral-domain optical coherence tomography with reduced motion artifacts." Optics Express 12(23): 5614-5624.
Yun, S. H., G. J. Tearney, et al. (2004). "Removing the depth-degeneracy in optical frequency domain imaging with frequency shifting." Optics Express 12(20): 4822-4828.
Yun, S.H. et al., "High-Speed Optical Frequency-Domain Imaging," Optics Express, vol. 11, No. 22, Nov. 3, 2003, pp. 2953-2963.
Yun, S.H. et al., "High-Speed Spectral-Domain Optical Coherence Tomography at 1.3 μm Wavelength," Optics Express, vol. 11, No. 26, Dec. 29, 2003, pp. 3598-3604.
Yung, K. M., "Phase-Domain Processing of Optical Coherence Tomography Images," Journal of Biomedical Optics, vol. 4, pp. 125-136, Jan. 1999.
Zhang Jun et al., "Full range polarization-sensitive Fourier domain optical coherence tomography", Optics Express, 2004, 12(24):6033-6039.
Zhang J., J. S. Nelson, et al. (2005). "Removal of a mirror image and enhancement of the signal-to-noise ratio in Fourier-domain optical coherence tomography using an electro-optic phase modulator." Optics Letters 30(2): 147-149.
Zhang, Jun et al., "Determination of Birefringence and Absolute Optic Axis Orientation Using Polarization-Sensitive Optical Coherence Tomography with PM Fibers," Optics Express, vol. 11, No. 24, Dec. 1, 2003, pp. 3262-3270.
Zhang, Y., M. Sato, et al. (2001). "Numerical investigations of optimal synthesis of several low coherence sources for resolution improvement." Optics Communications 192(3-6): 183-192.
Zhang, Y., M. Sato, et al. (2001). "Resolution improvement in optical coherence tomography by optimal synthesis of light-emitting diodes." Optics Letters 26(4): 205-207.

(56) References Cited

OTHER PUBLICATIONS

Zhao Y. H., Z. P. Chen, et al. (2000). "Doppler standard deviation imaging for clinical monitoring of in vivo human skin blood flow." Optics Letters 25(18): 1358-1360.

Zhao, Y. H., Z. P. Chen, et al. (2000). "Phase-resolved optical coherence tomography and optical Doppler tomography for imaging blood flow in human skin with fast scanning speed and high velocity sensitivity." Optics Letters 25(2): 114-116.

Zhao Y., et al., "Three-dimensional reconstruction of in vivo blood vessels in human skin using phase-resolved optical Doppler tomography", IEEE Journal of Selected Topics in Quantum Electronics, 2001, 7(6):931-935.

Zhao, Y., Z. Chen, et al. (2002). "Real-time phase-resolved functional optical coherence tomography by use of optical Hilbert transformation." Optics Letters 27(2): 98-100.

Zhou, D., P. R. Prucnal, et al. (1998). "A widely tunable narrow linewidth semiconductor fiber ring laser." IEEE Photonics Technology Letters 10(6): 781-783.

Zhou, Xiao-Qun et al., "Extended-Range FMCW Reflectometry Using an optical Loop with a Frequency Shifter," IEEE Photonics Technology Letters, vol. 8, pp. 248-250, Feb. 1996.

Zimnyakov, D. A., et al., "A study of statistical properties of partially developed speckle fields as applied to the diagnostics of structural changes in human skin", Optics and Spectroscopy, 1994, 76(5):747-753.

Zimnyakov, D. A., et al., "Spatial speckle correlometry in applications to tissue structure monitoring", Applied Optics 1997, 36(22):5594-5607.

Zimnyakov, D. A., et al., "Speckle patterns polarization analysis as an approach to turbid tissues structure monitoring", SPIE 1999, 2981:172-180.

Zimnyakov, Dmitry A., et al., "Speckle-Contrast Monitoring of Tissue Thermal Modification", Applied Optics, 2002, 41(28):5989-5996.

Zorabedian, Paul et al., "Tuning Fidelity of Acoustooptically Controlled External Cavity Semiconductor Lasers," Journal of Lightwave Technology, vol. 13, pp. 62-66, Jan. 1995.

Zuluaga, A. F. and R. Richards-Kortum (1999). "Spatially resolved spectral interferometry for determination of subsurface structure." Optics Letters 24(8): 519-521.

Zumbusch, A., et al. (1999). "Three-dimensional vibrational imaging by coherent anti-Stokes Raman scattering", Physical Review Letters 82(20): 4142-4145.

Zvyagin, A. V., J. B. FitzGerald, et al. (2000). "Real-time detection technique for Doppler optical coherence tomography." Optics Letters 25(22): 1645-1647.

PCT International Search Report and Written Opinion for International Application No. PCT/US2013/065549 dated Mar. 20, 2014.

Razansky, Nika R. et al, Double-cladding-fiber-based detection system for intravascular mapping of fluorescent molecular probes. Progress in biomedical optics and imaging, 2011, vol. 12, No. 12, abstract.

Wang, X. J., T. E. Milner, et al. (1997). "Measurement of fluid-flow-velocity profile in turbid media by the use of optical Doppler tomography." Applied Optics 36(1): 144-149.

Wang, Xiao-Jun et at., "Characterization of Dentin and Enamel by Use of Optical Coherence Tomography," Applied Optics, vol. 38, No. 10, Apr. 1, 1999, pp. 2092-2096.

Wang, Xueding et al., "Propagation of Polarized Light in Birefringent Turbid Media: Time-Resolved Simulations," Optics Express, vol. 9, No. 5, 2001, pp. 254-259.

Wang, Y. M., J. S. Nelson, et al. (2003). "Optimal wavelength for ultrahigh-resolution optical coherence tomography." Optics Express 11(12): 1411-1417.

Wang, Y. M., Y. H. Zhao, et al. (2003). "Ultrahigh-resolution optical coherence tomography by broadband continuum generation from a photonic crystal fiber." Optics Letters 28(3): 182-184.

Watkins, L R., S.M. Tan, et al. (1999). "Determination of interferometer phase distributions by use of wavelets." Optics Letters 24(13): 905-907.

Webb, RH, et al. (1987). "Confocal Scanning Laser Ophthalmoscope", Applied Optics 26(8): 1492-1499.

Welzel, J. (2001). "Optical coherence tomography in dermatology: a review." Skin Research and Technology 7(1): 1-9.

Wentworth, R. H. (1989). "Theoretical Noise Performance of Coherence-Multiplexed Interferometric Sensors." Journal of Lightwave Technology 7(6): 941-956.

Westphal, V., A.M. Rollins, et al. (2002). "Correction of geometric and refractive image distortions in optical coherence tomography applying Fermat's principle." Optics Express 10(9): 397-404.

Westphal, V., S. Yazdanfar, et al. (2002). "Real-time, high velocity-resolution color Doppler optical coherence tomography." Optics Letters 27(1): 34-36.

Whelan, W.M. et al., "A novel Strategy for Monitoring Laser Thermal Therapy Based on Changes in Optothermal Properties of Heated Tissues", International Journal of Thermophysics, 2005, 26(1):233-241.

White, Brian R. et al., "In Vivo Dynamic Human Retinal Blood Flow Imaging Using Ultra-High-Speed Spectral Domain Optical Doppler Tomography," Optics Express, vol. 11, No. 25, Dec. 15, 2003, pp. 3490-3497.

Williams, P. A. (1999). "Rotating-wave-plate Stokes polarimeter for differential group delay measurements of polarization-mode dispersion." Applied Optics 38(31): 6508-6515.

Wojtkowski, M., A. Kowalczyk, et al. (2002). "Full range complex spectral optical coherence tomography technique in eye imaging." Optics Letters 27(16): 1415-1417.

Wojtkowski, M., R. Leitgeb, et al. (2002). "Fourier domain OCT imaging of the human eye in vivo." Proc. SPIE 4619: 230-236.

Wojtkowski, M., R. Leitgeb, et al. (2002). "In vivo human retinal imaging by Fourier domain optical coherence tomography." Journal of Biomedical Optics 7(3): 457-463.

Wojtkowski, M., T. Bajraszewski, et al. (2003). "Real-time in vivo imaging by high-speed spectral optical coherence tomography." Optics Letters 28(19): 1745-1747.

Wojtkowski, M., V. J. Srinivasan, et al. (2004). "Ultrahigh-resolution, high-speed, Fourier domain optical coherence tomography and methods for dispersion compensation." Optics Express 12(11): 2404-2422.

Wong, B. J. F., Y. H. Zhao, et al. (2004). "Imaging the internal structure of the rat cochlea using optical coherence tomography at 0.827 µm and 1.3 µm." Otolaryngology Head and Neck Surgery 130(3): 334-338.

Wong, Brian J.F. et al., "Optical Coherence Tomography of the Rat Cochlea," Journal of Biomedical Optics, vol. 5, No. 4, Oct. 2000, pp. 367-370.

Wussling, M., et al., "Laser diffraction and speckling studies in skeletal and heart muscle", Biomed. Biochim. Acta, 1986, 45(1/2):S23-S27.

Wysocki, P.F. et al., "Broad-Spectrum, Wavelength-Swept, Erbium-Doped Fiber Laser at 1.55 µm," Optics Letters, vol. 15, pp. 879-881, Aug. 1990.

Yabushita, H. B., et al. (2002). "Measurement of Thin Fibrous Caps in Atherosclerotic Plaques by Optical Coherence Tomography." American Heart Association, Inc., Circulation 106:1640.

Yamanari, M. et al., "Polarization sensitive Fourier domain optical coherence tomography with continuous polarization modulation", Proc. of SPIE, 2006, vol. 6079, p. 60792A-1.

Yang, C. H., A. Wax, et al. (2000). "Interferometric phase-dispersion microscopy." Optics Letters 25(20): 1526-1528.

Yang, C., A. Wax, et al. (2001). "Phase-dispersion optical tomography." Optics Letters 26(10): 686-688.

Yang, C., A. Wax, et al. (2001). "Phase-referenced interferometer with subwavelength and subhertz sensitivity applied to the study of cell membrane dynamics." Optics Letters 26(16): 1271-1273.

Yang, V. X. D., B. Qi, et al. (2003). "In vivo feasibility of endoscopic catheter-based Doppler optical coherence tomography." Gastroenterology 124(4): A49-A50.

Yang, V. X. D., M. L. Gordon, et al. (2003). "High speed, wide velocity dynamic range Doppler optical coherence tomography (Part 1): System design, signal processing, and performance." Optics Express 11 (7): 794-809.

(56) References Cited

OTHER PUBLICATIONS

Yang, V. X. D., M. L. Gordon, et al. (2003). "High speed, wide velocity dynamic range Doppler optical coherence tomography (Part II): Imaging in vivo cardiac dynamics of Xenopus laevis." Optics Express 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." Optics Express 11(19): 2416-2424.

Yang, V. X. D., M. L. Gordon, et at. (2002). "Improved phase-resolved optical Doppler tomography using the Kasai velocity estimator and histogram segmentation." Optics Communications 208(4-6): 209-214.

Yang, Ying et al., "Observations of Birefringence in Tissues from Optic-Fibre-Based Optical Coherence Tomography," Measurement Science and Technology, Nov. 2003, pp. 41-46.

Yao, G. and L. H. V. Wang (2000). "Theoretical and experimental studies of ultrasound-modulated optical tomography in biological tissue." Applied Optics 39(4): 659-664.

Yao, Gang et al., "Propagation of Polarized Light in Turbid Media: Simulated Animation Sequences," Optics Exgress, vol. 7, No. 5, Aug. 28, 2000, pp. 198-203.

Yao, Gang et al., "Two-Dimensional Depth-Resolved Mueller Matrix Characterization of Biological Tissue by Optical Coherence Tomography," Optics Letters, Apr. 15, 1999, vol. 24, No. 8, pp. 537-539.

Yasuno, Y. et al., "Birefringence Imaging of Human Skin by Polarization-Sensitive Spectral Interferometric Optical Coherence Tomography," Optics Letters, vol. 27, No. 20, Oct. 15, 2002 pp. 1803-1805.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.

Yazdanfar, S. and J. A. Izatt (2002). "Self-referenced Doppler optical coherence tomography." Optics Letters 27(23): 2085-2087.

Yazdanfar, S., A.M. Rollins, et al. (2000). "Imaging and velocimetry of the human retinal circulation with color Doppler optical coherence tomography." Optics Letters 25(19): 1448-1450.

Yazdanfar, S., A.M. Rollins, et al. (2000). "Noninvasive imaging and velocimetry of human retinal blood flow using color Doppler optical coherence tomography" Investigative Ophthalmology & Visual Science 41(4): S548-S548.

Yazdanfar, S., A.M. Rollins, et al. (2003). "In vivo imaging of human retinal flow dynamics by color Doppler optical coherence tomography." Archives of Ophthalmology 121 (2): 235-239.

Yazdanfar, S., C. H. Yang, et al. (2005). "Frequency estimation precision in Doppler optical coherence tomography using the Cramer-Rao lower bound." Optics Express 13(2): 410-416.

Yazdanfar, S., et al., "In Vivo imaging in blood flow in human retinal vessels using color Doppler optical coherence tomography", SPIE, 1999, vol. 3598, pp. 177-184.

Yazdanfar, S., M. D. Kulkarni, et al. (1997). "High resolution imaging of in vivo cardiac dynamics using color Doppler optical coherence tomography." Optics Express 1(13): 424-431.

Yelin, D., et al., "Double-clad Fiber for Endoscopy", Optical Letters, 2005, 29(20):2408-2410.

Yelin, D., et al., "Three-dimensional imaging using spectral encoding heterodyne interferometry", Optics Letters, 2005, 30(14):1794-1796.

Ymeti, A., et al., "Integration ofmicrofluidics with a four-channel integrated optical Young interferometer immunosensor", Biosensors and Bioelectronics, 2005, 20:1417-1421.

Yoshimura, T., et al., "Statistical properties of dynamic speckles", J. Opt. Soc. Am A. 1986, 3(7):1032-1054.

Akkin, T., et al. (2003). "Imaging tissue response to electrical and photothermal stimulation with nanometer sensitivity," Lasers in Surgery and Medicine 33(4):219-225.

M. M. Gualini, W. A. Kha, W. Sixt and H. Steinbichler, "Recent advancements of optical interferometry applied to medicine," Proceedings. IEEE International Multi Topic Conference, 2001. IEEE INMIC 2001. Technology for the 21st Century., Lahore, Pakistan, 2001, pp. 205-211. doi: 10.1109/INMIC.2001.995338.

Jang, I. K., G. J. Tearney, et al. (2000). "Comparison of optical coherence tomography and intravascular ultrasound for detection of coronary plaques with large lipid-core in living patients." Circulation 102(18): 509-509.

Pitris et al., "Ultrahigh-resolution in-vivo versus ex-vivo OCT imaging and tissue preservation", Proc. SPIE vol. 4251, 2001, pp. 170-173.

Okugawa, T. and K. Rotate (1996). "Real-time optical image processing by synthesis of the coherence function using real-time holography." IEEE Photonics Technology Letters 8(2): 257-259.

Randall, John, et al., "Brillouin scattering in systems of biological significance [and discussion]", Philosophical Transactions of the Royal Society of London A: Mathematical, Physical and Engineering Sciences, 1979, 293(1402):341-348.

Dettwiller, L. (1997). "Polarization state interference: A general investigation." Pure and Applied Optics 6(1): 41-53.

Devesa, Susan S., et al., "Changing Patterns in the Incidence of Esophegeal and Gastric Carcinoma in the United States." American Cancer Society, 1998, 83(10):2049-2053.

DiCarlo, C. D., W. P. Roach, et al. (1999). "Comparison of optical coherence tomography imaging of cataracts with histopathology." Journal of Biomedical Optics 4(4): 450-458.

Ding, Z., Y. Zhao, et al. (2002). "Real-time phase-resolved optical coherence tomography and optical Doppler tomography." Optics Express 10(5): 236-245.

Dobrin, P. B. (1996). "Effect of histologic preparation on the cross-sectional area of arterial rings." Journal of Surgical Research 61(2): 413-5.

Donohue, D. J., B. J. Stoyanov, et al. (1995). "Numerical Modeling of the Corneas Lamellar Structure and Birefringence Properties." Journal of the Optical Society of America A 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." Physics in Medicine and Biology 44(4): 967-981.

Dorrer, C. et al., "Spectral Resolution and Sampling Issues in Fourier-Transform Spectral Interferometry," Journal of the Optical Society of America B, vol. 17, pp. 1795-1802, Oct. 2000.

Drexler, W., A. Baumgartner, et al. (1997). "Biometric investigation of changes in the anterior eye segment during accommodation." Vision Research 37(19): 2789-2800.

Drexler, W. et al., "In vivo ultrahigh-resolution optical coherence tomography," Optics Letters, vol. 24, pp. 1221-1223, Sep. 1999.

Drexler, W., A. Baumgartner, et al. (1997). "Submicrometer precision biometry of the anterior segment of the human eye." Investigative Ophthalmology & Visual Science 38(7): 1304-1313.

Drexler, W., A. Baumgartner, et al. (1998). "Dual beam optical coherence tomography: signal identification for ophthalmologic diagnosis." Journal of Biomedical Optics 3 (1): 55-65.

Drexler, W., C. K. Hitzenberger, et al. (1995). "Measurement of the Thickness of Fundus Layers by Partial Coherence Tomography." Optical Engineering 34(3): 701-710.

Drexler, W., C. K. Hitzenberger, et al. (1996). "(Sub)micrometer precision biometry of the human eye by optical coherence tomography and topography." Investigative Opthalmology & Visual Science 37(3): 4374-4374.

Drexler, W., C. K. Hitzenberger, et al. (1998). "Investigation of dispersion effects in ocular media by multiple wavelength partial coherence interferometry." Experimental Eye Research 66(1): 25-33.

Drexler, W., D. Stamper, et al. (2001). "Correlation of collagen organization with polarization sensitive imaging of in vitro cartilage: implications for osteoarthritis." Journal of Rheumatology 28(6): 1311-1318.

Drexler, W., et al., "Ultrahigh-resolution optical coherence tomography", Journal of Biomedical Optics, 2004, 9(1):47-74.

Drexler, W., H. Sattmann, et al. (2003). "Enhanced visualization of macular pathology with the use of ultrahigh-resolution optical coherence tomography." Archives of Ophthalmology 121(5): 695-706.

(56) References Cited

OTHER PUBLICATIONS

Drexler, W., U. Morgner, et al. (2001). Ultrahigh-resolution ophthalmic optical coherence tomography, Errata—Nature Medicine 7(5):636.
Drexler, W., U. Morgner, et al. (2001). "Ultrahigh-resolution ophthalmic optical coherence tomography." Nature Medicine 7(4): 502-507.
Drexler, W.O. Findl, et al. (1997). "Clinical feasibility of dual beam optical coherence topography and tomography for ophthalmologic diagnosis." Investigative Opthalmology & Visual Science 38(4): 1038.
Drexler, W.O. Findl, et al. (1998). "Partial coherence interferometry: A novel approach to biometry in cataract surgery." American Journal of Opthalmology 126(4): 524-534.
Droog, E. J., W.,. Steenbergen, et. al. (2001). "Measurement of depth of burns by laser Doppler perfusion imaging." Burns 27(6): 561-568.
Dubois, A., K. Grieve, et al. (2004). "Ultrahigh-resolution full-field optical coherence tomography." Applied Optics 43(14): 2874-2883.
Dubois, A., L. Vabre, et al. (2002). "High-resolution full-field optical coherence tomography with a Linnik microscope." Applied Optics 41(4): 805-812.
Ducros, M., M. Laubscher, et al. (2002). "Parallel optical coherence tomography in scattering samples using a two-dimensional smart-pixel detector array." Optics Communications 202(1-3): 29-35.
Ducros, M.G., J.D. Marsack, et al. (2001). "Primate retina imaging with polarization-sensitive optical coherence tomography." Journal of the Optical Society of America A 18(12): 2945-2956.
Ducros, Mathieu G. et al., "Polarization Sensitive Optical Coherence Tomography of the Rabbit Eye," IEEE Journal of Selected Topics in Quantum Electronics, vol. 5, No. 4, Jul./Aug. 1999, pp. 1159-1167.
Dudley, J.M. et al., "Cross-Correlation Frequency Resolved Optical Gating Analysis of Broadband Continuum Generation in Photonic Crystal Fiber: Simulations and Experiments," Optics Express, vol. 10, p. 1215, Oct. 2002.
Duncan, A., J. H. Meek, et al. (1995). "Optical Pathlength Measurements on Adult Head, Calf and Forearm and the Head of the Newborn Infant Using Phase Resolved Optical Spectroscopy." Physics in Medicine and Biology 40(2): 295-304.
Eickhoff, W. et al., "Optical Frequency Domain Reflectometry in Single-Mode Fiber," Applied Physics Letters, vol. 39, pp. 693-695, 1981.
Eigensee A., G. Haeusler, et al. (1996). "A New method of short-coherence interferometry in human skin (in vivo) and in solid volume scatterers." Proceedings of SPIE—The International Society for Optical Engineering 2925: 169-178.
Eisenbeiss, W., J. Marotz, et al. (1999). "Reflection-optical multispectral imaging method for objective determination of burn depth." Burns 25(8): 697-704.
Elbaum, M., M. King, et al. (1972). "Wavelength-Diversity Technique for Reduction of Speckle Size." Journal of the Optical Society of America 62(5): 732-737.
Elliott, K. H., et al., "The use of commercial CCD cameras as linear detectors in the physics undergraduate teaching laboratory", European Journal of Physics, 1998, 19:107-117.
Erdelyi, M., et al. "Generation of diffraction-free beams for applications in optical microlithography", J. Vac. Sci. Technol. B, 1997, 15(2):287-292.
Ervin, J. C., H. G. Lemij, et al. (2002). "Clinician change detection viewing longitudinal stereophotographs compared to confocal scanning laser tomography in the LSU Experimental Glaucoma (LEG) Study." Ophthalmology 109(3): 467-481.
Escobar, P. F., et al., "Diagnostic efficacy of optical coherence tomography in the management of preinvasive and invasive cancer of uterine cervix and vulva", Int. Journal of Gynecological Cancer, 2004, 14:470-474.
Essenpreis, M., C. E. Elwell, et al. (1993). "Spectral Dependence of Temporal Point Spread Functions in Human Tissues." Applied Optics 32(4): 418-425.

Eun, H. C. (1995). "Evaluation of skin blood flow by laser Doppler flowmetry." Clinics in Dermatology 13(4): 337-347.
Evans, J. A., et al., "Optical Coherence Tomography to Identify Intramucosal Carcinoma and High-Grade Dysplasia in Barrett's Esophagus", Clinical Gastroenterology and Hepatology, 2006, 4:38-43.
Evans, J. A., J. M. Poneros, et al. (2004). "Application of a histopathologic scoring system to optical coherence tomography (OCT) images to identify high-grade dysplasia in Barrett's esophagus." Gastroenterology 126(4): A51-A51.
Everett, M.J. et al., "Birefringence Characterization of Biological Tissue by Use of Optical Coherence Tomography," Optics Letters, vol. 23, No. 3, Feb. 1, 1998, pp. 228-230.
Facchini, M., et al., "An endoscopic system for DSPI", Optik, 1993, 95(1):27-30.
Falk, Gary W., et al., "Surveillance of Patients with Barrett's Esophagus for Dysplasia and Cancer with Ballon Cytology" Gastroenterology, 1997, 112:1787-1797.
Feldchtein, F. I., G. V. Gelikonov, et al. (1998). "Endoscopic applications of optical coherence tomography." Optics Express 3(6): 257-270.
Feldchtein, F. I., G. V. Gelikonov, et al. (1998). "In vivo OCT imaging of hard and soft tissue of the oral cavity." Optics Express 3(6): 239-250.
Fercher, A. F., C. Hitzenberger, et al. (1991). "Measurement of Intraocular Optical Distances Using Partially Coherent Laser Light." Journal of Modern Optics 38(7): 1327-1333.
Fercher, A. F., C. K. Hitzenberger, et al. (1993). "In Vivo Optical Coherence Tomography." American Journal of Opthalmology 116(1): 113-115.
Fercher, A. F., C. K. Hitzenberger, et al. (1994). "In vivo dual beam optical coherence tomography." Proceedings of SPIE, vol. 2083, pp. 356-362.
Fercher, A. F., C. K. Hitzenberger, et al. (1995). "Measurement of Intraocular Distances by Backscattering Spectral Interferometry." Optics Communications 117(1-2): 43-48.
Fercher, A. F., C. K. Hitzenberger, et al. (1996). Ocular partial coherence interferometry. Proceedings of SPIE, vol. 2732, pp. 210-228.
Fercher, A. F., C. K. Hitzenberger, et al. (2000). "A thermal light source technique for optical coherence tomography." Optics Communications 185(1-3): 57-64.
Fercher, A. F., C. K. Hitzenberger, et al. (2002). "Dispersion compensation for optical coherence tomography depth-scan signals by a numerical technique." Optics Communications 204(1-6): 67-74.
Fercher, A. F., C.K. Hitzenberger, et al. (2001). "Numerical dispersion compensation for Partial Coherence Interferometry and Optical Coherence Tomography." Optics Express 9(12): 610-615.
Fercher, A. F., H. C. Li, et al. (1993). "Slit Lamp Laser-Doppler Interferometer." Lasers in Surgery and Medicine 13(4): 447-452.
Fercher, A. F., K. Mengedoht, et al. (1988). "Eye-Length Measurement by Interferometry with Partially Coherent Light." Optics Letters 13(3): 186-188.
Fercher, A. F., W. Drexler, et al. (1994). Measurement of optical distances by optical spectrum modulation. Proceedings of SPIE, vol. 2083, pp. 263-267.
Fercher, A. F., W. Drexler, et al. (1997). "Optical ocular tomography." Neuro-Ophthalmology 18(2): 39-49.
Fercher, A. F., W. Drexler, et al. (2003). "Optical coherence tomography—principles and applications." Reports on Progress in Physics 66(2): 239-303.
Fercher, Adolf "Optical Coherence Tomography," Journal of Biomedical Optics, vol. I, pp. 157-173, Apr. 1996.
Fernandez, D. C., et al., "Automated detection of retinal layer structures on optical coherence tomography images", Optics Express, 2005, 13(25):10200-10216.
Ferreira, L.A. et al., "Polarization-Insensitive Fibre-Optic White-Light Interferometry," Optics Communications, vol. 114, pp. 386-392, Feb. 1995.
Ferro, P., M. Haelterman, et al. (1991). "All-Optical Polarization Switch with Long Low-Birefringence Fiber." Electronics Letters 27(16): 1407-1408.

(56) References Cited

OTHER PUBLICATIONS

Fetterman, M. R., D. Goswami, et al. (1998). "Ultrafast pulse shaping: amplification and characterization." Optics Express 3(10): 366-375.
Findl, O., W. Drexler, et al. (2001). "Improved prediction of intraocular lens power using partial coherence interferometry." Journal of Cataract and Refractive Surgery 27(6): 861-867.
Fork, R. L., C. H. B. Cruz, et al. (1987). "Compression of Optical Pulses to 6 Femtoseconds by Using Cubic Phase Compensation." Optics Letters 12(7): 483-485.
Foschini, G. J. and C. D. Poole (1991). "Statistical Theory of Polarization Dispersion in Single Mode Fibers." Journal of Lightwave Technology 9(11): 1439-1456.
Francia, C., F. Bruyere, et al. (1998). "PMD second-order effects on pulse propagation in single-mode optical fibers." IEEE Photonics Technology Letters 10(12): 1739-1741.
French, P.M.W., et al., "Continuous-wave Mode-Locked CR4+: YAG Laser", Optics Letters, 1993, 18(1):39-41.
Fried, D., R. E. Glena, et al. (1995). "Nature of Light-Scattering in Dental Enamel and Dentin at Visible and near-Infrared Wavelengths." Applied Optics 34(7): 1278-1285.
Fried, Daniel et at., "Imaging Caries Lesions and Lesion Progression with Polarization Sensitive Optical Coherence Tomography," Journal of Biomedical Optics, vol. 7, No. 4, Oct. 2002, pp. 618-627.
Froehly, L. et al., "Multiplexed 3D Imaging Using Wavelength Encoded Spectral Interferometry: A Proof of Principle" Optics Communications, 2003, 222:127-136.
Fu, D., et al., "Non-invasive quantitative reconstruction of tissue elasticity using an iterative forward approach", Phys. Med. Biol., 2000, (45):1495-1509.
Fujii, Yohji, "High-Isolation Polarization-Independent Optical Circulator", Journal of Lightwave Technology, vol. 9, pp. 1238-1243, Oct. 1991.
Fujimoto, J. G. et al., "High resolution in vivo intra-arterial imaging with optical coherence tomography," Official Journal of the British Cardiac Society, vol. 82, pp. 128-133 Heat, 1999.
Fujimoto, J. G., M. E. Brezinski, et al. (1995). "Optical Biopsy and Imaging Using Optical Coherence Tomography" Nature Medicine 1(9): 970-972.
Fukasawa, A. and H. Iijima (2002). "Optical coherence tomography of choroidal osteoma." American Journal of Ophthalmology 133(3): 419-21.
Fymat, A. L. (1981). "High-Resolution Interferometric Spectrophotopolarimetry." Optical Engineering 20(1): 25-30.
Galtarossa, A., L. Palmieri, et al. (2000). "Measurements of beat length and perturbation length in long single-mode fibers." Optics Letters 25(6): 384-386.
Gandjbakhche, A. H., P. Mills, et al. (1994). "Light-Scattering Technique for the Study of Orientation and Deformation of Red Blood Cells in a Concentrated Suspension." Applied Optics 33(6): 1070-1078.
Ganz, Robert A., et al., "Complete Ablation of Esophageal Epithelium with a Balloon-based Bipolar Electrode: A Phased Evaluation in the Porcine and in the Human Esophagus", Gastrointestinal Endoscopy, 2004, 60(6):1002-1010.
Garcia, N. and M. Nieto-Vesperinas (2002). "Left-handed materials do not make a perfect lens." Physical Review Letters 88(20): 207403-1 thru 207403-4.
Gelikonov, V. M., G. V. Gelikonov, et al. (1995). "Coherent Optical Tomography of Microscopic Inhomogeneities in Biological Tissues." JETP Letters 61(2): 158-162.
Georgakoudi, I., et al., "Fluorescence, Reflectance, and Light-Scattering Spectroscopy for Evaluating Dysplasia in Patients with Barrett's Esophagus", Gastroenterology, 2001, 120:1620-1629.
George, N. and A. Jain (1973). "Speckle Reduction Using Multiple Tones of illumination" Applied Optics 12(6): 1202-1212.
Gibson, G. N., R. Klank, et al. (1996). "Electro-optically cavity-dumped ultrashort-pulse Ti:sapphire oscillator." Optics Letters 21(14): 1055-1057.

Gil, J. J. (2000). "Characteristic properties of Mueller matrices." Journal of the Optical Society of America A 17(2): 328-334.
Gil, J. J. et al., (1987) "Obtainment of the polarizing and retardation parameters of a non-depolarizing optical system from the polar decomposition of its Mueller matrix," Optik, 76(2): 67-71.
Gladkova, N.D., G. A. Petrova, et al. (2000). "In vivo optical coherence tomography imaging of human skin: norm and pathology." Skin Research and Technology 6(1): 6-16.
Glaessl, A., A. G. Schreyer, et al. (2001). "Laser surgical planning with magnetic resonance imaging-based 3-dimensional reconstructions for intralesional Nd:YAG laser therapy of a venous malformation of the neck." Archives of Dermatology 137(10): 1331-1335.
Glance, B., "Polarization Independent Coherent Optical Receiver," Journal of Lightwave Technology, vol. LT-5, p. 274, Feb. 1987.
Gloesmann, M., B. Hermann, et al. (2003): "Histologic correlation of pig retina radial stratification with ultrahigh-resolution optical coherence tomography." Investigative Ophthalmology & Visual Science 44(4): 1696-1703.
Glombitza, U., "Coherent Frequency-Domain Reflectometry for Characterization of Single-Mode Integrated-Optical Wave-guides," Journal of Lightwave Technology, vol. 11, pp. 1377-1384, Aug. 1993.
Goldberg, L. and D. Mehuys (1994). "High-Power Superluminescent Diode Source." Electronics Letters 30(20): 1682-1684.
Goldsmith, J. A., Y. Li, et al. (2005). "Anterior chamber width measurement by high speed optical coherence tomography." Ophthalmology 112(2): 238-244.
Goldstein, L. E., J. A. Muffat, et al. (2003). "Cytosolic beta-amyloid deposition and supranuclear cataracts in lenses from people with Alzheimer's disease." Lancet 361 (9365): 1258-1265.
Golubovic, B. et al., "Optical Frequency-Domain Reflectometry Using Rapid Wavelength Tuning of a Cr4+:Forsterite Laser," Optics Letters, vol. 22, pp. 1704-1706, Nov. 1997.
Golubovic, B., B. E. Bouma, et al. (1996). "Thin crystal, room-temperature Cr4+:forsterite laser using near-infrared pumping." Optics Letters 21(24): 1993-1995.
Baumgartner, A., et al. (2000) "Resolution-improved dual-beam and standard optical coherence tomography: a comparison," Graefe's Archive for Clinical and Experimental Ophthalmology 238(5):385-392.
Beaud, P. et al., "Optical Reflectometry with Micrometer Resolution for the Investigation of Integrated Optical Devices," IEEE Journal of Quantum Electronics, vol. 25, pp. 755-759, Apr. 1989.
Beaurepaire, E., et al. (1999) "Combined scanning optical coherence and two-photon-excited fluorescence microscopy," Optics Letters 24(14):969-971.
Beaurepaire, E., et al. (1998) "Optical coherence microscope for the in-depth study of biological structures: System based on a parallel detection scheme," SPIE, vol. 3250, pp. 201.
Bechara, F. G., et al. (2004) "Histomorphologic correlation with routine histology and optical coherence tomography," Skin Research and Technology 10(3):169-173.
Bechmann, M., et al. (2000) "Central corneal thickness determined with optical coherence tomography in various types of glaucoma," British Journal of Ophthalmology 84(11):1233-1237.
Bek, T., et al. (2000) "Quantitative anomaloscopy and optical coherence tomography scanning in central serous chorioretinopathy," Acta Ophthalmologica Scandinavica 78(6):632-637.
Benoit, A.M., et al. (2001) "Linear dichroism of the retinal nerve fiber layer expressed with Mueller matrices," Applied Optics 40(4):565-569.
Berovic, N., et al., "Observation of Brillouin scattering from single muscle fibres", European Biophysics Journal, 1989, 17:69-74.
Bickel, William et al., "Stokes Vectors, Mueller Matrices, and Polarized Scattered Light," Am. J. Phys., vol. 53, No. 5, May 1985 pp. 468-478.
Bicout, D., et al. (1994) "Depolarization of Multiply Scattered Waves by Spherical Diffusers: Influence of the Size Parameter," Physical Review E 49(2):1767-1770.
Blanchot, L., et al. (1997) "Low-coherence in depth microscopy for biological tissues imaging: Design of a real time control system," In BIOS Europe '97, pp. 198-204, International Society for Optics and Photonics.

(56) References Cited

OTHER PUBLICATIONS

Blumenthal, E. Z., et al. (2000) "Reproducibility of nerve fiber layer thickness measurements by use of optical coherence tomography," Ophthalmology 107(12):2278-2282.
Blumenthal, E. Z., et al. (2001) "Assessment of the retinal nerve fiber layer in clinical trials of glaucoma neuroprotection," Survey of Ophthalmology 45(Suppl 3):S305-S312.
Boas, et al., "Diffusing temporal light correlation for burn diagnosis", SPIE, 1999, 2979:468-477.
Boppart, S. A., et al. (1998) "Intraoperative assessment of microsurgery with three-dimensional optical coherence tomography," Radiology 208:81-86.
Boppart, S. A., et al. (1996) "Imaging developing neural morphology using optical coherence tomography," Journal of Neuroscience Methods 70:65-72.
Boppart, S. A., et al. (1997) "Forward-imaging instruments for optical coherence tomography," Optics Letters 22(21):1618.
Boppart, S. A., et al. (1999) "High-resolution optical coherence tomography-guided laser ablation of surgical tissue," Journal of Surgical Research 82(2):275-284.
Bouma, B. E., et al. (1996) "Self-phase-modulated Kerr-lens mode-locked Cr:forsterite laser source for optical coherence tomography," Optics Letters 21(22):1839.
Bouma, B. E., et al. (1997) "Compact resonator designs for mode-locked solid-state lasers," Applied Physics B 65:213-220.
Bouma, B. E., et al. (1996) "Compact Kerr-lens mode-locked resonators," Optics Letters 21:134-136.
Bouma, B. E., et al. (1998) "Optical coherence tomographic imaging of human tissue at 1.55 µm and 1.81 µm using Er- and Tm-doped fiber sources," Journal of Biomedical Optics 3(1):76-79.
Bouma, B. E., et al. (2000) "High-resolution imaging of the human esophagus and stomach in vivo using optical coherence tomography," Gastrointestinal Endoscopy 51(4):467-474.
Bouma, B. E., et al. (2002) "Clinical imaging with optical coherence tomography," Academic Radiology 9(8):942-953.
Bouma, B. E., et al. (2003) "Evaluation of intracoronary stenting by intravascular optical coherence tomography," Heart 89 (3):317-320.
Bouma, B., et al., "High Resolution Optical Coherence Tomographic Imaging Using a Mode-Locked Ti:Al2O3 Laser Source", Optics Letters, 1995, 20(13):1486-1488.
Bouma, B., et al., "Hybrid Mode Locking of a Flash-Lamp-Pumped Ti:Al2O3 laser", Optics Letters, 1994, 19(22):1858-1860.
Bouma, Brett et al., "Power-Efficient Nonreciprocal Interferometer and Linear-Scanning Fiber-Optic Catheter for Optical Coherence Tomography," Optics Letters, vol. 24, pp. 531-533, Apr. 1999.
Bourquin, S., et al. (2001) "Optical coherence topography based on a two-dimensional smart detector array," Optics Letters 26(8):512-514.
Bourquin, S., V. Monterosso, et al. (2000). "Video-rate optical low-coherence reflectometry based on a linear smart detector array." Optics Letters 25(2): 102-104.
Bouzid, A., et al. (1995) "Fiber-optic four-detector polarimeter," Optics Communications 118(3-4):329-334.
Bowd, C., et al. (2000) "The retinal nerve fiber layer thickness in ocular hypertensive, normal, and glaucomatous eyes with optical coherence-tomography," Archives of Ophthalmology 118(1):22-26.
Bowd, C., et al. (2001) "Detecting early glaucoma by assessment of retinal nerve fiber layer thickness and visual function," Investigative Ophthalmology & Visual Science 42(9):1993-2003.
Bowd, C., et al. (2002) "Imaging of the optic disc and retinal nerve fiber layer: the effects of age, optic disc area, refractive error, and gender," Journal of the Optical Society of America A 19(1):197-207.
Brand, S., et al. (2000) "Optical coherence tomography in the gastrointestinal tract," Endoscopy 32(10):796-803.
Brezinski, M. E., et al. (1996) "Imaging of coronary artery microstructure (in vitro) with optical coherence tomography," American Journal of Cardiology 77(1):92-93.
Brezinski, M. E., et al. (1996) "Optical coherence tomography for optical biopsy—Properties and demonstration of vascular pathology," Circulation 93(6):1206-1213.
Brezinski, M. E., et al. (1997) "Assessing atherosclerotic plaque morphology: Comparison of optical coherence tomography and high frequency intravascular ultrasound," Heart 77(5):397-403.
Brezinski, M. E., et al. (1999) "Optical coherence tomography: high-resolution imaging in nontransparent tissue," IEEE Journal of Selected Topics in Quantum Electronics 5(4):1185-1192.
Briers, D.J., "Speckle fluctuations and biomedical optics: implications and applications", Optical Engineering, 1993, 32(2): 277-283.
Brink, H. B. K., et al. (1988) "Birefringence of the Human Foveal Area Assessed in vivo with Mueller-Matrix Ellipsometry," Journal of the Optical Society of America A 5(1):49-57.
Brinkman, Ralf, et al., "Analysis of Cavitation Dynamics During Pulsed Laser Tissue Ablation by Optical On-Line Monitoring", IEEE Journal of Selected Topics in Quantum Electronics, 1996, 2(4):826-835.
Brinkmeyer, E. et al., "Efficient Algorithm for Non-Equidistant Interpolation of Sampled Data," Electronics Letters, vol. 28, p. 693, Mar. 1992.
Brinkmeyer, E. et al., "High-Resolution OCDR in Dispersive Waveguides," Electronics Letters, vol. 26, pp. 413-414, Mar. 1990.
Brosseau, C., et al. (1994) "Entropy Production in Multiple-Scattering of Light by a Spatially Random Medium," Physical Review E 50(6):4997-5005.
Brown, Stanley B. et al., "The Present and Future Role of Photodynamic Therapy in Cancer Treatment", The Lancet Oncology, 2004, 5:497-508.
Burgoyne, C. F., et al. (2002) "Change detection in regional and volumetric disc parameters using longitudinal confocal scanning laser tomography," Ophthalmology 109(3):455-466.
Cameron, Brent D. et al., "Measurement and Calculation of the Two-Dimensional Backscattering Mueller Matrix of a Turbid Medium," Optics Letters, vol. 23, No. 7, Apr. 1998, pp. 485-487.
Candido, R. and T. J. Allen (2002). "Haemodynamics in microvascular complications in type 1 diabetes." Diabetes-Metabolism Research and Reviews 18(4): 286-304.
Gonzalez, S. and Z. Tannous (2002). "Real-time, in vivo confocal reflectance microscopy of basal cell carcinoma." Journal of the American Academy of Dermatology 47(6): 869-874.
Gordon, M. O. and M.A. Kass (1999). "The Ocular Hypertension Treatment Study: design and baseline description of the participants." Archives of Ophthalmology 117(5): 573-83.
Götzinger, Erich et al., "Measurement and Imaging of Birefringent Properties of the Human Cornea with Phase-Resolved, Polarization-Sensitive Optical Coherence Tomography," Journal of Biomedical Optics, vol. 9, No. 1, Jan./Feb. 2004, pp. 94-102.
Grayson, T. P ., J. R. Torgerson, et al. (1994). "Observation of a Nonlocal Pancharatnam Phase Shift in the Process of Induced Coherence without Induced Emission." Physical Review A 49(1): 626-628.
Greaney, M. J., D. C. Hoffman, et al. (2002). "Comparison of optic nerve imaging methods to distinguish normal eyes from those with glaucoma." Investigative Ophthalmology & Visual Science 43(1): 140-5.
Greenfield, D. S. et al. (2000) "Effect of corneal polarization axis on assessment of retinal nerve fiber layer thickness by scanning laser polarimetry," American Journal of Ophthalmology, 129(6): 715-722.
Greenfield, D. S., H. Bagga, et al. (2003). "Macular thickness changes in glaucomatous optic neuropathy detected using optical coherence tomography." Archives of Ophthalmology 121(1): 41-46.
Griffin, R. A., D. D. Sampson, et al. (1995). "Coherence Coding for Photonic Code Division Multiple Access Networks." Journal of Lightwave Technology 13(9): 1826-1837.
Groner, Warren et al., "Orthogonal Polarization Spectral Imaging: A New Method for Study of the Microcirculation," Nature Medicine, vol. 5 No. 10, Oct. 1999, pp. 1209-1213.
Guedes, V., et al. (2003). "Optical coherence tomography measurement of macular and nerve fiber layer thickness in normal and glaucomatous human eyes." Ophthalmology 110: 177-189.
Gueugniaud, P. Y., H. Carsin, et al. (2000). "Current advances in the initial management of major thermal burns." Intensive Care Medicine 26(7): 848-856.

(56) References Cited

OTHER PUBLICATIONS

Guido, S. and R. T. Tranquillo (1993). "A Methodology for the Systematic and Quantitative Study of Cell Contact Guidance in Oriented Collagen Gels-Correlation of Fibroblast Orientation and Gel Birefringence." Journal of Cell Science 105:317-331.
Guo, Bujin, et al., "Laser-based mid-infrared reflectance imaging of biological tissues", Optics Express, 2004, 12(1):208-219.
Guo, Shuguang et al., "Depth-Resolved Birefringence and Differential Optical Axis Orientation Measurements with Fiber-based Polarization-Sensitive Optical Coherence Tomography," Optics Letters, vol. 29, No. 17, Sep. 1, 2004, pp. 2025-2027.
Gurses-Ozden, R., H. Ishikawa, et al. (1999). "Increasing sampling density improves reproducibility of optical coherence tomography measurements." Journal of Glaucoma 8(4): 238-241.
Guzzi, R. (1998). "Scattering Theory from Homogeneous and Coated Spheres." pp. 1-11.
Haberland, U. B., Vladimir; Schmitt, Hans J. (1996). "Optical coherent tomography of scattering media using electrically tunable near-infrared semiconductor laser." Applied Optics Draft, Jul. 12, 1996.
Haberland, U. H. P. et al., "Chirp Optical Coherence Tomography of Layered Scattering Media," Journal of Biomedical Optics, vol. 3, pp. 259-266, Jul. 1998.
Haberland, U. R., et al. (1995) "Investigation of highly scattering media using near-infrared continuous wave tunable semiconductor laser." Proc. SPIE, 2389: 503-512.
Hale, G. M. and M. R. Querry (1973). "Optical Constants of Water in 200-nm to 200-µm Wavelength Region." Applied Optics 12(3): 555-563.
Hammer, D. X., R. D. Ferguson, et al. (2002). "Image stabilization for scanning laser ophthalmoscopy." Optics Express 10(26): 1542-1549.
Hammer, Daniel X. et al., "Spectrally Resolved White-Light Interferometry for Measurement of Ocular Dispersion," Journal of the Optical Society of America A, vol. 16, pp. 2092-2102, Sep. 1999.
Hara, T., Y. Ooi, et al. (1989). "Transfer Characteristics of the Microchannel Spatial Light Modulator." Applied Optics 28(22): 4781-4786.
Hariri, Lida P., et al. "Endoscopic Optical Coherence Tomography and Laser-Induced Fluorescence Spectroscopy in a Murine Colon Cancer Model", Lasers in Surgery and Medicine, 2006, 38:305-313.
Harland, C. C., S. G. Kale, et al. (2000). "Differentiation of common benign pigmented skin lesions from melanoma by high-resolution ultrasound." British Journal of Dermatology 143(2): 281-289.
Hartl, I., et al. (2001). "Ultrahigh-resolution optical coherence tomography using continuum generation in an air-silica microstructure optical fiber." Optics Letters 26(9): 608-610.
Harvey, K. C. et al., "External-Cavity Diode-Laser Using a Grazing-Incidence Diffraction Grating," Optics Letters, vol. 16, pp. 910-912, Jun. 1991.
Hassenstein, A., A. A. Bialasiewicz, et al. (2000). "Optical coherence tomography in uveitis patients." American Journal of Opthalmology 130(5): 669-670.
Hattenhauer, M.G., D. H. Johnson, et al. (1998). "The probability of blindness from open-angle glaucoma." Ophthalmology 105(11): 2099-2104.
Hausler, G., J. M. Herrmann, et al. (1996). "Observation of light propagation in volume scatterers with 10(11)-fold slow motion." Optics Letters 21(14): 1087-1089.
Hausler, Gerd et al.,"'Coherence Radar' and 'Spectral Radar' New Tools for Dermatological Diagnosis," Journal of Biomedical Optics, vol. 3, pp. 21-31, Jan. 1998.
Hazebroek, H. F. and A. A. Holscher (1973). "Interferometric Ellipsometry." Journal of Physics E: Scientific Instruments 6(9): 822-826.
Hazebroek, H. F. and W. M. Visser (1983). "Automated Laser Interferometric Ellipsometry and Precision Reflectometry." Journal of Physics E: Scientific Instruments 16(7): 654-661.
He, Z. Y., N. Mukohzaka, et al. (1997). "Selective image extraction by synthesis of the coherence function using two-dimensional optical lock-in amplifier with microchannel spatial light modulator." IEEE Photonics Technology Letters 9(4): 514-516.
Hee, M. R., C. A. Puliafito, et al. (1995). "Quantitative assessment of macular edema with optical coherence tomography." Archives of Ophthalmology 113(8): 1019-1029.
Hee, M. R., C. A. Puliafito, et al. (1998). "Topography of diabetic macular edema with optical coherence tomography." Ophthalmology 105(2): 360-370.
Hee, M. R., J. A. Izatt, et al. (1993). "Femtosecond Transillumination Optical Coherence Tomography." Optics Letters 18(12): 950-952.
Hee, M. R., J. A. Izatt, et al. (1995). "Optical coherence tomography of the human retina." Archives of Ophthalmology 113(3): 325-332.
Hee, Michael R. et al., "Polarization-Sensitive Low-Coherence Reflectometer for Birefringence Characterization and Ranging," Journal of the Optical Society of America B, vol. 9, p. 903-908, Jun. 1992.
Hellmuth, T. and M. Welle (1998). "Simultaneous measurement of dispersion, spectrum, and distance with a fourier transform spectrometer." Journal of Biomedical Optics 3(1): 7-11.
Hemenger, R. P. (1989). "Birefringence of a medium of tenuous parallel cylinders." Applied Optics 28(18): 4030-4034.
Henry, M. (1981 ). "Fresnei-Arago Laws for Interference in Polarized Light: Demonstration Experiment." American Journal of Physics 49(7): 690-691.
Herz, P.R., Y. Chen, et al. (2004). "Micromotor endoscope catheter for in vivo, ultrahigh-resolution optical coherence tomography." Optics Letters 29(19): 2261-2263.
Hirakawa, H., H. Iijima, et al. (1999). "Optical coherence tomography of cystoid macular edema associated with retinitis pigmentosa." American Journal of Ophthalmology 128(2): 185-191.
Hitzenberger, C. K. and A. F. Fercher (1999). "Differential phase contrast in optical coherence tomography." Optics Letters 24(9): 622-624.
Hitzenberger, C. K., A. Baumgartner, et al. (1994). "Interferometric Measurement of Corneal Thickness with Micrometer Precision." American Journal of Ophthalmology 118(4): 468-476.
Hitzenberger, C. K., A. Baumgartner, et al. (1998). "Dispersion induced multiple signal peak splitting in partial coherence interferometry." Optics Communications 154(4): 179-185.
Hitzenberger, C. K., A. Baumgartner, et al. (1999). "Dispersion effects in partial coherence interferometry: Implications for intraocular ranging." Journal of Biomedical Optics 4(1): 144-151.
Hitzenberger, C. K., M. Danner, et al. (1999). "Measurement of the spatial coherence of superluminescent diodes." Journal of Modern Optics 46(12): 1763-1774.

\* cited by examiner

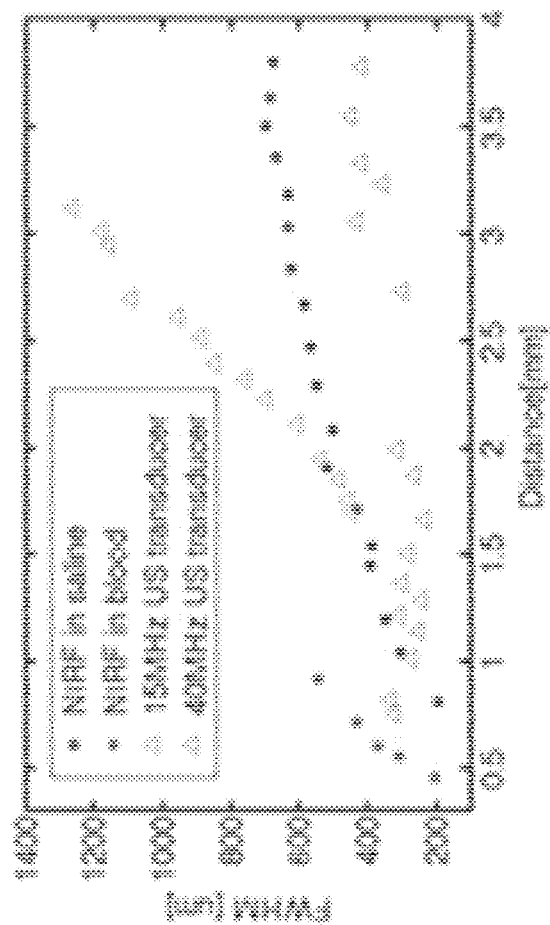
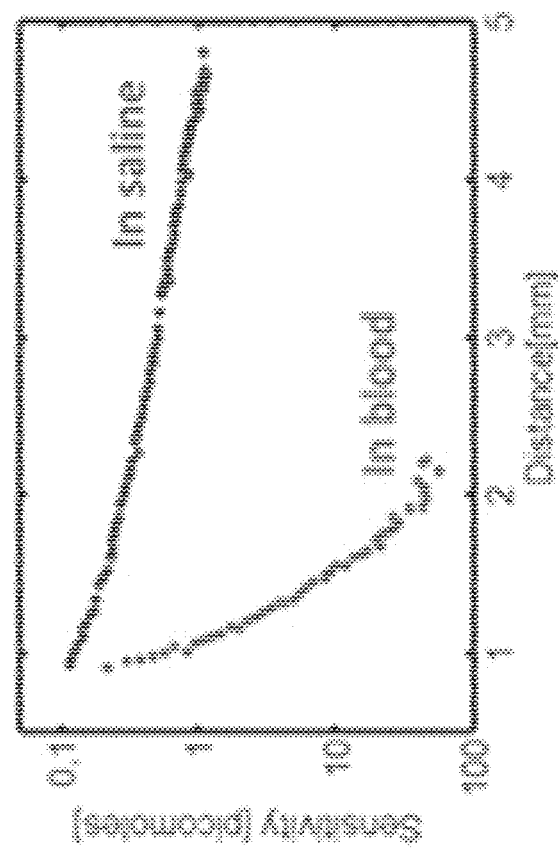
FIG. 4A
FIG. 4B

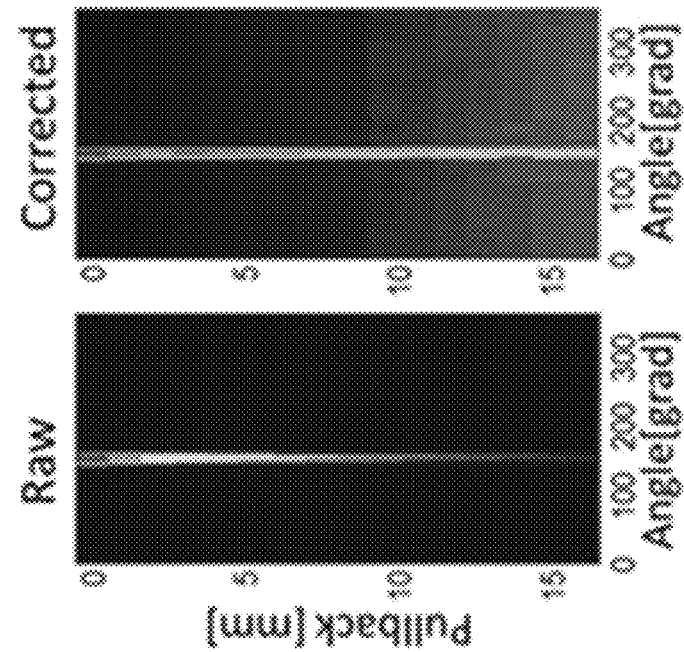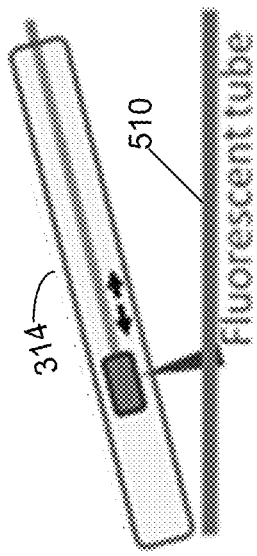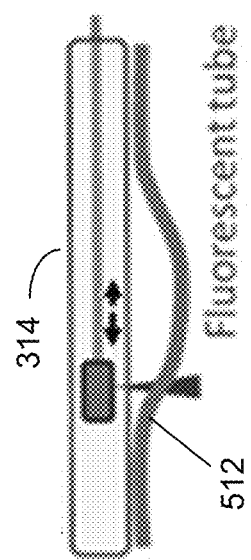

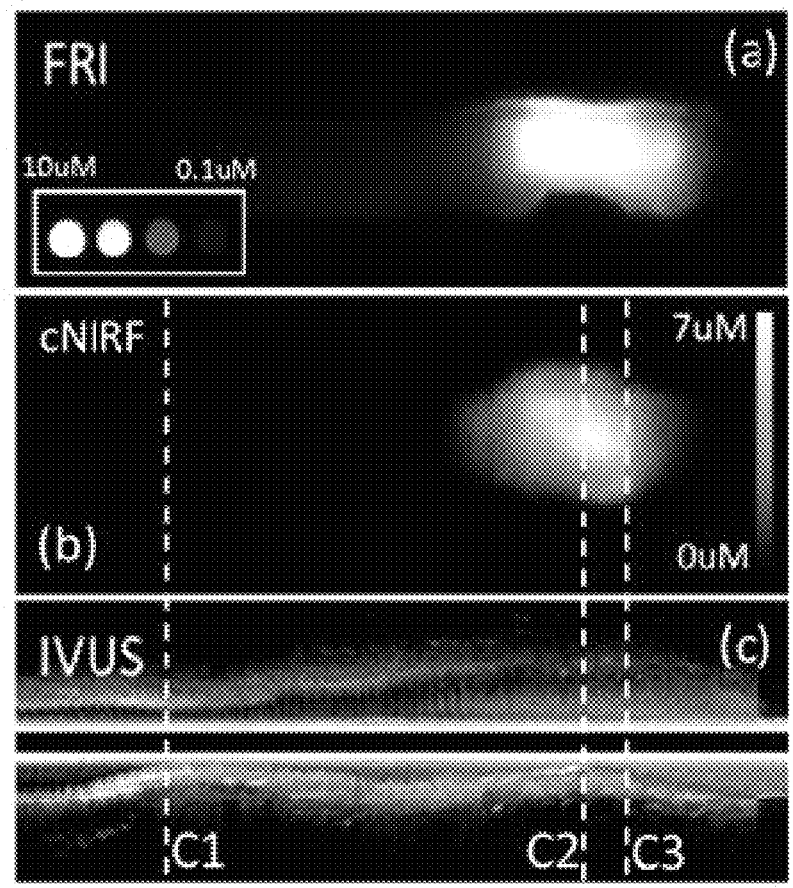
FIG. 7A
FIG. 7B
FIG. 7C
FIG. 7E
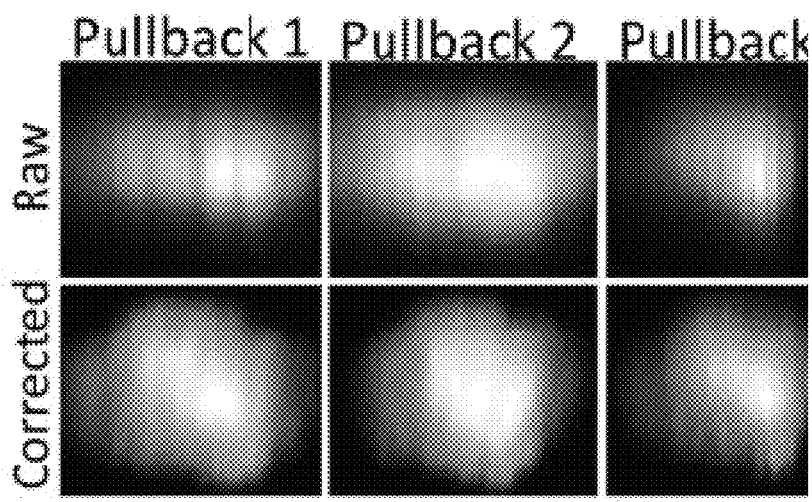

FIG. 8A
FIG. 8B
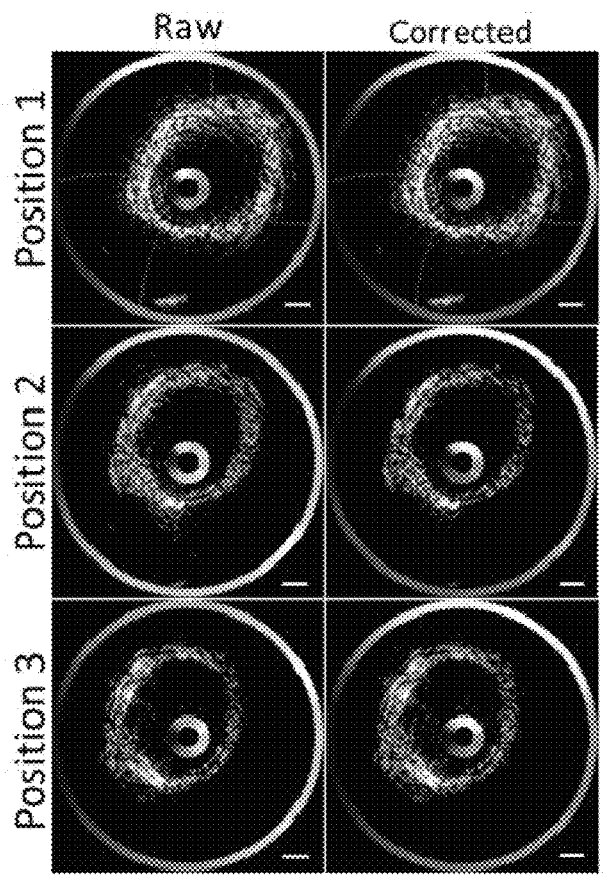
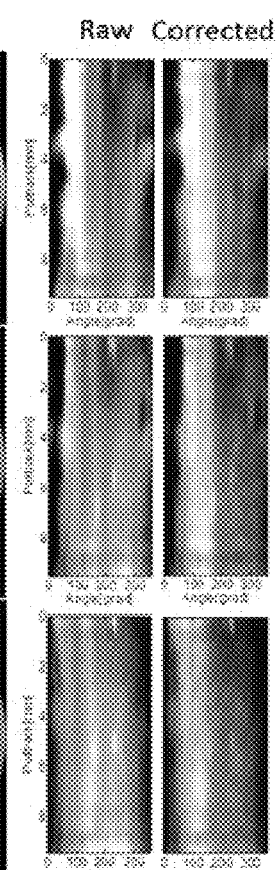
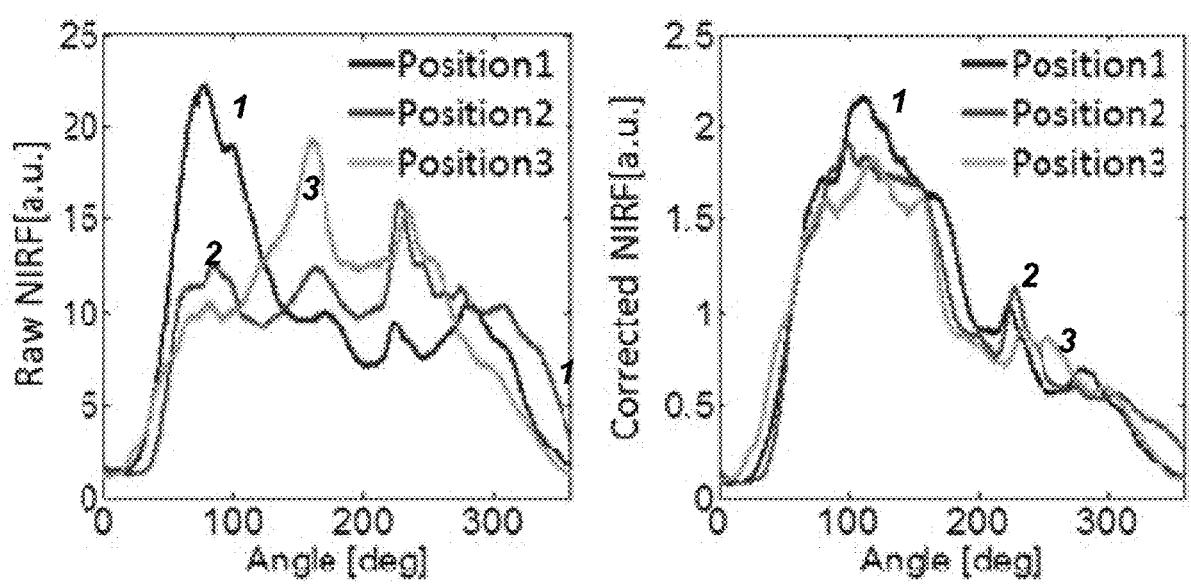
FIG. 8C (two plots)

HYBRID SYSTEMS AND METHODS FOR MULTI-MODAL ACQUISITION OF INTRAVASCULAR IMAGING DATA AND COUNTERACTING THE EFFECTS OF SIGNAL ABSORPTION IN BLOOD

CROSS-REFERENCE TO RELATED APPLICATIONS

The present application is a continuation-in-part from the U.S. patent application Ser. No. 12/020,765 filed on Jan. 28, 2008 and titled "Systems, Processes and Computer-Accessible Medium for Providing Hybrid Fluorescence and Optical Coherence Tomography Imaging", now issued as U.S. Pat. No. 9,332,942. The present application is also a continuation-in-part from the U.S. patent application Ser. No. 14/437,765, which was filed on Apr. 22, 2015, published as US 2015/0272445, and represents the national stage entry of PCT International Application No. PCT/US2013/065589 filed on Oct. 18, 2013. The PCT International Application No. PCT/US2013/065589, in turn, claims priority from and benefit of the US Provisional Patent Applications nos. 61/716,881 filed on Oct. 22, 2012 and titled "Hybrid Fluorescence-Optoacoustic Catheter", and 61/755,057 filed on Jan. 22, 2013 and titled "Hybrid Catheter System". The disclosure of each of the above-identified patent documents is incorporated herein by reference.

TECHNICAL FIELD

The present invention relates generally to medical imaging and, more particularly, to apparatus and process for generating images resulting from co-registration of fluorescence imaged and ultrasound images and representative of functional or molecular activity (which may indicate, for example, a disease in hollow organs) with the use of a hybrid multi-modality catheter system judiciously configured to appropriately tune the acquired data to incorporate factual light attenuation of light in blood.

RELATED ART

With applications of fluorescence imaging such as near-infrared fluorescent imaging or NIRF (and which is capable of two-dimensional imaging within human coronary-sized arteries), opened opportunities for imaging biological processes and/or characteristics associated with cardiovascular disease and treatment based on fluorescent agents. Two main features limit the utilization of a standalone NIRF-based imaging modality. First, NIRF by itself does not provide morphological information, which is a key aspect of current clinical interrogation and diagnosis. Second, NIRF images do not represent the concentration of fluorophore in the wall of the blood vessel, but rather represents the amount of fluorescence light collected by the NIRF catheter. Blood present in the vessel substantially attenuates the fluorescence signal transmitted from the target tissue. Therefore the NIRF images are subject to quantification errors imposed intravascularly by the relative geometry (distance) between the catheter and the vessel wall, which limits the accuracy of the NIFR imaging method.

As was also discussed, in relevant part, in the parent application, while intravascular ultrasound (IVUS) and intravascular optical coherence tomography (IVOCT) have become primary diagnostic and theranostic tools in the coronary, carotid, and peripheral arteries (where their use allows to assess atheroma burden, structural components, and aspects of endovascular interventional therapy such as angioplasty and stenting), the ability of IVUS and IVOCT to reveal the underlying biology of arterial and stent pathophysiology is limited by the physical mechanisms that determine their contrast (i.e. the reflection of sound or light from corresponding reflecting tissue). For example, resolving functional parameters (such as permeability, inflammation, oxidative stress or angiogenesis) are important in the study of endovascular injury and atheroma progression and complication, but remain unattainable by IVUS and IVOCT. IVUS technology, which features separate engineering designs for coronary and carotid/peripheral arteries, was shown to image the entire blood vessel wall in the presence of blood. IVOCT, on the other hand, offers pullback speeds of 40 mm/sec and superior resolution, but requires flushing and may only image the superficial layers of the artery wall. Both strategies are primarily used to visualize the anatomy of the vessel, as well as image plaque components such as calcifications, lipid pools, and thrombosis.

While hybrid imaging has been attempted ex vivo by fusing NIRF and IVUS based images, the technical possibility of employing hybrid NIRF-IVUS in-vivo to produce reliable results remains elusive: ex-vivo studies do not provide evidence as to whether correct, legitimate results can be acquired by intravascular NIRF-IVUS imaging in living subjects.

SUMMARY

Embodiments of the present invention provide an apparatus for obtaining information regarding at least one portion of a chosen biological target. Such apparatus includes (i) a catheter having proximal and distal ends and an axis and having a first channel and a second channel, the catheter configured to transmit at least first, second, and third radiations; and (ii) a detector operably connected with the proximal end of the catheter to acquire radiation energy and to produce output data representing said target, where output data includes a first portion representing the first radiation and a second portion representing the second radiation. In such apparatus, the first channel includes a first optical waveguide configured to transmit the first radiation generated within said biological target in response to absorption by the target of third radiation transmitted through catheter; the second channel is configured to transmit, from the biological target the second radiation representing anatomical characteristics of the target, where the second radiation is generated in response to at least one of ultrasound or optical radiation and each of the first and second channels is structured to deflect a radiation transmitted through such channel to cause the radiation transmitted through such channel traverse a first portion of such channel along the axis and traverse a second portion of such channel along a line that is transverse to the axis.

Embodiments of the invention further provide an apparatus configured to obtain information regarding at least one portion of a biological target. The apparatus includes (i) a catheter that has proximal and distal ends and an axis and that contains first and second channels configured to transmit, aggregately, at least first, second, and third radiations; and (ii) a radiation detection system that includes an optical detector in operable communication with the proximal end. The radiation detection system is structured to acquire radiation energy from the catheter to produce output data representing the target and including a first data portion representing the first radiation and a second data portion representing the second radiation. The first channel includes a waveguide configured to transmit the first radiation generated within the biological target in response to absorption, by the biological target, of the third radiation. The second channel includes a waveguide configured to transmit, from the biological target, the second radiation that represents anatomical characteristics of the target and includes at least one of a mechanical wave and an optical wave, the second radiation generated in respect to at least one of mechanical and optical waves transmitted from the catheter to the target. In a specific implementation, each of the first and second channels of the catheter is structured to redirect a radiation transmitted through such channel to cause this radiation traverse a first portion of such channel along the axis of the catheter and a second portion of such channel along a line that is transverse to the axis of the catheter.

Embodiments also provide a method for intravascular imaging of a target. Such method includes simultaneous acquisition from hollow organs and through a biological fluid in vivo, with a combination of first and second radiation channels of a multi-channel catheter having an axis, of (i) a first radiation generated at the target as a result of absorption, by the target, of a second radiation that has been delivered to the target through one of the first and second radiation channels, and (ii) a third radiation, produced at the target in response to insonation of the target with a fourth radiation delivered to the target with the use of another of the first and second radiation channels. The method further includes the steps of forming a first representation of a biological response of the target to the second radiation based on the first radiation and forming a second representation of a morphological characteristic of the target based on the third radiation. The method may additionally include (iii) determining a distance-dependent characteristic of the biological fluid in vivo, which characteristic represents at least one of absorption and scattering of at least one of the first and second radiations in the biological fluid in vivo; and (iv) transforming the first representation to a third representation that is devoid of a distance-dependent error caused by such absorption and scattering.

Embodiments additionally provide a method for intravascular imaging of a target. The method combines steps of simultaneous detection (with the use of a detection system operably connected to a proximal end of a multi-channel catheter that is configured to channel simultaneously first, second, and third radiations therethrough) of (a) a signal representing the first radiation transmitted from the target through blood in vivo in response to irradiation of the target by a second radiation, and (b) a signal representing the third radiation, transmitted from the target through the blood in vivo. The method also includes spatially co-registering first and second images of the target (which are formed based on the signal representing the first radiation and the signal representing the third radiation) the first and second images aggregately containing a representation of a biological response of the target and a morphological characteristic of the target. Further, the method includes transforming one of the first and second images to create a third image in which visual information representing the biological response has been corrected to account for a distance-dependent characteristic of at least one of the first and second radiations in said blood in vivo.

BRIEF DESCRIPTION OF THE DRAWINGS

FIGS. 4A and 4B illustrate characterization of the NIRF and IVUS signal profiles for catheters containing a combination of cNIRF-IVUS channels. FIG. 4A: NIRF sensitivity as function of detector-to-target distances measured in blood (red dots) and saline (blue dots). FIG. 4B: Lateral resolution of the NIRF and US detectors measured as function of detector-to-target distance. Red dots represent NIRF resolution in blood, blue dots—NIRF resolution in saline, green triangles—resolution of the 40 MHz IVUS transducer, purple triangles—resolution of the 15 MHz IVUS transducer.

FIGS. 5A, 5B, 5C, 5D, 5E, and 5F illustrate measurements of distance attenuation model $\alpha(r)$ and validation of correction model. FIG. 5A: Setup arrangement for measurement of $\alpha(r)$ in saline and ex vivo blood. FIG. 5B: Setup arrangement for in vivo validation of the ability of the probe, containing a combination of cNIRF-IVUS channels configured according to the idea of the invention, to resolve attenuation changes in blood. NIRF signal from a tube with AlexaFluor 750 detected over increasing catheter-target distance is shown before the distance correction (FIG. 5C) and after the distance correction (FIG. 5D). FIG. 5E illustrates the distance attenuation model $\alpha(r)$ measured in saline (blue), in vivo blood (red), and ex vivo blood (green). FIG. 5F: Light attenuation due to blood with normal (blue) and low (green) level of HCT measured in vivo with cNIRF-IVUS combination of channels. Lines represent fits to Twersky model.

FIG. 6A: Trace of a NIRF pullback in a healthy blood vessel after systematic injection of fluorescence agent. Low-frequency component correlates with catheter position within a vessel. FIG. 6B shows a representative cross section of the healthy vessel determined with the use of an embodiment of the invention. FIG. 6C: data representing cross sections of FIG. 6B converted to Cartesian coordinates were used to calculate a thickness of blood through which fluorescent light emitted by the target was detected. Lines 610, 612 outline lumen. FIG. 6D is a curve representing NIRF signal normalized for beam size as a function of catheter-vessel wall distance. All scale bars 1 mm.

FIGS. 7A, 7B, 7C, 7D, 7E, and 7F illustrate the methodology of intravascular cNIRF-IVUS hybrid imaging with an embodiment of the invention (with the 40 MHz version of the hybrid catheter), revealing the value of IVUS-based distance correction of the NIRF signal in blood. In vivo cNIRF-IVUS imaging of a swine carotid artery was performed followed local injection of an NIR fluorophore. Images of FIGS. 7A, 7B, 7C show an FRI image of the artery obtained ex vivo, the cNIRF image and corresponding longitudinal IVUS image, respectively. FIG. 7D: A three-dimensional representation of the lumen and arterial wall NIR fluorescence signal rendered based on the in vivo cNIRF-IVUS measurement. Inset figures C1, C2 and C3 show representative examples of the cross-sectional cNIRF-IVUS images corresponding to pull back positions C1 C2 and C3 in FIGS. 7B, 7C, and 7D. The cNIRF signal in C1, C2, and C3 inset axial images is fused onto the interior and exterior of the IVUS catheter. FIG. 7E: Serial imaging of the same region of the vessel (top row) showed that NIRF images are affected by variable intraluminal catheter location and by heartbeat and breathing motions. However, NIRF distance correction substantially improved the reproducibility of the NIRF image and lessened motion artifacts (bottom row). FIG. 7F: Corrected NIRF pullback images achieved better imaging accuracy. The maximum of the NIRF signal for every pullback position from three pullbacks is shown with black dots, blue line shows average distribution. The sum of squares due to error (SSE) decreased from 3 to 1.6, demonstrating an improvement in correlation between the distance-corrected signals compared to raw signals.

FIGS. 8A, 8B, 8C illustrate results of ex vivo imaging experiments in the abdominal aorta of a rabbit following AF750 NIR fluorophore injected into the artery wall. FIG. 8A: Three imaging sessions of the same region of the vessel were performed with catheter placed in different intraluminal positions. Representative ultrasound image of the vessel cross section obtained from each position is presented in black and white colors. Each colored circular ring represents corresponding raw NIRF or corrected NIRF signals, and are depicted on the interior of the IVUS catheter, as well as externally around the vessel wall. FIG. 8B: Representation of the raw and corrected NIRF two dimensional images obtained in different intraluminal positions. FIG. 8C Comparison between raw and corrected NIRF signals in pullback position 6 mm. All scale bars 1 mm.

FIG. 9A: Two imaging sessions of the same region of the vessel were performed with catheter placed in different intraluminal positions: top right (Position 1) and bottom-center (Position 2). Representative examples of the ultrasound images obtained from different positions are presented in black and white colors. Colored circular rings represent corresponding NIRF signal, and are depicted on the interior of the IVUS catheter, as well as externally around the vessel wall. FIG. 9B: Raw and corrected NIRF images obtained over whole pullback in Position 1 and Position 2, respectively. All scale bars 1 mm.

FIG. 10A demonstrates a zone of impaired vascular barrier allowing ICG extravasation into the media that is associated with thinning and discontinuity of elastin fibers in the internal elastic lamina (VVG stain, arrows). FIG. 10B demonstrates a separate zone from the same artery with preserved endovascular integrity, characterized by an intact elastic lamina and without ICG extravasation. FM, fluorescence microscopy.

FIG. 11A: Longitudinal representation of the NIRF-IVUS pullback. NIRF-IVUS cross section in the area of plaque (1) and healthy area (2) is shown in FIGS. 11B and 11C, respectively. All scale bars 1 mm.

DETAILED DESCRIPTION

Figure 1A:
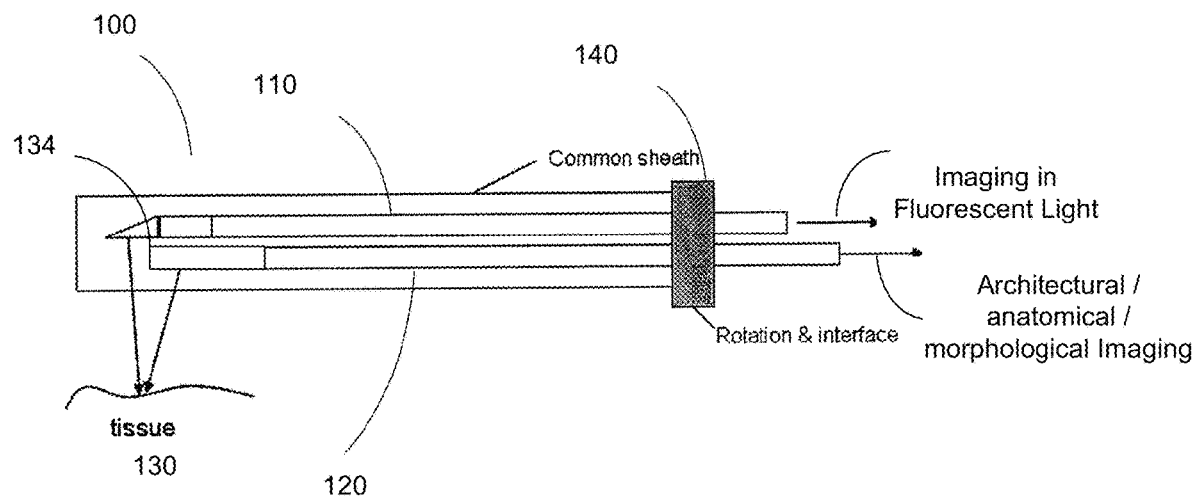
FIG. 1A is a schematic illustration of an embodiment of the multi-modal/multi-channel intravascular catheter configured according to the idea of the present invention.

Some examples of implementations of NIRF imaging in optional combination with other modalities were already discussed in US 2009/0192358, which is referred herein as parent application, and utilized NIRF imaging of a target through blood effectuated via rotation of an imaging channel of the used catheter.

Empirical findings, discussed below, uncovered remarkable and unexpected differences between the levels of light-signal attenuation obtained in blood ex-vivo vs. that obtained in-vivo. While the applicants postulate that the decreased attenuation of in vivo blood as compared to that in ex vivo blood could be due to differences in oxygenation levels of blood and/or presence of flow and/or effect of absorption flattening, such factual difference establishes that the practical transition from the use of a multi-modal imaging system combining NIRF-based measurements with the measurements configured to provide the information about the anatomical characteristics of the entire blood vessel in the presence of blood (such as IVUS and/or IVOCT modalities) from ex vivo measurements to in vivo measurements remains far from being a matter of routine operation or trial and far from being obvious at least due to these quantification challenges, which have not been addressed by related art.

Embodiments of the present invention address persistent and thus far not-realized need to realize a numerically-correct imaging of a target during in vivo measurements in a bodily fluid (specifically, blood). In particular:

A multi-modality hybrid catheter or probe, configured as a radiation relay system and containing a combination of the NIRF-based imaging channel and another, complementary imaging channel (such as a channel configured to relay information representing architectural/anatomical/morphological structure of the target, be it OCT-based imaging channel or the IVUS-based imaging channel) in the same housing unit, was created to solve the problems caused in the related art by (i) inability of a stand-alone NIRF imaging system to provide morphological information about the imaged target (and, therefore, its failure to enable the intravascular clinical interrogation and diagnosis), as well as inability of the stand-alone NIRF imaging system to assess the concentration of fluorophore in a wall of the blood vessel, and (ii) operational limitations of the stand-alone architectural imaging modality (OCT-based or IVUS-based) to provide information regarding pathophysiology and biological processes underlying and biological characteristics describing vascular injuries, deficiencies, and diseases (such as inflammation, oxidative stress, and atherosclerosis, for example). The multi-modality hybrid-catheter imaging system is configured to precisely co-register an NIR image with a morphological image that reveals both the vessel anatomy image and the distance between the catheter and the vessel.

The problems caused by a priori not-ascertained measurement errors, known to accompany the application of the hybrid multi-modality catheter during the measurements in vivo and caused by reliance of the related art on the use of such catheter in ex vivo measurements have been solved by devising an in-vivo-specific distance-correction procedure applicable to measurements through blood in vivo and not appropriate or applicable to the ex vivo measurements.

The combination of the NIRF modality (the first modality) and at least one of the OCT and IVUS imaging modalities (any of which is can be referred herein as a second modality) configured according to the idea of the invention offers a complementary contrast dimension to imaging that is based on the second modality. Specifically, while the second modality is capable of assessing the anatomical/morphological details of the target, the NIRF-based imaging is structured to detect a biological response of the tissue (biological, pathophysiological, cellular, and molecular information, to mention just a few). Accordingly, the practically non-trivial cooperation of the first and second modalities may add a new dimension to characterization of the biological tissue. The empirically-verified solution(s) to the above-stated problems, which are discussed below, can and are applied to the combination of the NIRF- and OCT-based imaging and the combination of the NIRF- and IVUS-based imaging, and both of such applications are within the scope of the invention.

The "cooperated", multi-modality system of the invention is configured to enable a correction for light attenuation in in-vivo blood, unavailable thus far in related art, to provide for numerically-accurate NIRF readings in vivo and concurrent quantitatively-accurate molecular and morphological imaging of arteries in vivo.

Examples of an In-Vivo Multi-Modal Imaging System

Several examples of such imaging system have been already discussed in the parent application, including an imaging system employing a hybrid catheter containing several imaging channels (in a non-limiting example, a NIRF channel and/or an acoustic, IVUS, channel and/or an OCT channel; because the useful application of the OCT modality is limited to visualization the first approximately 1 to 2 mm of plaques, the OCT may not be the best choice for measurement of plaque burden, plaque volume, medial thickness, or define the volume of certain plaque components like the necrotic core. For these situations, ultrasound (US), NIR spectroscopy, and MRI and CT might provide required information. In particular, disclosed was an example of the embodiment configured to effectuate, concurrently, an approximately 360-degree fluorescence-based imaging with imaging of a structure/architecture of the vessel with integrated OCT and/or optionally another modality including but not limited to ultrasound, MRI, NIR, other type of spectroscopic imaging, nuclear imaging); and/or depth-resolved and depth-and-optical-property-corrected fluorescence imaging using OCT registration.

The parent application disclosed in detail an intraluminal catheter configured for hybrid imaging (three dimensional imaging at multiple optical wavelengths and/or with an acoustic wave/ultrasound, which is one specific case includes quantitative fluorescent imaging by employing concomitant/integrated imaging of the architecture of the hollow organ structure and in another specific case employs the combination of the near IR fluorescent imaging with ultrasound-based imaging).

A schematic diagram of such hybrid catheter is shown, for example, in FIG. 1A. The invention is directed to a radiation relay system configured to deliver, through a distal end of the radiation relay system, multiple radiations (in a specific case, at least three radiations between the proximal end of the probe and the target, in either direction). Such multiple radiations differ not only by the wavelength and manner in which they are caused but also in nature. For example, at least one of the multiple channels of the catheter 100 is configured for channeling an optical wave, while another channel may be configured for channeling a mechanical, substantially coherent wave (for example, an acoustic wave). In the schematic FIG. 1A, 110 and 120 denote signal channels of the multichannel hybrid catheter 300 (and can include an optical waveguide for transmission of optical radiation to and from the target/intravascular tissue 130 and/or a waveguide for transmitting an acoustic signal, such as an ultrasound transducer channel, for example). Generally, a related embodiment may include more than two channels in the hybrid catheter of the invention. Generally, therefore, embodiments of the invention presented an apparatus configured to obtain information regarding at least one portion of a chosen biological target. Such apparatus includes a catheter having proximal and distal ends and an axis, and an optical detector system (that included an optical detector) in operable communication with the proximal end. The catheter contained first and second channels configured to transmit, aggregately, at least first, second, and third radiations. The first channel includes a waveguide configured to guide the first radiation generated within the biological target in response to absorption, by the biological target, of the third radiation transmitted through catheter. The second channel includes a waveguide configured to channel, from the biological target, the second radiation (that represents anatomical characteristics of the target, that includes at least one of a mechanical wave and an optical wave, and that is generated in response to at least one of mechanical and optical waves transmitted through the catheter to irradiate the target). The radiation detection system containing a data-processing electronic circuitry (in one case—the optical detection system that contains an optical detector) is configured to acquire radiation energy from the catheter and to produce output data representing the target and including a first data portion representing the first radiation and a second data portion representing the second radiation. In a specific case, each of the first and second channels is structured to redirect (for example, deflect) a radiation transmitted through such channel to cause this radiation traverse a first portion of such channel along the axis of the catheter and a second portion of such channel along a line that is transverse to the axis of the catheter. In another specific example, where first and second channels are optical channels and include optical waveguides (such as two different optical fibers or two optical waveguiding structures one of which is built co-axially and concentrically with respect to another of the two optical waveguiding structures), each of such channels of the probe 100 is configured to ensure that in the process of optical radiation delivery every radiation is spatially deflected transversely, for example with the use of optical prismatic element(s) at the such as element 134 with respect to the original direction of propagation of optical radiation.

Figure 1B:
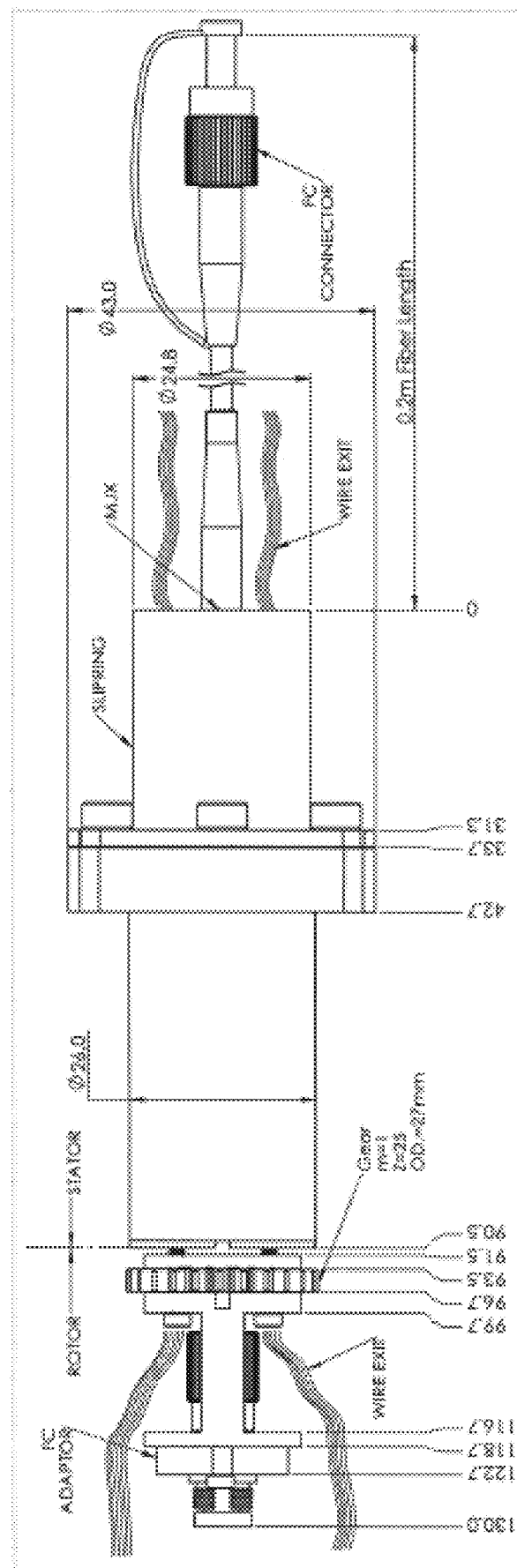
FIG. 1B illustrates an example of a rotary junction for use with an embodiment of the invention.

To enable rotation and pull-back operation of the catheter 100, the catheter rotation mechanism such as a rotary junction 140 (employing a rotary joint) complemented the embodiment of the probe 100. A non-limiting example of a rotary joint 140 is shown in the views of FIG. 1B, illustrating the rotor-to-stator slip-ring-to-brush signal-transforming contraption (as shown, equipped with FC optical connectors on both ends, which is readily expandable to connectors structured to accept electrical wire(s)).

Figure 2:
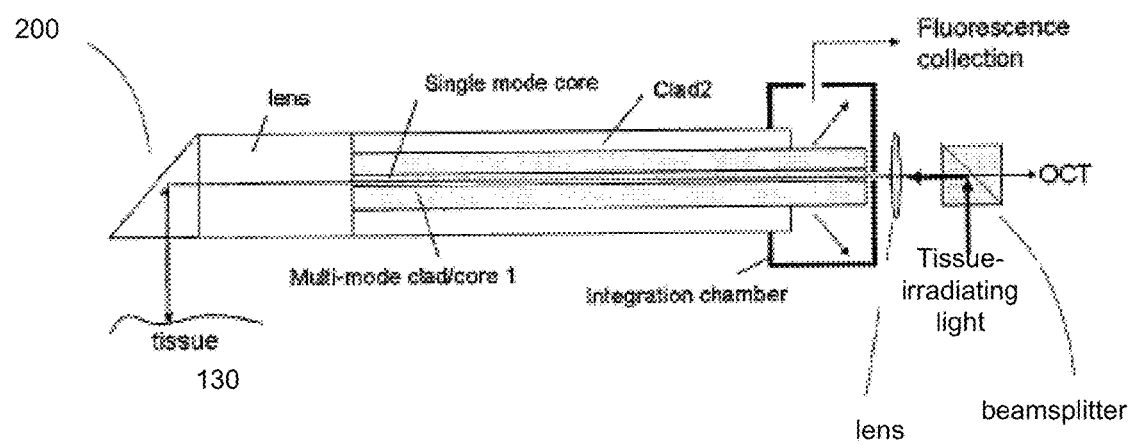
FIG. 2 is a schematic illustration of another embodiment of the catheter of the present invention.

Yet another specific implementation of the probe 100 was dimensioned such that each of the two channels includes an optical waveguide, and that the optical waveguide corresponding to the first of the two channels is coaxial and concentric with the optical waveguide corresponding to the second of the two channels. A schematic diagram of such specific implementation of the NIRF-OCT channel containing catheter 200 is presented in FIG. 2 (the rotary joint is not shown for simplicity of illustration). To enable the rotation and pull-back operation of the catheter 100, the catheter rotation mechanism such as a rotary junction 140 (employing a rotary joint) complemented the embodiment of the probe 100.

In reference to FIG. 4 of the parent application, examples were discussed of methods for generation of at least a) semi-quantitative three-dimensional images, and b) quantitative four-dimensional fluorescence images co-registered with architectural (OCT) images obtained with an embodiment of the hybrid catheter and system employing it.

With respect another specific implementation of the hybrid catheter 100 of the invention—specifically, the catheter that contains not only an optical channel (such as a channel configured to transmit near IR fluorescent radiation) but a channel configured to transmit an acoustic wave (for example, ultrasound), it is recognized that, in contradistinction with any system of the related art that suffers from thus-far unavoidable measurement error(s), embodiments of the present invention are judiciously adapted to achieve numerically-correct simultaneous and co-registered NIR fluorescence and ultrasound imaging in vivo. The experimental structure of such specific multi-channel NIRF-IVUS embodiment of the catheter included two major components: the back-end console configured to drive/govern the operation of the ultrasound and optical elements and to collect and process the acquired data, and the front-end intravascular catheter or probe. Such implementation is configured to include at least first and second channels which, together, are configured to transmit at least first, second and third radiations. For example, the first channel is configured to transmit fluorescence-exciting radiation from the external light source at the distal end of the catheter towards the target and the fluorescence from the target through the proximal end of the catheter towards the distal end of the catheter. The second channel is configured to include an ultrasound transducer element converting the electro-magnetic radiation delivered along the channel from its distal end into the acoustic signal directed towards the target, and vice versa.

Either implementation of the multi-modal catheter system of the invention that employs the first and second imaging modalities may also include a synchronization component or unit including, for example, as a synchronous clock operably cooperated with a programmable computer processor and configured to synchronize the information received from the target through the channel of the first modality with that received along the channel of the second modality. In one case, when the fluorescence and OCT-based imaging principals are employed by the system of FIG. 1A, and when the fluorescence and OCT sub-systems are operating asynchronously in sending the light through the catheter towards the tissue, such synchronization component may incorporate program code keeping track (optically and/or electrically) of pulses of light from each of the sub-systems or assigning the same time axis to the sequences of data obtained from both the first and second modalities, assuming the same starting time for data acquisition for both modalities. In another non-limiting example, the synchronization component may include fiduciary markers on the catheter system that are configured to be visualized (imaged) by both the first and second modalities to align respective imaging data. In yet another example, the synchronization component may include an active triggering device that governs or drives the first and second modalities synchronously by, for example, sending predetermined triggers to the fluorescence excitation laser (employed as a source by the first modality) and either the OCT-dedicated laser source or the ultrasound pulser (either of which can be employed as a source by the second modality).

Fluorescence Detection Sub-System

Figure 12A:
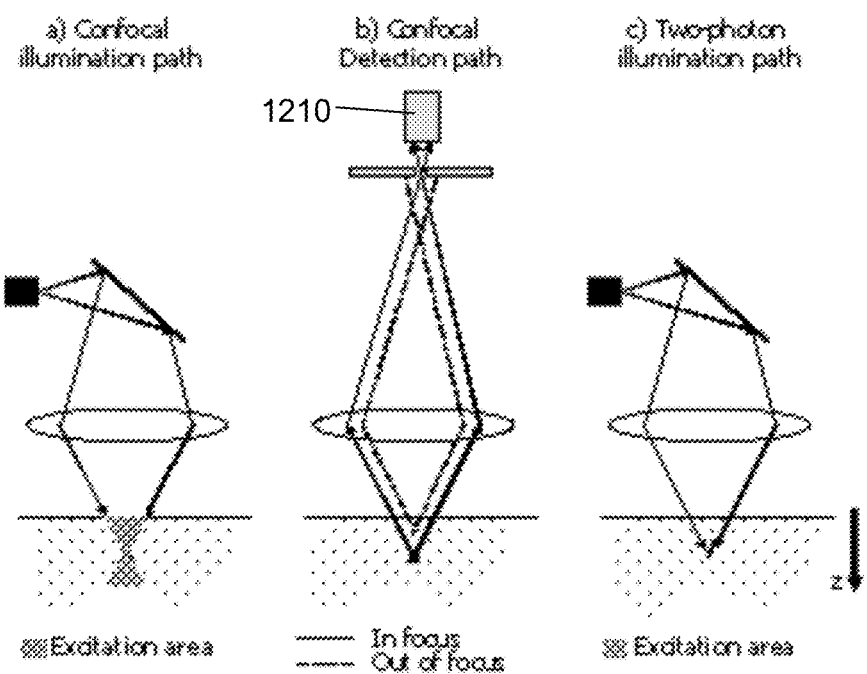
FIGS. 12A and 12B illustrate an example of a fluorescence detection system that can be used with an embodiment of the invention.
Figure 12B:
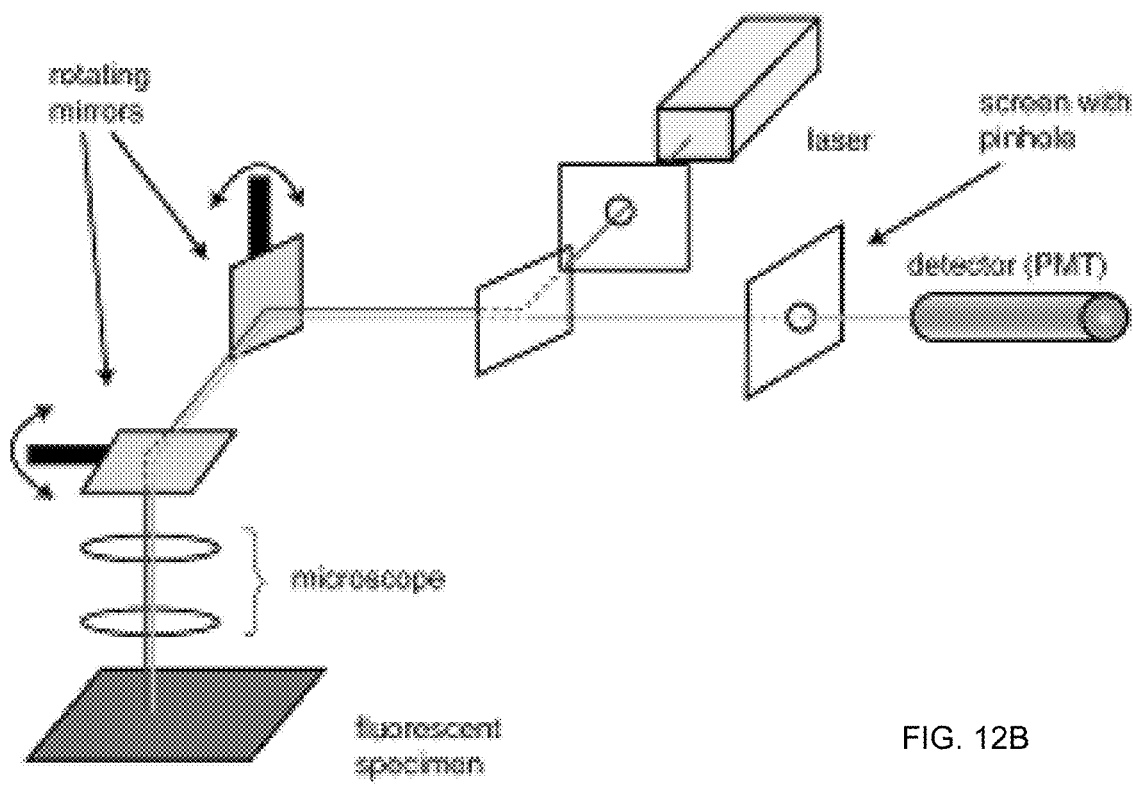

Either implementation of an embodiment of the invention that employs and simultaneously operates the first and second modalities may utilize a fluorescence detection system that includes a synchronized photon detector module containing attenuation optics to facilitate operation of the multi-modal system in a wide dynamic range. Examples of fluorescence detection include detection from a focal point (with the use of an appropriate optical focusing system), detection from a broader surface area and/or tissue sectioning detection. An exemplary embodiment of a tissue sectioning detection includes but is not limited to a method where appropriate optics are used to reject light from other areas but an area of focus inside tissue: for example, a confocal detection or two/multi-photon detection, the schematics of the optical systems of which are presented in diagrams of FIG. 12A. Confocal detection (diagrams a) and b)) can be achieved with the use of a pinhole; see the diagram of FIG. 12B. By changing the focal point in the tissue and in relation to the pinhole it becomes possible to procure three-dimensional information. The confocal-detection system may utilize a lens or an optical fiber for light delivery to the excitation area. In the latter case, low-mode or single-mode fibers may be preferred to maintain required light-focusing characteristics at the excitation area. In a two-photon detection case, the detection and illumination paths for which are also illustrated in FIG. 12A in a diagram c), an ultra-fast pulsed laser is often employed as a light source.

The fluorescence detection system of an embodiment may utilize is a single point detector, such as a PMT or APD, and optionally equipped with optical filter(s). While the single point detector is indicated as 12010 only in diagram b) of FIG. 12A, its use is appropriate for either a simple fluorescence detection, a confocal, or a two-photon version of the detection.

To realize depth-dependent measurements with the use of a fluorescent detection system, optical components of the fluorescence detection system may be dynamically changed. In doing so, focusing of the tissue-interrogating radiation at different depths is achieved with the use of, for example, a variable lens in front of the fiber (using MEMS/other) or changes of the photon field or fiber distance to the lens.

Additional Examples of an In-Vivo Multi-Modal Imaging System.

Figure 3:
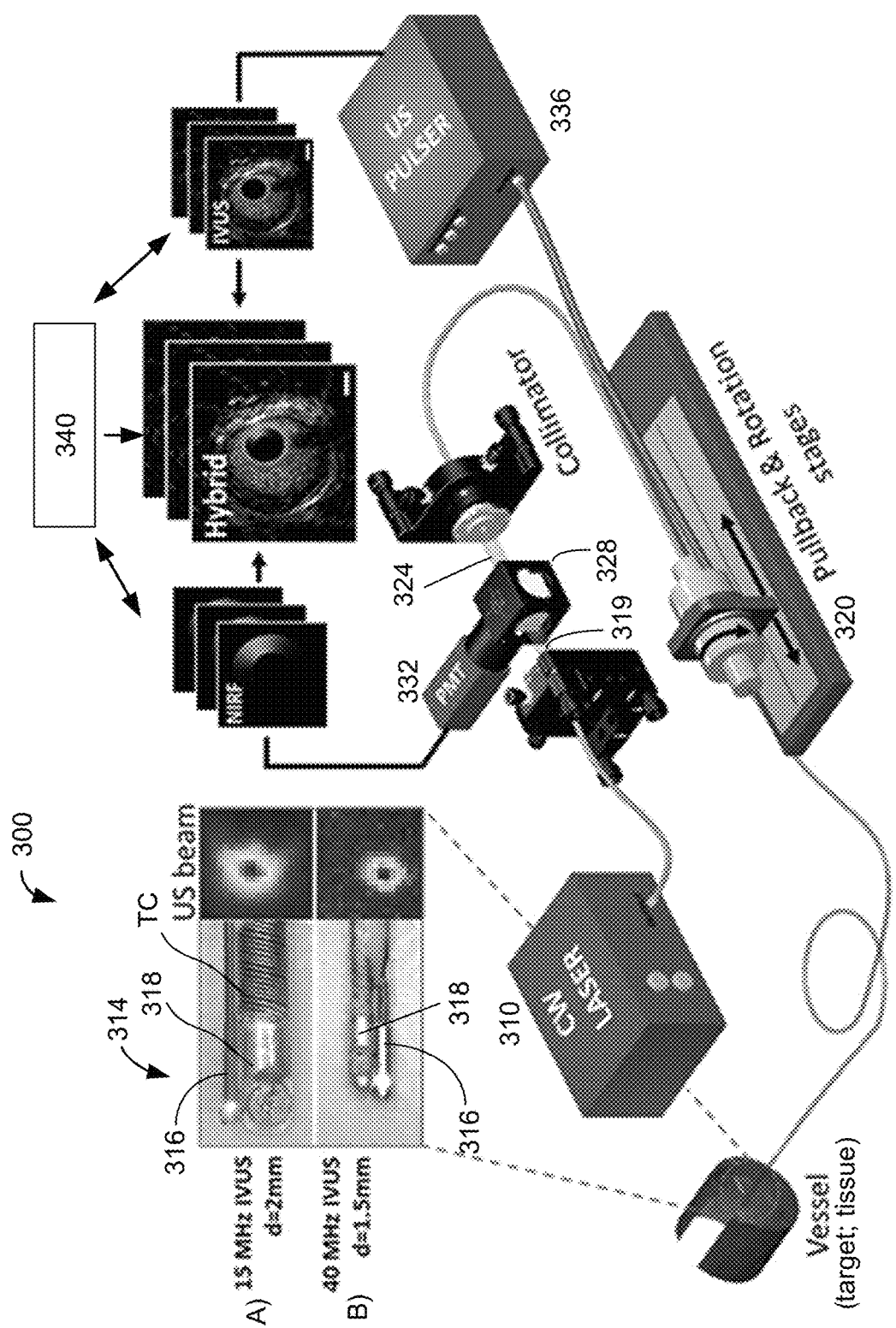
FIG. 3 schematically illustrates an imaging system configured according to the idea of the invention to contain a multi-modality imaging catheter, containing both the cNIRF and the IVUS channels.

In reference to FIG. 3, an embodiment of the imaging system 300 that includes a probe/catheter 314 combining optical and acoustic signal-collecting channels (and for simplicity referred to, interchangeably, as a cNIRF-IVUS, although it is understood that additional channel(s) can be and are in one embodiment present in the probe, such as a channel configured to collect from the target OCT radiation representing anatomical characteristics of the target) was configured to employ a continuous wave (CW) laser source 310 operating at wavelength 750 nm (B&W Tek Inc., Lubeck, Germany). The hybrid imaging probe/catheter 314 (the two related implementations of which A) and B) are shown) included an optical waveguide 316 (in a specific case, configured as an optical fiber having a 250-micron diameter) combined with an ultrasonic transducer 318 and housed in a transparent sheath, which was equipped with a radiopaque marker on its tip for angiographic guidance. It is appreciated that in some embodiments, at least one auxiliary optical waveguide (not shown in FIG. 3) was additionally placed within the sheath to deliver optical radiation 319 from the outside laser source to the target and/or collect optical radiation produced by the target in response to the delivered optical radiation. In order to guide laser illumination at a 90-degree angle from the axis of the optical waveguide to the vessel wall, a 0.25 mm beam-deviating prismatic element (Precision Optics Corporation, Gardner, Mass. USA) was mounted on the distal end of the optical waveguide 316 and/or at least one more auxiliary optical waveguide, in accordance with the discussion of the general structure of the probe presented above.

In a specific case, the ultrasound transducer 318 and the optical waveguide 316 were aligned so that angular and longitudinal offsets between optical and ultrasonic beam was 6.8° and 90 μm, respectively, what is below the ultrasound resolution of the system. Indeed, both NIRF and IVUS channels are disposed to visualize/image substantially the same area/volume of the target at any time. Generally, the rotation of the catheter with the use of a rotary joint (such as the joint 140) imposes different linear velocities of rotation onto the NIRF and IVUS channels, and the channels acquire slightly different imaging data and cause the unit 340 to record slightly different images. The mechanical offsets described above were intentionally employed between the radiation channels to substantially equate characteristic of rotation of said first and second channels during simultaneous and co-dependently rotation of the channels and to compensate for such undesired effect and to spatially-coordinate and align the resulting images.

In addition or alternatively, any remaining misalignment between the recorded images is corrected in a data-processing unit of the system by "shifting" at least one of the corresponding images. It is realized that the operationally preferred correction of radiation data from the target would be to have one of the radiation channels arranged concentrically and/or co-axially with another radiation channel (for example, by placing the channels containing the ultrasound sensor concentrically with the optical waveguide, by analogy with the idea of the concentric/coaxial disposition of the two optical waveguides according to the schematic of FIG. 2). In this case, the spatial alignment is also configured to be concentric.

The hybrid modality catheter 314 was automatically rotated inside the sheath at rotation speeds up to 160 revolutions per minute (rpm) and translated with a step size of 0.2 mm per rotation using mechanical stages 320 (Oriental Motor co Ltd, model EZ Limo and VEXTA). Whether or not the channels 316, 318 are made concentric/coaxial to one another, and independently of the particular way of operationally-combining these NIRF and IVUS channels together, the channels 316, 318 are preferably rotated at the same speed/rate about the axis of the catheter in order to record the target concurrently, which was implemented in the current case. It is understood, however, that related embodiments of the device include implementations providing for different rotation/translation speeds of the channels, in particular in order to account for different signal-to-noise ratios associated with signals acquired by these channels.

To facilitate the rotation of the catheter 314 with the use of a rotation joint, the torque coil TC may be placed around a radiation channel used to facilitate the rotation of the catheter with the use of the rotations joint (such as the joint 140). In a specific implementation (not shown), and in advantageous improvement of the contraption 300, the torque coil is disposed over and around both radiation channels 316 and 318.

Fluorescent light, emitted by the target, was captured by the optical fiber 316 or by the auxiliary optical waveguide. In the former case, the fluorescent light collected from the target was separated from the optical radiation delivered to the target from the source 310 along the waveguide 316 through the use of an optical filter unit 328 that included, in a specific implementation, a dichroic mirror (DM) with 765 nm cut-off wavelength (AHF Analysentechnik AG, Tubingen, Germany) and three long pass filters with 780 nm, 785 nm and 800 nm cut-off wavelengths. An optical detection system 332 containing an optical detector (in one specific implementation—a photomultiplier tube, (PMT such as model H5783-20, Hamamatsu Photonics, Shizuoka Pref., Japan) and dedicated electronic circuitry was used for the acquisition and detection of the fluorescent light.

Notably, specific embodiments of the invention may be configured to be devoid of a lens-element in the catheter (not shown), which is in contradistinction with catheter-based probes typically used in related art.

Simultaneously with such acquisition of optical signal, ultrasound imaging was performed utilizing the transducer 318 in pulse-echo mode. In particular, in one implementation of a data-acquisition process, simultaneous excitation of the NIR laser light (CW) and pulsed ultrasound every 100 microsecond was used to detect generated fluorescence emission and ultrasound signals in co-registered fashion. Structural depth profiles (A-lines) and corresponding NIR fluorescence intensities were sampled by the hybrid detector during helical (rotational plus translational) pullback scanning. As shown in FIG. 3, an electric pulser-receiver electronic circuitry unit 336 (Olympus 5073PR, Hamburg, Germany) was connected to the ultrasound transducer to generate the ultrasound pulses and measure acoustic echoes acquired from the target by the transducer 318. The pulser-receiver unit 336 was operated with a repetition rate of 10 kHz and detection amplification setting of 39 dB. Generally, different speeds and/or amplifications could be used. The detected signals were digitized at a sampling frequency of 200 MHz using dedicated data-acquisition and processing electronic circuitry unit 340 (which included, in one case, an data acquisition card by NI PCI-5124, Munich, Germany). Overall, the multi-modality system 300 acquired optical and US data to create morphological cross-sectional images of the vessel with spatial resolutions comparable with those of commercially available IVUS systems, while simultaneously co-registering NIRF molecular imaging readouts with the US readouts.

As shown in FIG. 3, two examples of implementation of hybrid catheter were built, shown as 314A) and 314B). The A) version was specifically configured to image arteries bigger than 5 mm in diameter (such as peripheral/carotid arteries) and utilized a lower-frequency, 15 MHz IVUS transducer.

In one specific embodiment, the catheter was housed in a fluorinated ethylene propylene (FEP) transparent tube (Zeus, Orangeburg, S.C. USA) with an inner diameter of 2 mm and full outer diameter of 3 mm (9 French). Reflection of the ultrasound energy from the water-FEP interface was measured to be 30-50% each direction. To avoid significant losses during the measurements, after the catheter 314 (whether version A) or B)) was positioned in the region of interest at the target, the hybrid detector was subsequently advanced out of the tube/sheath to perform pullback with a tip of the optical waveguide and expose ultrasound transducer to surrounding media (ambient blood or saline).

The second example (shown as B) in FIG. 3) of the cNIRF-IVUS containing multi-modality catheter 314 was designed to image smaller vessels such as the human coronary artery (diameter <5 mm) with higher resolution and, therefore, utilized a 40 MHz IVUS transducer. The 40 MHz model of the catheter was housed within a tube made of low-density polyethylene (LDPE) with an inner diameter of 1.2 mm and full outer diameter of 1.5 mm (4.5 French). Due to the close acoustic impedances of LDPE and water (1.79 MRayls and 1.48 MRayls, respectively), the reflection of ultrasound energy from water-LDPE interface was assessed to be only between about 5% and about 10%. Such choice made it possible to effectuate imaging from within the tube and without direct contact between the transducer 318 and the surrounding media. The distal end of the tube was sealed and tube was filled with distilled water for ultrasound coupling.

To connect the rotating hybrid catheter 314 with the stationary console, a hybrid rotary joint 320 was built (an example of which is presented in FIG. 1B) to ensure that rotating and stationary fibers were precisely aligned inside a chamber filled with an index matching fluid. The rotary joint 320 is configured to establish a direct fiber-to-fiber coupling with the use of precise mechanism for fiber alignment between stationary and rotating parts of the rotary junction The lens-free design of the hybrid rotary joint provided as low single pass optical loss as 3.7 dB. For transmission of ultrasound signals, at least one concentric slip ring was built around optical connector of the rotary joint. The round-trip insertion losses for the US signals caused by rotary joint were 2 dB and 5 dB for 15 MHz and 40 MHz versions of US transducers, respectively.

Pre-Characterization of the Embodiment of the NIRF-IVUS Based Imaging System

As would be appreciated by a skilled person, the beam of optical radiation emitted from the catheter such as catheter 314 towards the target has a diverging cone profile with aperture determined by numerical aperture (NA) of the constituent optical waveguide (as shown, 316), along which the radiation is delivered from the proximal end to the distal end of the probe, and a scattering coefficient of the surrounding media. Dimensions of this cone defined, in practice, resolution and sensitivity of the optical imaging modality (such as imaging at the wavelengths of the fluorescent light acquired from the target by the catheter 314).

To empirically assess the sensitivity of the NIRF data acquisition, a custom-made phantom was created. In particular, a tube filled with an NIR fluorophore (AlexaFluor 750) was fixed at an angle with respect to the pullback direction of the imaging system, to facilitate a measurement of the sensitivity as a function of the separation distance between the sensor and the target. With such arrangement, the sensitivity of the NIRF imaging was measured as a function of distance in blood and saline (see FIG. 4A). Blood has higher absorption and scattering than those of saline, leading to a much faster decrease of the sensitivity with distance. A 175 picomolar of NIR fluorophore was detected at fiber-to-target distances up to 2 mm with a signal-to-noise ratio (SNR) of about 2.5. In addition, the resolution of the NIRF imaging capability of the probe was investigated, and the full width half maximum (FWHM) of the NIRF signal from the target was measured at several distances (as shown in FIG. 4B) to provide the angular resolution at a 1 mm distance in blood if approximately 24° (15 sectors).

The lateral and axial resolutions of the ultrasound imaging modality of the embodiment 300 was determined by the US transducer's geometry and frequency. A copper wire of 100 microns in diameter was imaged at a different distances from the detector, establishing lateral resolution figure (for both the 15 MHz and 40 MHz implementations of the hybrid catheter) as a function of distance shown in FIG. 4B with triangular marks. It can be appreciated that the resolution of ultrasound imaging generally degrades with distance for both catheter implementations. At a typical imaging distance of about 2 mm, the 40 MHz catheter implementation demonstrated an approximately two-fold better lateral resolution as compared to the 15 MHz catheter model (270 microns and 500 microns, respectively), which corresponds to sectors of 8° and 16°. The axial resolution was not affected by distance and was determined by only frequency. It was measured to be 150 microns and 240 microns (for the 40 MHz and 15 MHz implementations of the catheters, respectively).

As it was already alluded to above, the practical problems caused by distance-related attenuation of fluorescence light In Vivo manifest themselves during the use of a nulti-modal catheter-based imaging system that employs both the first and second modalities (a NIR fluorescence based modality and either the OCT or the ultrasound based modality) and have not been addressed by related art. Accordingly, although the following discussion of the distance-related blood attenuation of light In Vivo in comparison with or independently from that for light Ex Vivo is presented through the example of the NIRF-IVUS system, the same solutions and methodologies are applicable to, for example, the NIRF-OCT system and are within the scope of the invention.

(A) Difference Between Distance-Related Blood Attenuation of Light Ex Vivo as Compared to that In Vivo and Methodology for NIRF-Based Correction of Blood Attenuation Data.

Figure 5F:
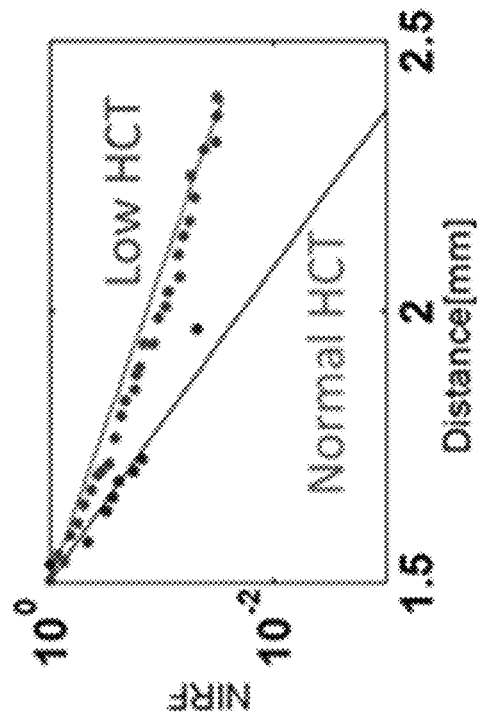
Figure 5E:
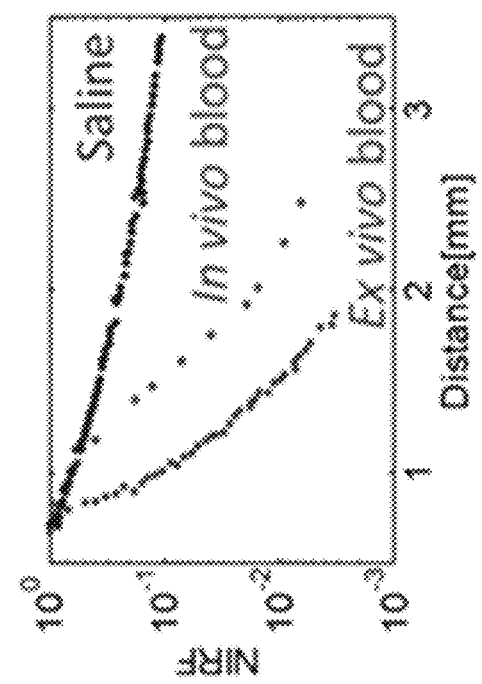

In practice, an experimental set-up schematically illustrated in FIG. 5A was employed to determine the distance-dependent attenuation parameters in blood. A pull-back of the cNIRF-IVUS channels of the catheter was performed at an angle to a target 510 represented by tube filled with AlexaFluor 750. By combining the results of ultrasound-based measurements of distance with NIRF intensity measurements, the $\alpha(r)$ was calculated based on fitting the measurements to the Twersky model for transmission measurements for both saline and blood ex vivo (FIG. 5E). For determining the distance-attenuation function $\alpha(r)$ in vivo, on the other hand, additional measurements were performed to analyze fluorescence intensity acquired from AlexaFluor 750 during the intravascular measurements in living swine, after injecting the fluorochrome directly into the vessel wall (see Section "(D) Validation of cNIRF-IVUS Embodiment of the Invention In Vivo" below for details), with results also presented in FIG. 5E.

Empirical data, presented in FIG. 5E demonstrates astonishing differences between signal attenuation levels obtained in blood ex-vivo vs. those in-vivo. The decreased attenuation by in vivo blood compared to ex vivo blood could be due to differences in oxygenation levels of blood, presence of flow, or effect of absorption flattening. In either case, these results evidence that the straightforward application of the multi-modal NIRF-IVUS catheter for dynamic real-time characterization of blood attenuation during the in vivo measurements inevitably produces erroneous results unless judicious measures are taken to correct the errors.

(B) Methodology for Distance-Related Attenuation Correction.

In correcting the acquired NIRF signals for a distance-dependent attenuation in vivo blood, one could consider that the detected fluorescence is generated by the superficial layer of the arterial wall and then undergoes attenuation in blood as fluorescent light propagates from the vessel wall to the collecting optics. This consideration finds ample support in related art, which demonstrated that binding of indocyanine green (ICG) occurs close to the inner surface of the vessel wall and that model plaque tissue provides markedly less attenuation of NIRF signals compared to blood. Accordingly, the amplitude P of the detected fluorescence signal can be modeled as $$P = P_0 C R/\alpha(r), \quad \text{(Eq. 1)}$$

where $P_0$ is the amplitude of the illumination at the tip of the light-collecting optical fiber, C is the unknown concentration of fluorophores within the detected volume, R is a constant related to optical properties of the imaged fluorescent probe such as absorption coefficient and quantum yield, and $\alpha(r)$ is the value of the distance-dependent attenuation function. According to Eq. 1, the true fluorophore concentration can be found by dividing the measured signal by $P_0 R/\alpha(r)$:

$$C = \frac{P\alpha(r)}{P_0 R}. \quad \text{(Eq. 2)}$$

It can be seen from Eq.2, the parameter $P_0 R$ scales the concentration linearly if no quenching occurs. In practice, system calibration for $P_0 R$ is required for the specific imaging probe imaged. Otherwise, the measured concentration C may only be represented in arbitrary units.

Such calibration was performed by relating the NIRF signal, collected from an in vivo fluorescence phantom, to the known concentrations and distances from the in vivo of the phantom in controlled measurements (See Section "Calibration Procedure" below and FIGS. 5A-5F). In case of measurements in water or saline, the function $\alpha(r)$ could be described by the Beer-Lambert law. However, since light propagation through blood is diffusive due to photon scattering, the Twersky theory for transmission measurements was employed. According to the Twersky theory (Twersky V, Absorption and multiple scattering by biological suspensions, J. Opt. Soc. Amer., 1970, 60(8): 1084; the disclosure of this publication is incorporated by reference herein), the distance-dependent attenuation of light in such case is written as:

$$\alpha(r) = e^{-r(\mu_{\alpha 1} + \mu_{\alpha 2})}(e^{-B\omega(1-\omega)2r} + q(1 - e^{-B\omega(1-\omega)2r})), \quad \text{(Eq. 3)}$$

where $\mu_{\alpha 1}$ and $\mu_{\alpha 2}$ are the absorption coefficients of blood at excitation and emission wavelengths, respectively, which could be found, for example, from the extinction coefficients in Bosschaart et al. (Lasers Med. Sci., 2014, 29(2): 453-79), co is the fractional hematocrit of blood which could be measured, B represents scattering, and q is a parameter of imaging system. B and q could be found empirically by curve fitting the experimental data to the expression given in Eq. 3.

A person of skill would appreciate that noise in the detected signal P may be amplified (according to the correction formula of Eq. 2) and lead to spurious signals. To address this problem, the distance correction had to be regularized to address the noise issue. This was achieved with a regularization function β introduced to suppress any signal below the noise level to minimize their subsequent amplification:

$$C = P\beta\alpha(r)/P_0 R \quad \text{(Eq. 4)}$$

β is a function of the detected signal P and could be described by equation $$\begin{cases} \beta = 32\left(\frac{P}{P + P_{noise}} - \frac{1}{2}\right)^2, \text{ if } P \leq 3 P_{noise} \\ \beta = 1 - 32\left(\frac{P}{P + P_{noise}} - \frac{1}{2}\right)^2, \text{ if } P > 3 P_{noise} \end{cases} \quad \text{(Eq. 5)}$$

where $P_{noise}$ is noise level of the detected signal. Once distance-dependent attenuation function $\alpha(r)$ is found, Eq. 4 can be used for attenuation correction of the NIRF signals and to increase the accuracy of quantification of the biological response of the target tissue, represented by the fluorescent image by modifying such image based on distance-dependent $\alpha(r)$.

(C) Calibration Procedure.

To confirm the practical feasibility and validate the devised methodology for distance-correction of fluorescent data, a 15 mm cNIRF-IVUS pull-back was performed with the same set-up of FIG. 5A. The resulted raw NIRF image is shown in FIG. 5C, clearly demonstrating that the concentration of fluorochrome in the tube 510 varies along the length of the tube. Weighting of the acquired image data according to Eq. 4 was applied to the recorded NIRF signals. The distance-attenuation model $\alpha(r)$ measured in saline was used for correction. Notably, NIRF intensities were recovered revealing constant, as was known, concentration of the fluorophore in the tube 510 (FIG. 5D), compared to the initial erroneous raw data of FIG. 5C.

The results of FIG. 5C, 5D confirm the potency and practical correctness of the proposed solution to perform distance related attenuation correction of fluorescence intensities given a determined attenuation function $\alpha(r)$.

D) Sensitivity of cNIRF-IVUS Combined Modality of the Invention to Haematocrit Changes Another thus-far not addressed question is whether the cNIRF-IVUS system could be employed to dynamically (and, alternatively or in addition, in real time) to characterize blood attenuation during experimental measurements. To address this unknown, the measurements were perform to determine whether cNIRF-IVUS joint modality could be sensitive to hematocrit (HCT) changes, by building the phantom schematically shown in FIG. 5B. Here, a flexible fluorescent tube 512 containing AlexaFluor 750 was placed next to the multi-modal catheter 314 in a substantially tangentially-parallel relationship. The overall diameter of the tube/catheter phantom was 2.6 mm, that is small enough to be inserted to the aorta of living pig through a 9F introducer unit. In-vivo measurements of the phantom arrangement were performed under regular HCT levels ("solid" dots in FIG. 5F) and following dilution of HCT to 0.25, using saline perfusion ("diluted" dots in FIG. 5F), confirmed by independent HCT blood analysis. Lines in FIG. 5F represent fits of the data representing in vivo blood measurements of FIG. 5E to Twersky model with $R^2 = 0.98$ with parameters q=0.32 and B=24.9.

E) Adaptation of cNIRF-IVUS Embodiment to Blood Attenuation Conditions.

The above-discussed phantom measurements confirmed the ability of the cNIRF-IVUS system of the invention to track attenuation changes of blood with knowledge of the results of measurements related to known fluorochromes, and the measurements of sensitivity of the measurement set-up to haematocrit changes proved the operability of the embodiment during the measurements under dynamically-changing conditions.

The next step was to understand whether the operation of the embodiment of the invention was possible under the conditions imposed by dynamic blood-attenuation changes in-vivo during intravascular measurements. Here, the cNIRF-IVUS intravascular imaging data represented by FIGS. 6A, 6B, 6C, and 6D was acquired in vivo from an intact vessel after systematic injection of fluorescent agent. During the experiment, a low-frequency varying fluorescence intensity component was unexpectedly discovered that correlates with the catheter-to-vessel-wall distance, which can be employed to dynamically estimate blood-attenuation characteristics in vivo.

Figure 6A:
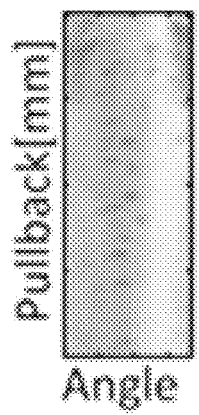
FIGS. 6A, 6B, 6C, and 6D illustrate an attenuation function derived from in vivo measurements in an unaltered vessel without a prior knowledge of blood parameters.
Figure 6B:
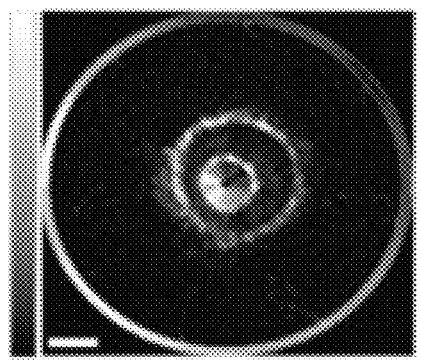
Figure 6C:
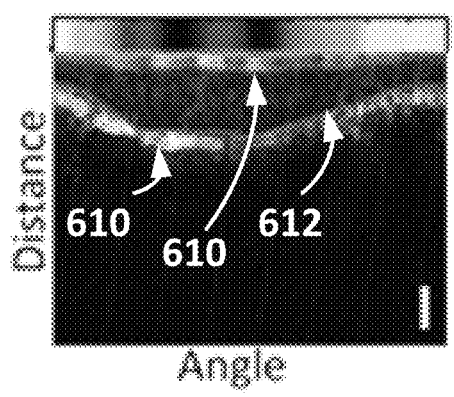
Figure 6D:
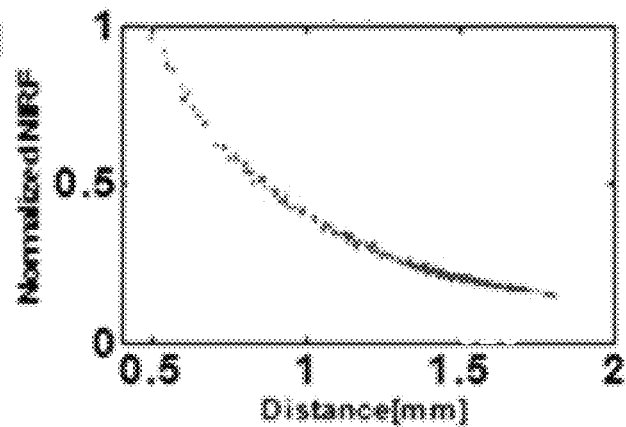

FIGS. 6A, 6B show representative examples of fluorescence distribution in an unaltered vessel as captured by the cNIRF-IVUS catheter. FIG. 6C displays a NIRF-IVUS cross-section in Cartesian coordinates where the vessel wall and the catheter are outlined by red and magenta lines, respectively. By plotting the fluorescence intensity values normalized for beam size at a corresponding distance as discussed above in reference to FIGS. 5A-5F, the attenuation function $\alpha(r)$ in vivo was obtained without a priori knowledge of blood parameters, which can be employed to dynamically monitor changes of blood attenuation, e.g. due to HTC variations.

FIG. 6C displays a NIRF-IVUS cross section in Cartesian coordinates where the vessel wall and the catheter are outlined by lines 610, 612, respectively. These findings signify the cNIRF-IVUS ability to retrieve the attenuation function $\alpha(r)$ in vivo, which can be employed to dynamically monitor against changes of blood attenuation during intravascular measurements with an embodiment of the invention.

The empirical results also suggest that dynamic, real-time observations of blood attenuation with the proposed hybrid methodology can be used in cases of efficient clearance of the fluorochrome from the blood circulation and, therefore, they can be utilized after allowing sufficient time for fluorochrome clearance. Notably, such practice would be consistent with the administration of fluorescent agents targeting biological biomarkers, since it also allows time for efficient targeting and maximizes imaging contrast as well. Referring again to FIG. 3, it is understood that image-data processing, correction, co-registration between the ultrasound-based imaging data and optical imaging data, and the formation of the final, corrected hybrid images is facilitated with the electronic circuitry unit 340 equipped with programmable computer-readable processor specifically-configured to implement the error-correcting methodology discussed above.

F) Validation of cNIRF-IVUS Embodiment of the Invention In Vivo.

Figure 7D:
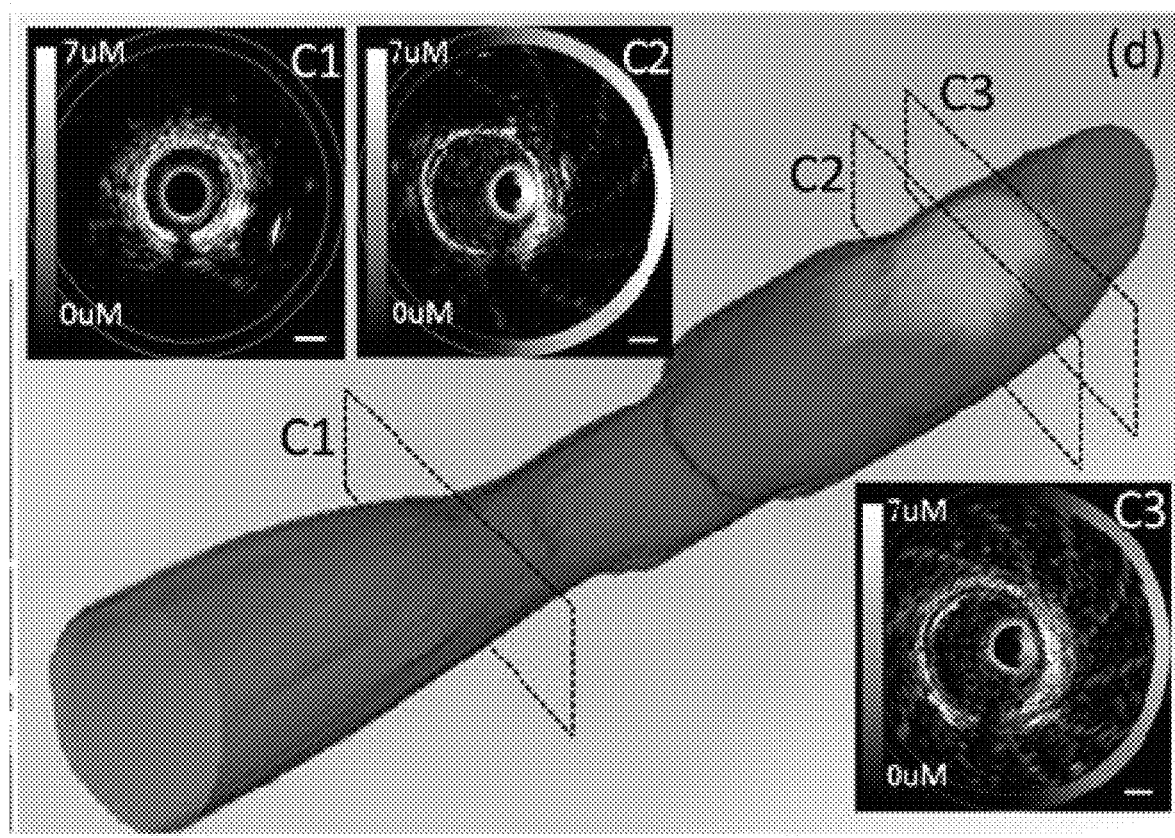
Figure 7F:
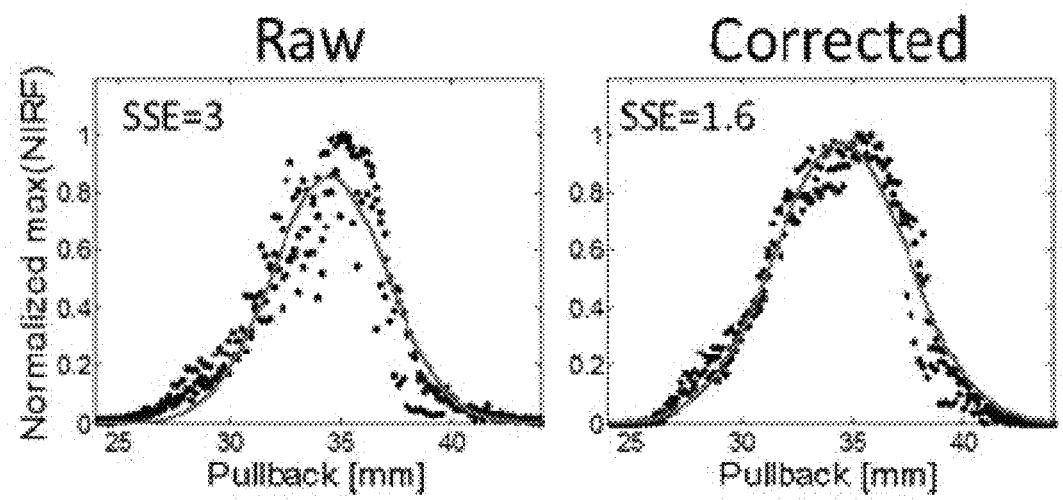

In an initial set of in vivo experiments, performed with the 40 MHz version of the hybrid catheter 314, the ability of such catheter to obtain cNIRF-IVUS image data in vivo through blood in a reproducible manner was assessed. Imaging was thus performed in vivo in the carotid artery of a pig (similar diameter as human coronary arteries, therefore suitable for this experiment with the 40 MHz, 1.5 mm diameter catheter). A 750 nm NIR fluorophore (AF750, 0.2 mL, concentration 50 μM) was injected directly into the outer wall of the proximal carotid artery. Three sequential cNIRF-IVUS 70 mm pullbacks through blood flow were performed using rotational speeds of either 160 rpm or 80 rpm and pullback step size of 0.2 mm. Between pullbacks, the catheter was re-advanced to the same starting position using x-ray fluoroscopic guidance. FIG. 7A shows an FRI image of the artery obtained ex vivo. The cNIRF image shown in FIG. 7B was measured in vivo and simultaneously with corresponding longitudinal IVUS (FIG. 7C). The NIRF images from all three pullbacks before and after distance correction are shown in FIG. 7E. Although the same region of the vessel was scanned, significant inconsistency was observed among the uncorrected NIRF images (FIG. 7E, top row). This finding can be explained by the varying intraluminal catheter position after re-advancements and variations in the catheter position inside the artery due to blood flow and respiratory motion. Distance correction of the NIRF signals, based on the exactly co-registered IVUS image depicting the catheter position, substantially improved the consistency of the NIRF results (FIG. 7E, bottom row). The positive effect of the correction is also evident from the maximum intensity of the NIRF signals in every pullback position for all three pullbacks (FIG. 7F, black dots). Strong dispersion of data points around the average distribution (blue line, the sum of squares due to error SSE=3) in the case of raw NIRF signals shows a negative effect (image degradation) from rapid motions during pullback. Better consistency of the NIRF signals from all three pullbacks was achieved by distance-correction (SSE=1.6). Finally, the combined cNIRF-IVUS data set was used for generating a co-registered 3D-rendered image of the lumen and fluorescence activity, shown in FIG. 7D. Insertion C1, C2 and C3 shows representative examples of the cross-sectional cNIRF-IVUS images corresponding to pull back positions C1, C2 and C3 in FIGS. 7B, 7C, and 7D.

Complementary Examples: Ex Vivo Validation

To validate the system and correction algorithm in experimental conditions resembling animal measurements, the hybrid catheter was placed inside an abdominal rabbit aorta ex vivo. Next, an NIR fluorophore (AlexaFluor750, 0.15 ml volume, concentration 0.5 mg/ml) was locally injected into the wall of aorta to simulate fluorophore accumulation in plaque. The diameter of the vessel was approximately 4 mm. The same region of the vessel was scanned 3 times with the 40 MHz cNIRF-IVUS catheter. Between pullbacks, the cNIRF-IVUS catheter was manually re-advanced into the same starting point but placed in a different intraluminal position for each pullback (positions 1-3). Subsequently, the NIRF signals were corrected for distance variations according to the algorithm of the invention described above.

FIG. 8A shows representative cross-sectional hybrid NIRF-IVUS images of the vessel. A colored circular ring in the center shows NIRF signal before and after the correction. The raw and corrected NIRF signals obtained over whole pullbacks are displayed next to the hybrid cross sectional images.

A visual comparison of the corrected NIRF images in FIG. 8B clearly shows greater consistency compared to uncorrected images. For example, the raw NIRF images shown in FIG. 8A for positions 2 and 3 manifest a strong signal at 4-6 o'clock owing to the vicinity of the blood vessel in these angles. In comparison, the raw NIRF image in position 1, in which the catheter is located further from the artery wall (at about 4-6 o'clock location in the image), shows a lower response at these angles. In the corrected images, the signal depicted at about 4-6 o'clock location in the image is consistent among all three positions. The effect of the correction on the consistency of the NIRF signals may be also appreciated from their 1D plots shown in FIG. 8C.

To quantitatively analyze reproducibility of corrected NIRF data, two parameters were computed for images obtained in different intraluminal positions: a) correlation coefficient between 2D NIRF images; b) relative standard deviation (RSD) between energies of the fluorescence signals. Energy of each signal was calculated as followed:

$$E = \rho_i m_i^2, \tag{7}$$

where $m_i$ is intensity of the pixel, and i is a number of pixels in the NIRF image. All reproducibility analysis parameters are shown in Table 1 below.

TABLE 1

Reproducibility analyzes of the ex vivo measurements.

a.

| | Raw images correlation | | | Corrected images correlation | |
|---|---|---|---|---|---|
| | Position 2 | Position 3 | | Position 2 | Position 3 |
| Position 1 | 0.6924 | 0.5283 | Position 1 | 0.9483 | 0.9054 |
| Position 3 | 0.7725 | | Position 3 | 0.9113 | | b.

| | Energy of the Raw signal | Energy of the Corrected signal |
|---|---|---|
| Position 1 | 2.87E+13 | 3.48E+05 |
| Position 2 | 2.12E+13 | 2.68E+05 |
| Position 3 | 2.31E+13 | 2.35E+05 |
| RSD, % | 16.08 | 20.47 | a. Correlation coefficients between raw and corrected NIRF images presented in FIGS. 8A through 8C.
b. RSD calculation for raw and corrected NIRF images.

Although the RSD slightly increased (from 16.08% to 20.47%), distance correction resulted in a 26% higher correlation between NIRF images (average correlation 66% before correction, 92% after correction). This demonstrates a positive effect of the correction on the reliability of NIRF imaging. In order to simulate scenario where, instead of a small catheter movement, significant repositioning within the vessel occurs, the catheter was placed in top-right and bottom-center positions (as shown in FIGS. 9A, 9B).

Figure 9A:
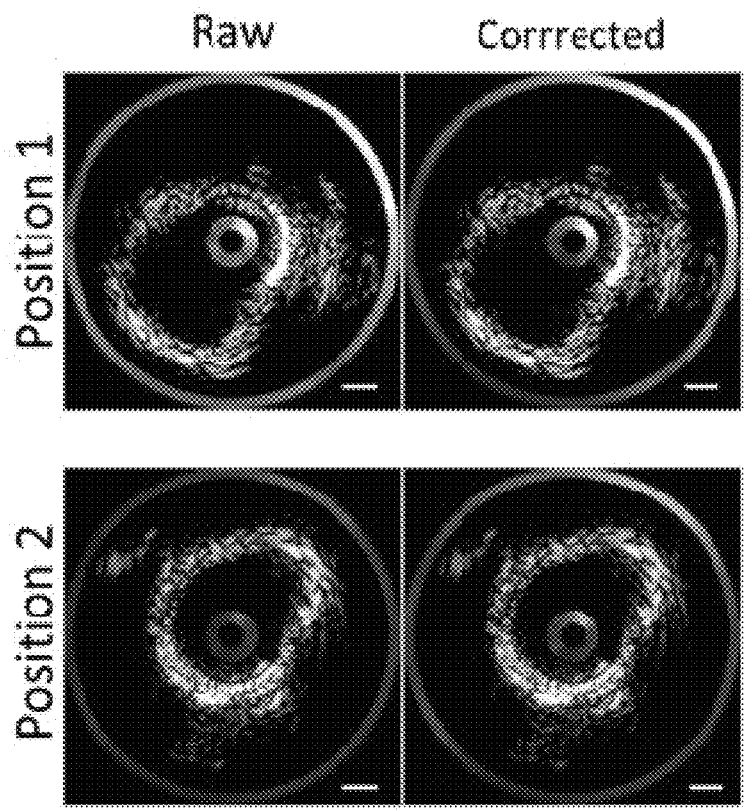
FIGS. 9A, 9B illustrate the results of ex vivo measurements, effectuated with an embodiment of the invention in abdominal rabbit aorta with AF750 injected into the vessel wall.
Figure 9B:
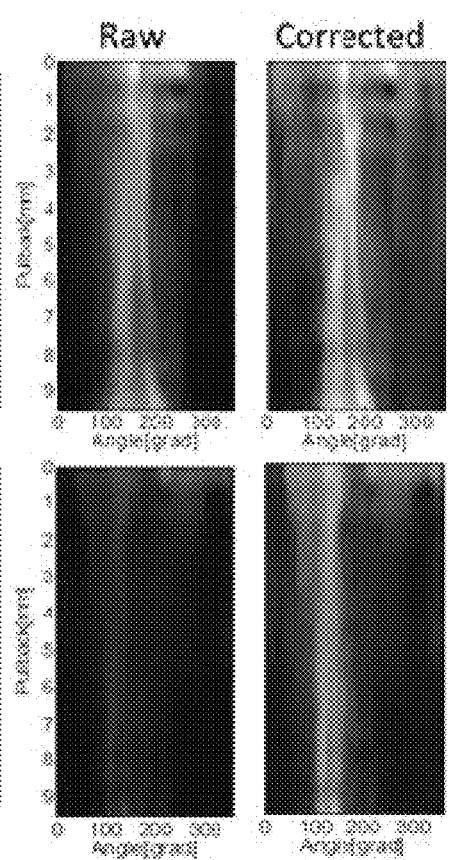

In cases of eccentric catheter position, the maximum amplitude of the NIRF signal in FIGS. 9A, 9B position 1 was considerably stronger compared to the maximum amplitude of the signal in FIG. 9A, 9B position 2. Nevertheless, the NIRF signals were reasonably normalized with the use of the distance correction approach of the present invention. Reproducibility analysis showed that after correction RSD was reduced to half: from 100.29% to 57.12% (see Table 2).

TABLE 2

RSD calculation for raw and corrected
NIRF images presented in FIGS. 9A, 9B.

| | Energy of the Raw signal | Energy of the Corrected signal |
|---|---|---|
| Position 1 | 7.79E+12 | 3.66E+04 |
| Position 2 | 1.33E+12 | 1.56E+04 |
| RSD, % | 100.29 | 57.12 |

Figures 10A, 10B:
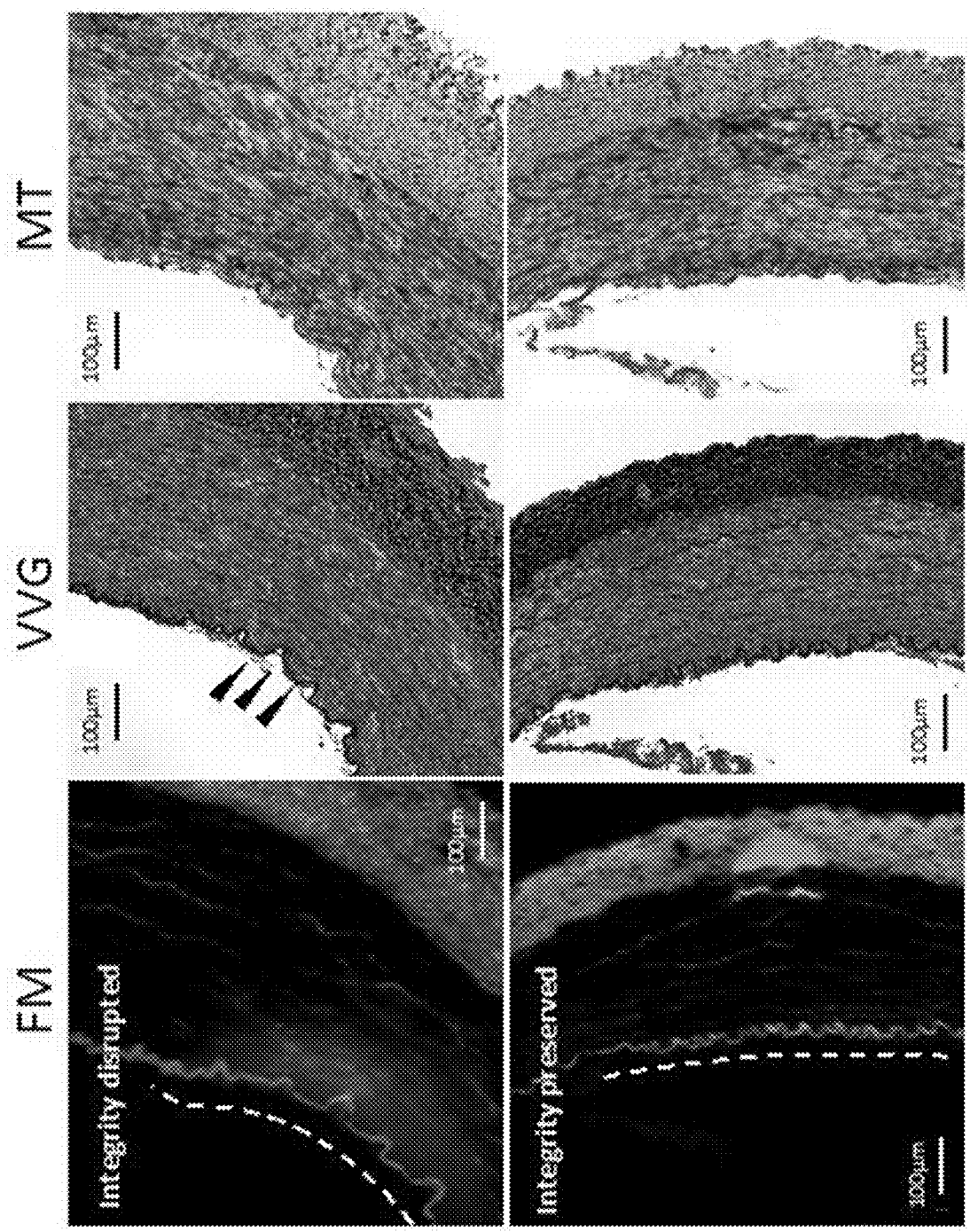
FIGS. 10A, 10B show ICG targets areas of vascular injury after balloon angioplasty. Verhoeff-Van Gieson (VVG) elastin stain and Masson's Trichrome (MT) stain shows co-localization of the ICG NIR fluorescence to the arterial wall, just below areas of elastin fiber stretching and possible disruption.

Complementary Examples: Histological Assessment of ICG Deposition and Vascular Injury in Swine Iliac Arteries After surgically resecting the injured artery and performing ex vivo FRI, each artery was placed in cold saline. Iliac artery rings were cut and subsequently embedded in optical cutting temperature compound (Sakura Finetek), frozen in chilled isopentane, and sectioned in 6 μm segments. Fluorescence and brightfield microscopy was performed using an epifluorescence microscope (Nikon Eclipse 90i; Tokyo, Japan). ICG deposition in the injured was detected with a near-infrared fluorescence filter (ex/em 775/845 nm). Autofluorescence was detected using a FITC filter (ex/em 480/535 nm). Elastin staining with Verhoeff-Van Gieson (VVG; HT-25a kit, Sigma) and collagen staining with Masson's Trichrome (MT; HT 15 kit, Sigma) was performed according to the manufacturer's directions to show elastin and collagen, respectively. ICG deposited particularly within injured arteries, as evidenced by stretched and disrupted elastin fibers (FIGS. 10A, 10B).

Complementary Examples: In Vivo NIRF-IVUS Imaging of Atherosclerosis.

Figure 11A:
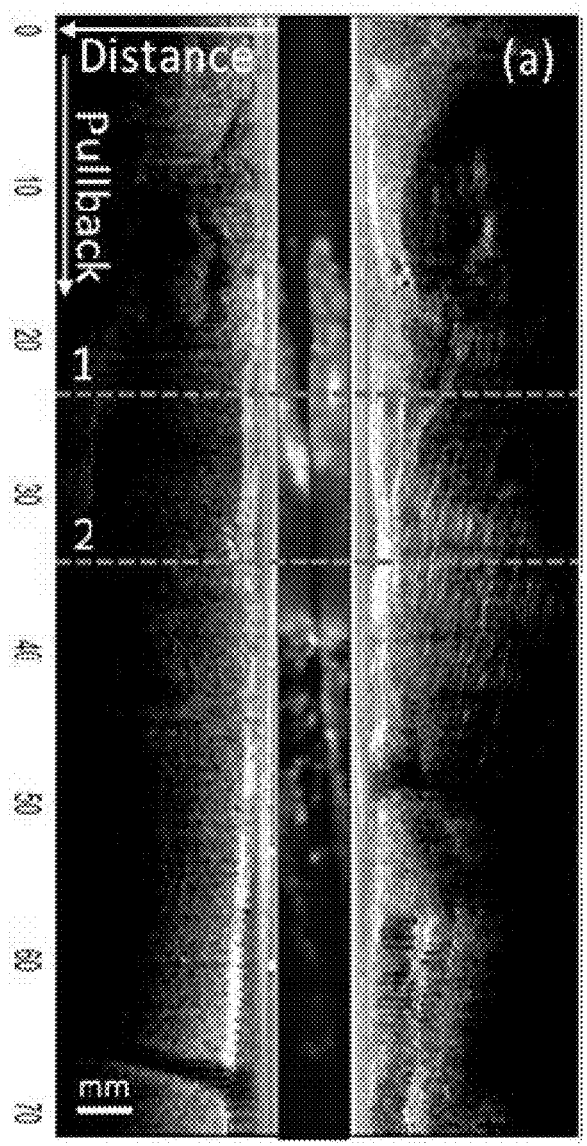
FIGS. 11A, 11B, 11C address the use of the multi-modal (NIRF-IVUS) embodiment of the invention for in vivo imaging of atherosclerosis.
Figure 11B:
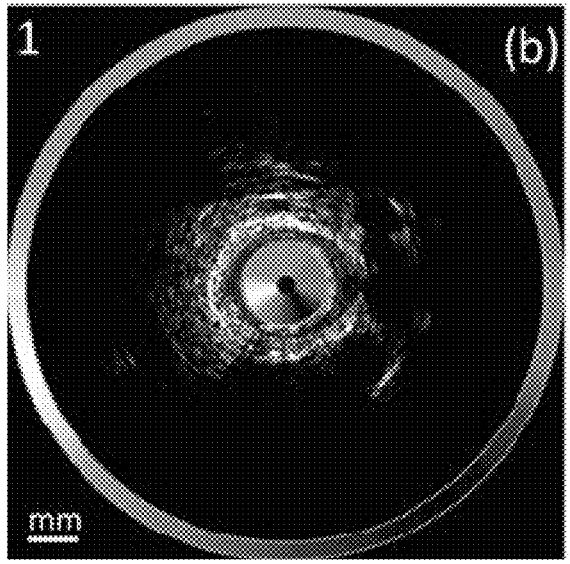
Figure 11C:
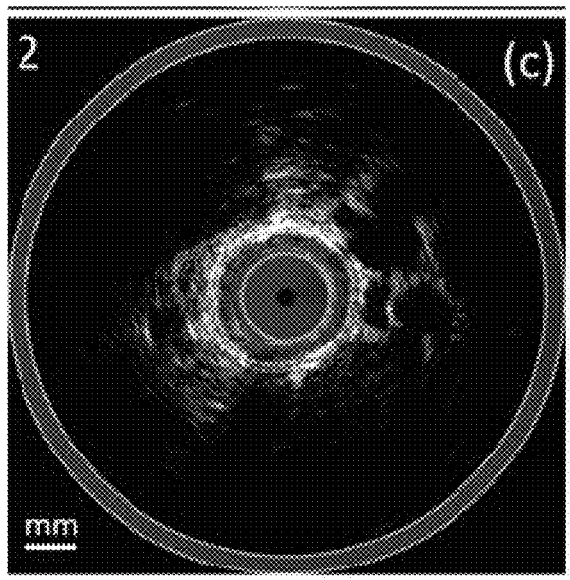

To demonstrate NIRF-IVUS system to image atherosclerosis-related biological parameters we employed a New Zealand rabbit model. After balloon-induced injury procedure the animal was fed a high cholesterol diet. ProSense VM110 (4 mg/kg IV, ex/em 750/780 nm) was injected 24 hours before imaging. 5F introducer was placed in the distal carotid artery. Then, the 40 MHz version of the NIRF-IVUS catheter of the invention was inserted through the sheath retrograde into the proximal carotid artery and advance to the area of injury. A 70 mm NIRF-IVUS pullback was performed with rotation speed of 120 rpm revealing two diseased areas (12-30 mm and 38-50 mm at FIG. 11A) with 7 mm healthy region in between. Cross sectional NIRF-IVUS images in FIGS. 11B and 11C demonstrate difference(s) between diseased and healthy region of the vessel.

As is understood by a skilled person, discussed embodiments of the invention provide a fluorescence-imaging system that is not biased by the discovered dependence of the imaging data on location of the multi-modality intravascular catheter within the imaged blood vessel. Such unbiased imaging is realized by contemporaneous acquisition of the ultrasound images and use of the so acquired ultrasound imaging data not only to register the fluorescence signals on morphological IVUS images, but also to correct fluorescence images for intensity variations associated with the non-zero distance that both the fluorescence-exciting light and fluorescence emission propagate through blood in vivo. While this distance-biasing effect may or may not be generally present also as a function of the particular geometry characteristics, it is accentuated when NIRF intravascular imaging is performed in the presence of luminal blood, owing to the strong optical absorption and scattering of blood. The performance of the developed cNIRF-IVUS system, as assessed in both ex vivo and in vivo, demonstrated clear improvements in imaging fidelity and accuracy, compared to uncorrected images, as confirmed by FRI, histological analysis, and two-channel fluorescence microscopy images.

According to the idea of the invention, images formed with the use of optical data received by acquisition of fluorescence signal(s) are corrected with the use of acoustic data (acquired through the IVUS channel of an embodiment of the invention) while using the formed ultrasound images as anatomical reference. To perform the correction properly, the NIRF-based images the and the IVUS-based images have to be spatially co-registered.

The term co-registration and related terms, when used in reference to constituent images obtained with different imaging modalities onto the same geometrical frame, are used to denote a process of alignment of such images so that pixels/voxels seen on the first image space correspond to the same pixel/voxel in a space pf the second image. It is appreciated that, in the example of the NIRF- and IVUS-combining embodiment of FIG. 3—in absence of the image co-registration neither one can use the IVUS images for correction of NIRF images nor plot NIRF images on ultrasound images for rendering purposes.

Unless specified otherwise, the term "image" generally refers to an ordered representation of detector output corresponding to spatial positions. For example, a visual image may be formed, in response to a pattern of light detected by an optical detector, on a display device such as a video screen or printer. In vivo imaging revealed that the developed cNIRF-IVUS system and derived correction algorithm can minimize errors caused by variable signal attenuation in blood, and can significantly improve the reliability of the NIRF measurements. In contradistinction with a situation when the ultrasound transducer containing channel may be rotated independently from the NIRF channel, reliable co-registration of the morphology and fluorescence intensities in the present system was achieved by the simultaneous and co-dependent (characterized by the same rate) rotation of the NIRF and IVUS channels about the axis of the multi-channel catheter and combining both the acoustic and NIRF detectors into an all-in-one rotating element. In a related embodiment, co-registration could be achieved by other means, for example with the fiduciary markers on the catheter system. In this case the two imaging modalities could operate more independently.

It is appreciated, therefore, is aimed at an hybrid-modality system and method a method for intravascular imaging of a target through a biological fluid in vivo. Such method includes the use of first and second radiation channels of a multi-channel catheter having an axis, to intravascularly detect, through said biological fluid in vivo, a first radiation that is generated at the target as a result of absorption by the target of a second radiation (that has been delivered to the target through one of the first and second radiation channels) to form a first representation of a biological response of the target to the second radiation. The method further includes simultaneously with intravascularly detecting of the first radiation, detecting a second radiation (produced at the target in response to insonation of said target with a fourth radiation delivered to the target through another of the first and second radiation channels) to form a second representation of a morphological characteristic of a target. The first and second representations may be images of the target. The method further includes a step of determining a distance-dependent characteristic of said biological fluid in vivo (which characteristic represents at least one of absorption and scattering of at least one of the first and second radiations in said biological fluid in vivo). Furthermore, the method additionally includes a step of transforming the first representation to a third representation that is devoid of a distance-dependent bias caused by such absorption and scattering. All these steps tie the determination of a distance-dependent characteristic of an in-vivo biological fluid to the processor's ability to process digital images. The additional step of comparing the second and third representations to define a visually-perceived representation of the target that combines biological and morphological features of said target represents an innovation in medical diagnostic technology.

For the purposes of this disclosure and accompanying claims, a real-time performance of a system is understood as performance which is subject to operational deadlines from a given event to a system's response to that event. For example, a real-time characterization of the vessel based on acquisition of intravascular imaging data may be one during which the final images, formed based on co-registration of individual images of the vessel obtained with different imaging modalities, are formed and corrected for ambient-medium-dependent errors on the time-scale substantially equal to the time-scale of imaging data acquisition and recordation.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself Processes of optical and/or acoustic data acquisition and processing in embodiments of the invention have been described as including a processor controlled by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, when the present disclosure describes features of the invention with reference to corresponding drawings (in which like numbers represent the same or similar elements, wherever possible), the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, at least for purposes of simplifying the given drawing and discussion, and direct the discussion to particular elements that are featured in this drawing.

The invention as recited in claims appended to this disclosure is intended to be assessed in light of the disclosure as a whole, including features disclosed in prior art to which reference is made. Disclosed aspects, or portions of these aspects, may be combined in ways not listed above. Changes may be made without departing from the scope of the invention. In view of the numerous possible embodiments to which the principles of the disclosed invention may be applied, the invention should not be viewed as being limited to any specific example.

The invention claimed is:

1. A method for intravascular imaging of a target, the method comprising:
   simultaneously acquiring, from a blood vessel containing blood in vivo, with a combination of first and second energy propagation channels of a multi-channel catheter having an axis,
      (i) a fluorescence wave generated at the target in the hollow organ as a result of absorption, by the target, of an excitation wave that has been delivered to the target through one of the first and second energy propagation channels, and
      (ii) an acoustic response wave, produced at the target by exposing said target to an ultrasound excitation wave delivered to the target with the use of the other of the first and second energy propagation channels;
   forming a first representation of biological activity in the target using the fluorescence wave and forming a second representation of a morphological characteristic of the target based on the third wave acoustic response wave;
   transforming a combination of the first and second representations into an image of the target that is devoid of a distance-dependent error by correcting variations in intensity of the fluorescence wave based on a distance-dependent function of attenuation of light by blood,
      wherein said distance-dependent function is defined without prior knowledge of blood parameters and wherein said distance-dependent function represents sensitivity of measuring the fluorescent wave to changes in hematocrit.

2. The method according to claim 1,
   wherein said correcting of variations in intensity is carried out in real-time while said simultaneously acquiring occurs.

3. The method according to claim 1,
   wherein said distance-dependent error is caused by at least one of absorption and scattering of at least one of the fluorescence wave and the excitation wave upon propagation of said at least one of the fluorescence wave and the excitation wave through the blood in vivo.

4. The method according to claim 1, further comprising increasing accuracy of quantification of said biological activity in vivo by suppressing a signal representing the fluorescent wave acquired with the catheter when said signal is below a pre-determined noise threshold.

5. The method according to claim 1,
   wherein the transforming a combination of the first and second representations into said image includes forming a visually-perceivable representation of the target that combines biological and morphological features of said target.

6. The method according to claim 1, further comprising simultaneously and co-dependently rotating the first and second energy propagation channels about the axis.

7. The method according to claim 6, including introducing mechanical offsets between the first and second energy propagation channels in the catheter, the mechanical offsets being dimensioned to equate characteristic of rotation of said first and second energy propagation channels during said simultaneously and co-dependently rotating.

8. The method according to claim 1, further comprising spatially co-registering the first and second representations prior to said transforming.

9. The method according to claim 8, further comprising determining a distance-dependent characteristic, of said blood in vivo, representing at least one of absorption and scattering of at least one of the fluorescence wave and the excitation wave upon propagation of said at least one of the fluorescence and excitations waves through said blood in vivo, and
   wherein said spatially co-registering occurs after said determining.

10. The method according to claim 1, further comprising detecting, through a third channel of said catheter, a wave representing anatomical characteristics of said target and containing optical-computed-tomography (OCT) information.

11. The method according to claim 1, wherein the simultaneously acquiring includes propagating a wave transmitted through said one of the first and second energy propagation channels i) along the axis in a first portion of such channel and ii) along a line that is transverse to the axis in a second portion of such channel.

12. The method according to claim 1, wherein the simultaneously acquiring includes transmitting an electrical signal along said other of the first and second channels, said electrical signal being caused by the acoustic response wave.

13. A method for intravascular imaging of a target, the method comprising:
   with the use of a detection system operably connected to a proximal end of a multi-channel catheter that is configured to channel simultaneously fluorescence wave, excitation wave, and an electrical signal therethrough, simultaneously detecting
      (i) an optical signal representing the fluorescence wave transmitted from the target through blood in vivo in response to irradiation of the target by the excitation wave, and
      (ii) the electrical signal representing an acoustic wave, transmitted from the target through said blood in vivo;
   spatially co-registering first and second images of the target, formed based on said optical signal and said electrical signal, wherein the first and second images aggregately contain a representation of biological activity in the target and a representation of a morphological characteristic of the target;
and
transforming one of the first and second images to create a third image in which visual information representing said biological activity has been corrected with the use of a distance-dependent function of attenuation of light in blood to remove a distance-dependent error in said optical signal caused by presence of the blood in vivo, wherein said function is defined without prior knowledge of blood parameters and represents sensitivity of detection of the optical signal to changes in hematocrit.

14. The method according to claim 13, further comprising determining said distance-dependent function, said function differentiating said blood in vivo from blood ex vivo in at least one of (i) an oxygenation level; (ii) intravascular flow; and (iii) radiation absorption effects.

15. The method according to claim 13, further comprising comparing the second and third images to form a visually-perceivable representation of the target that combines biological and morphological features of said target.

16. An apparatus for obtaining information regarding at least one portion of a biological target, the apparatus including:
a catheter having proximal and distal ends and an axis, the catheter containing first and second channels configured to transmit, aggregately, at least first, second, and third waves through blood in vivo separating the catheter from the biological target,
wherein the first channel includes a waveguide configured to transmit the first wave containing fluorescence generated within the biological target in response to absorption, by the biological target, of the third wave containing optical excitation wave,
wherein the second channel includes a waveguide configured to transmit, from the biological target, the second wave that represents anatomical characteristics of the target and that is caused by least one of an acoustic response wave and an optical response wave generated at the target in response to at least one of mechanical and optical waves that have been transmitted from the catheter to the target;
an energy detection system including an optical detector in operable communication with the proximal end, the energy detection system configured to acquire wave energy from the catheter to produce output data representing the target and including a first data portion representing the first wave and a second data portion representing the second wave;
and
a programmable computer processor operably cooperated with a non-transitory tangible computer-readable storage medium containing computer-readable code that, when loaded on the programmable processor, causes said programmable processor
to form a first representation of biological activity in the target using the first wave and a second representation of a morphological characteristic of the target based on the second wave, and
transform a combination of the first and second representations into an image of the target by correcting variations in intensity of the fluorescence based on a distance-dependent function of attenuation of light by blood,
wherein said image is devoid of a distance-dependent error that is caused by at least one of absorption and scattering of at least one of the first and third waves upon propagation of said at least one of the first and third waves through the blood in vivo, and
wherein said function is defined without prior knowledge of blood parameters and wherein said function represents sensitivity of measuring the fluorescent radiation to changes in hematocrit.

17. An apparatus according to claim 16, wherein each of the first and second channels is structured to redirect a wave transmitted through such channel to cause this wave traverse a first portion of such channel along the axis of the catheter and a second portion of such channel along a line that is transverse to the axis of the catheter.

* * * * *

UNITED STATES PATENT AND TRADEMARK OFFICE
CERTIFICATE OF CORRECTION

PATENT NO. : 11,123,047 B2  
APPLICATION NO. : 15/130820  
DATED : September 21, 2021  
INVENTOR(S) : Farouc A. Jaffer et al.

Page 1 of 1

It is certified that error appears in the above-identified patent and that said Letters Patent is hereby corrected as shown below:

In the Claims

Column 23, Claim 1, Line 48, "the third wave acoustic" should be --the acoustic--.

Column 25, Claim 16, Line 39, "by least" should be --by at least--.

Signed and Sealed this  
Thirtieth Day of November, 2021

Drew Hirshfeld  
*Performing the Functions and Duties of the  
Under Secretary of Commerce for Intellectual Property and  
Director of the United States Patent and Trademark Office*